(12) United States Patent
Thompson, III et al.

(10) Patent No.: US 8,604,024 B2
(45) Date of Patent: Dec. 10, 2013

(54) COMPOUNDS FOR THE REDUCTION OF BETA-AMYLOID PRODUCTION

(75) Inventors: Lorin A. Thompson, III, Higganum, CT (US); Jianliang Shi, Madison, CT (US); Yong-Jin Wu, Madison, CT (US); Lawrence R. Marcin, Bethany, CT (US); Ramkumar Rajamani, Woodbridge, CT (US); Mendi A. Higgins, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/477,143

(22) Filed: May 22, 2012

(65) Prior Publication Data
US 2013/0131051 A1 May 23, 2013

Related U.S. Application Data

(60) Provisional application No. 61/489,438, filed on May 24, 2011.

(51) Int. Cl.
*C07D 279/08* (2006.01)
*C07D 513/04* (2006.01)
*C07D 417/10* (2006.01)

(52) U.S. Cl.
USPC ..................................... 514/224.5

(58) Field of Classification Search
USPC ........................... 514/224.5; 544/32
See application file for complete search history.

(56) References Cited

U.S. PATENT DOCUMENTS

2010/0093999 A1  4/2010  Motoki et al.

FOREIGN PATENT DOCUMENTS

| EP | 1 942 105 | 7/2008 |
|----|-----------|--------|
| WO | WO 2011/005738 | 1/2011 |

OTHER PUBLICATIONS

Anderson, D.H. et al., "Characterization of β amyloid assemblies in drusen: the deposits associated with aging and age-related macular degeneration," Experimental Eye Research, 78, pp. 243-256 (2004).
Cleary, J.P. et al., "Natural oligomers of the amyloid-β protein specifically disrupt cognitive function," Nature Neuroscience, vol. 8, No. 1, pp. 79-84 (Jan. 2005).
Deramecourt, V. et al., "Biochemical Staging of Synucleinopathy and Amyloid Deposition in Dementia With Lewy Bodies," J. Neuropathol. Exp. Neurol., vol. 65, No. 3, pp. 278-288 (Mar. 2006).
Goldstein, L.E. et al., "Cytosolic β-amyloid deposition and supranuclear cataracts in lenses from people with Alzheimer's disease," The Lancet, vol. 361, pp. 1258-1265 (Apr. 12, 2003).
Grundman, M. et al., "Mild Cognitive Impairment Can Be Distinguished From Alzheimer Disease and Normal Aging for Clinical Trials," Arch. Neurol., vol. 61, pp. 59-66 (Jan. 2004).
Hamilton, R.L. et al., "Alzheimer disease pathology in amyotrophic lateral sclerosis," Acta Neuropathol, 107, pp. 515-522 (2004).
Hussain, I. et al., "Identification of a Novel Aspartic Protease (Asp 2) as β-Secretase," Molecular and Cellular Neuroscience, 14, pp. 419-427 (1999).
Lin, X. et al., "Human aspartic protease memapsin 2 cleaves the β-secretase site of β-amyloid precursor protein," Proceedings of the National Academy of Sciences of the USA, vol. 97, No. 4, pp. 1456-1460, (Feb. 15, 2000).
Loane, D.J. et al., "Amyloid precursor protein secretases as therapeutic targets for traumatic brain injury," Nature Medicine, vol. 15, No. 4, pp. 377-379 (Apr. 2009).
Luo, Y. et al., "Mice deficient in BACE1, the Alzheimer's β-secretase, have normal phenotype and abolished β-amyloid generation," Nature Neuroscience, vol. 4, No. 3, pp. 231-232 (Mar. 2001).
Murphy, M.P. et al., "Inclusion-body myositis and Alzheimer disease: Two sides of the same coin, or different currencies altogether?" Neurology, 66, Suppl 1, pp. S65-S68 (2006).
Neumann, M. et al., "Ubiquitinated TDP-43 in Frontotemporal Lobar Degeneration and Amyotrophic Lateral Sclerosis," Science, vol. 314, pp. 130-133 (2006).

(Continued)

*Primary Examiner* — San-Ming Hui
*Assistant Examiner* — Kathrien Cruz
(74) *Attorney, Agent, or Firm* — John F. Levis

(57) ABSTRACT

Compounds of formula (I), including pharmaceutically acceptable salts thereof, are set forth herein:

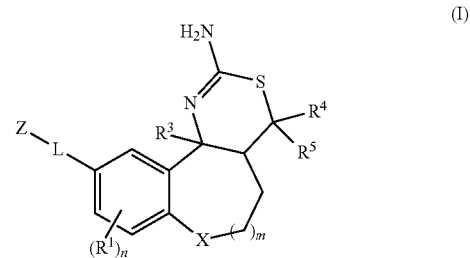

wherein X is selected from the group of $CH_2$, O, and $NR^2$;
m=0 or 1;
$R^1$ at each instance is selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, and C2-C4 alkynyl;
L is a bond, —NHCO—, —NH—, or L and Z together can be absent;
Z is a $C_6$-$C_{10}$-aryl group or a 5-10 membered heterocyclic group which can be further substituted with from 0-3 substituents selected from the group of halogen, halo$C_{1-4}$ alkoxy, 4-methoxyphenyl, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, and $C_2$-$C_4$ alkynyl;
$R^2$ is selected from the group of hydrogen, benzyl, $C_1$-$C_6$ alkyl or cycloalkyl, $C_1$-$C_6$ alkoxy, acetyl, and methanesulfonyl;
and $R^3$, $R^4$ and $R^5$ are independently selected from hydrogen or $C_{1-4}$alkyl.

8 Claims, No Drawings

(56) References Cited

OTHER PUBLICATIONS

Roberds, S.L. et al., "BACE knockout mice are healthy despite lacking the primary β-secretase activity in brain: Implications for Alzheimer's disease therapeutics," Human Molecular Genetics, vol. 10, No. 12, pp. 1317-1324 (2001).

Selkoe, D.J., "Alzheimer's Disease: Genes, Proteins, and Therapy," Physiological Reviews, vol. 81, No. 2, pp. 741-766 (Apr. 2001).

Sinha, S. et al., "Purification and cloning of amyloid precursor protein β-secretase from human brain," Nature, vol. 402, pp. 537-540 (Dec. 2, 1999).

Thal, D.R. et al., "Two Types of Sporadic Cerebral Amyloid Angiopathy," Journal of Neuropathology and Experimental Neurology, vol. 61, No. 3, pp. 282-293 (Mar. 2002).

Vassar, R. et al., "β-secretase Cleavage of Alzheimer's Amyloid Precursor Protein by the Transmembrane Aspartic Protease BACE," Science, vol. 286, pp. 735-741 (Oct. 22, 1999).

Walsh, D.M et al., "Deciphering the Molecular Basis of Memory Failure in Alzheimer's Disease," Neuron, vol. 44, pp. 181-193 (Sep. 30, 2004).

Wolfe, M.S., "Secretase Targets for Alzheimer's Disease: Identification and Therapeutic Potential," Journal of Medicinal Chemistry, vol. 44, No. 13, pp. 2039-2060 (Jun. 21, 2001).

Wolfe, M.S. et al., "Intramembrane Proteolysis: Theme and Variations," Science, vol. 305, pp. 1119-1123 (2004).

Yan, R. et al., "Membrane-anchored aspartyl protease with Alzheimer's disease β-secretase activity," Nature, vol. 402, pp. 533-537 (Dec. 2, 1999).

Yokota, 0. et al., "NACP/α-Synuclein, NAC, β-amyloid pathology of familiar Alzheimer's disease with the E184D presenilin-1 mutation: a clinicopathological study of two autopsy cases," Acta Neuropathol, 104, pp. 637-648 (2002).

Yoshida, Y. et al., "The potential role of amyloid β in the pathogenesis of age-related macular degeneration," Journal of Clinical Investigation, vol. 115, No. 10, pp. 2793-2800 (Oct. 2005).

"Consensus Recommendations for the Postmortem Diagnosis of Alzheimer's Disease," Neurobiology of Aging, vol. 18, No. S4, pp. S1-S2 (1997).

COMPOUNDS FOR THE REDUCTION OF BETA-AMYLOID PRODUCTION

CROSS REFERENCE TO RELATED APPLICATION

This non-provisional application claims the benefit of U.S. Provisional Application Ser. No. 61/489,438, filed May 24, 2011.

FIELD OF THE INVENTION

The present invention relates to compounds which are inhibitors of β-amyloid peptide (Aβ) production, as well as to methods of treating Alzheimer's Disease (AD) and other conditions related to β-amyloid production using compounds which are inhibitors of β-amyloid peptide (Aβ) production. The invention further relates to pharmaceutical compositions comprising these compounds.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme 1 (BACE1), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase. The BACE1 enzyme is a transmembrane aspartyl protease and was described in the literature by several independent groups [see Hussain, I. et al., (1999) *Mol. Cell. Neurosci.,* 14: 419-427; Lin, X. et al., (2000) *Proceedings of the National Academy of Sciences of the United States of America,* 97: 1456-1460; Sinha, S., et al., (1999) *Nature (London),* 402: 537-540; Vassar, R., et al., (1999) *Science (Washington, D.C.),* 286: 735-741; Walsh, D. M. et al., (2002); Wolfe, M. S. (2001); Yan, R. et al., (1999) *Nature (London),* 402: 533-537].

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.,* (2001) 81: 741-766). Current evidence suggests that oligomeric, protofibrillar and intracellular Aβ42 play a significant role in the disease process (Cleary, J. P. et al., *Nat Neurosci.* (2005) 8: 79-84). Inhibitors of the enzymes that form Aβ42, such as BACE1, represent potential disease-modifying therapeutics for the treatment of AD.

Evidence suggests that a reduction in brain Aβ levels by inhibition of BACE may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit BACE1 and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol (Berl)* (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB, and therefore compounds that reduce Aβ levels could reduce or prevent DLB.

Approximately 25% of ALS patients have significant dementia or aphasia (Hamilton, R. L. et al., *Acta Neuropathol (Berl)* (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol (Berl)* (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

A recent study by Georgetown University Medical Center researchers suggests that BACE1 inhibitors may prevent long-term damage from traumatic brain injury (Loane, D. J., et al., *Nature Medicine* (2009) 15: 377-379).

A logical approach to reducing Aβ levels is to block the action of the secretases. The β-secretase enzyme (BACE) is responsible for cleaving APP and forms the amino-terminus of Aβ, initiating the amyloidogenic pathway. Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324]. BACE –/– mice also show no significant negative phenotypes, suggesting that disruption of BACE-mediated cleavage of APP does not produce additional undesired effects. Thus, compounds that reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

What is therefore needed in the art are new compounds that inhibit β-amyloid peptide (Aβ) production, as well as compositions containing these compounds, and methods of treatment which utilize these compounds.

SUMMARY OF THE INVENTION

In its first aspect the present invention provides a compound of formula (I), including pharmaceutically acceptable salts thereof:

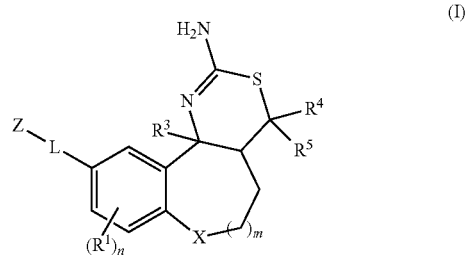

(I)

wherein X is selected from the group of $CH_2$, O, and $NR^2$;
m=0 or 1;
n=0 to 3;
$R^1$ at each instance is selected from the group of halogen, hydroxy, amino, $C_{1-4}$alkylamino, $C_{1-4}$ dialkylamino, halo$C_{1-4}$ alkyl, CN, $C_1$-$C_6$ alkyl or cycloalkyl, $C_1$-$C_6$ alkoxy, or $C_2$-$C_4$ alkynyl;
L is a bond, —NHCO—, —NH—, or L and Z together can be absent;
Z is a $C_6$-$C_{10}$-aryl group or a 5-10 membered heterocyclic group which can be further substituted with from 0-3 substituents selected from halogen, halo$C_{1-4}$ alkoxy, 4-methoxyphenyl, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl;
$R^2$ is selected from the group of hydrogen, benzyl, $C_1$-$C_6$ alkyl or cycloalkyl, $C_1$-$C_6$ alkoxy, acetyl, and methanesulfonyl;
and $R^3$, $R^4$ and $R^5$ are each independently selected from hydrogen or $C_{1-4}$alkyl.

In a second aspect, the present invention provides a pharmaceutical composition for the treatment of disorders responsive to the reduction of β-amyloid peptide production comprising a therapeutically effective amount of a compound of formula (I), or a pharmaceutically acceptable salt thereof, in association with a pharmaceutically acceptable carrier or diluent.

In a third aspect, the present invention provides a method for the treatment of disorders responsive to the reduction of β-amyloid peptide production in a mammal in need thereof, which comprises administering to said mammal a therapeutically effective amount of a compound of formula (I), or a pharmaceutically acceptable salt thereof. In a first embodiment of the third aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the third aspect, said disorder is selected from Alzheimer's Disease and Down Syndrome. In a third embodiment of the third aspect, said disorder is Alzheimer's Disease.

Other aspects of the present invention may include suitable combinations of embodiments disclosed herein.

Yet other aspects and embodiments may be found in the description provided herein.

DETAILED DESCRIPTION OF THE EMBODIMENTS

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

In some instances, the number of carbon atoms in any particular group is denoted before the recitation of the group. For example, the term "halo$C_{1-6}$alkoxy" denotes a haloalkoxy group containing one to six carbon atoms and the term "$C_{1-4}$alkoxy$C_{1-2}$alkyl" denotes an alkoxy group containing one to four alkoxy groups attached to the parent molecular moiety through an alkyl group of one or two carbon atoms. Where these designations exist they supersede all other definitions contained herein.

As used herein and unless otherwise expressly set forth elsewhere in the application, the following terms shall have the following meanings:

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "alkylsulfonylamido," as used herein refers to —C(O)NHS(O)$_2$R$^x$ wherein R$^x$ is an alkyl group.

The term "amino," as used herein, refers to —NH$_2$.

The term "carbonyl," as used herein, refers to —C(O)—.

The term "cyano," as used herein, refers to —CN.

The term "cycloalkyl," as used herein, refers to a saturated monocyclic hydrocarbon ring system having three to fourteen carbon atoms and zero heteroatoms.

The term "(cycloalkyl)alkyl," as used herein, refers to an alkyl group substituted with one, two, or three cycloalkyl groups.

The term "cycloalkylamino," as used herein, refers to —NHR$^x$ wherein Rx is a cycloalkyl group.

The term "cycloalkylcarbonyl," as used herein, refers to a cycloalkyl group attached to the parent molecular moiety through a carbonyl group.

The term "cycloalkylsulfonyl," as used herein, refers to a cycloalkyl group attached to the parent molecular moiety through a sulfonyl group.

The term "dialkylamino," as used herein, refers to —NR$^x$R$^y$, wherein R$^x$ and R$^y$ are each alkyl groups.

The term "dialkylaminoalkoxy," as used herein, refers to a dialkylamino group attached to the parent molecular moiety through an alkoxy group.

The term "dialkylaminoalkyl," as used herein, refers to an alkyl group substituted with one, two, or three dialkylamino groups.

The term "dialkylaminoalkylcarbonyl," as used herein, refers to a dialkylaminoalkyl group attached to the parent molecular moiety through a carbonyl group.

The term "H" as used herein, refers to hydrogen, including its isotopes.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "hydroxy," as used herein, refers to —OH.

The term "hydroxyalkyl," as used herein, refers to an alkyl group substituted with one, two, or three hydroxy groups.

The term "methylamino," as used herein, refers to —NHCH$_3$.

The term "oxo," as used herein, refers to =O.

The term "sulfonyl," as used herein, refers to —SO$_2$—.

It should be understood that the disclosure encompasses all stereochemical forms, or mixtures thereof, which possess the ability to reduce β-amyloid peptide production.

Certain compounds of the present invention may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Certain compounds of the present invention may exist in zwitterionic form and the present disclosure includes each zwitterionic form of these compounds and mixtures thereof.

The compounds of the present invention can exist as pharmaceutically acceptable salts. The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine Other representative organic amines useful for the formation of base addition salts include ethylenediamine, ethanolamine, diethanolamine, piperidine, and piperazine.

As set forth above, the present invention provides a compound of formula (I), including pharmaceutically acceptable salts thereof:

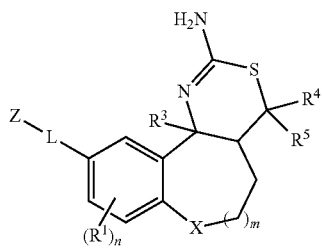

(I)

wherein X is selected from the group of $CH_2$, O, and $NR^2$;
m=0 or 1;
n=0 to 3;
$R^1$ at each instance is selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl;
L is a bond, —NHCO—, —NH—, or L and Z together can be absent;
Z is a $C_6$-$C_{10}$-aryl group or a 5-10 membered heterocyclic group which can be further substituted with from 0-3 substituents selected from halogen, halo$C_{1-4}$ alkoxy, 4-methoxyphenyl, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl;
$R^2$ is selected from the group of hydrogen, benzyl, $C_1$-$C_6$ alkyl or cycloalkyl, $C_1$-$C_6$ alkoxy, acetyl, and methanesulfonyl;
and $R^3$, $R^4$ and $R^5$ are each independently selected from hydrogen or $C_{1-4}$alkyl.

Also preferred are compounds of formula (I) wherein X is selected from $CH_2$ and O; m=0 or 1; n=0 to 3; $R^1$ at each instance is selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl; L is either a bond or is —NHCO—; Z is a phenyl, pyridyl, pyrimidinyl, or pyrazinyl group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, and $C_2$-$C_4$ alkynyl; and $R^3$, $R^4$ and $R^5$ are independently selected from hydrogen or $C_{1-4}$alkyl.

It is further preferred that X is selected from $CH_2$ and O; m=0 or 1; n=0 to 3; $R^1$ at each instance is selected from halogen; L is either a bond or is —NHCO—; Z is a phenyl, pyridyl, pyrimidinyl, or pyrazinyl group which can be further substituted with from 0-3 substituents selected from halogen, CN, or $C_2$-$C_4$ alkynyl; $R^3$ is selected from hydrogen or $C_{1-4}$alkyl; and $R^4$ and $R^5$ are hydrogen.

Also preferred are compounds of formula (I) wherein the configuration of the chiral center adjacent to the nitrogen of the aminothiazine is (S) or a pharmaceutically acceptable salt thereof.

One example of a preferred compound of the invention is 5-Chloro-pyridine-2-carboxylic acid ((4aS,11bS)-2-amino-11b-methyl-4,4a,5,6,7,11b-hexahydro-3-thia-1-aza-dibenzo[a,c]cyclohepten-10-yl)-amide.

Other especially preferred compounds of the invention, including pharmaceutically acceptable salts thereof, include the following:
(4aS,11bS)-10-Pyrimidin-5-yl-4,4a,5,6,7,11b-hexahydro-3-thia-1-aza-dibenzo[a,c]cyclohepten-2-ylamine;
rel-(4aS,11bS)-11b-Methyl-10-pyrimidin-5-yl-4,4a,5,6,7,11b-hexahydro-3-thia-1-aza-dibenzo[a,c]cyclohepten-2-ylamine, bis(2,2,2-trifluoroacetate);
(E)-Methyl 2-(5-chloropicolinamido)-9-methyl-6,7-dihydro-5H-benzo[7]annulene-8-carboxylate;
rel-(4aS,10bS)-10b-Methyl-9-(pyrimidin-5-yl)-4a,5,6,10b-tetrahydro-4H-naphtho[1,2-d][1,3]thiazin-2-amine, bis(2,2,2-trifluoroacetate);
rel-(4aS,10bS)-9-(5-Chloropyridin-3-yl)-10b-methyl-4a,5,6,10b-tetrahydro-4H-naphtho[1,2-d][1,3]thiazin-2-amine bis(2,2,2-trifluoroacetate);
N-((4aS,10bS)-2-Amino-10b-methyl-4a,5,6,10b-tetrahydro-4H-naphtho[1,2-d][1,3]thiazin-9-yl)-5-chloropicolinamide;
rel-N-((4aS,10bS)-2-Amino-10b-methyl-4a,5,6,10b-tetrahydro-4H-naphtho[1,2-d][1,3]thiazin-9-yl)-3,5-difluoropicolinamide, 2,2,2-trifluoroacetate;
rel-N-((4aS,10bS)-2-amino-10b-methyl-4a,5,6,10b-tetrahydro-4H-naphtho[1,2-d][1,3]thiazin-9-yl)-5-fluoropicolinamide, 2,2,2-trifluoroacetate;
rel-(4aS,11bS)-10-(5-methoxypyridin-3-yl)-11b-methyl-4,4a,5,6,7,11b-hexahydrobenzo[6,7]cyclohepta[1,2-d][1,3]thiazin-2-amine, bis(2,2,2-trifluoroacetate);
rel-(4aS,11bS)-10-(3-methoxyphenyl)-11b-methyl-4,4a,5,6,7,11b-hexahydrobenzo[6,7]cyclohepta[1,2-d][1,3]thiazin-2-amine, 2,2,2-trifluoroacetate;
rel-(4aS,11bS)-10-(5-Chloropyridin-3-yl)-11b-methyl-4,4a,5,6,7,11b-hexahydrobenzo[6,7]cyclohepta[1,2-d][1,3]thiazin-2-amine, bis(2,2,2-trifluoroacetate);
rel-(4aS,11bS)-10-(5-fluoropyridin-3-yl)-11b-methyl-4,4a,5,6,7,11b-hexahydrobenzo[6,7]cyclohepta[1,2-d][1,3]thiazin-2-amine, bis(2,2,2-trifluoroacetate);
rel-(4aS,11bS)-11b-Methyl-10-(5-(prop-1-yn-1-yl)pyridin-3-yl)-4,4a,5,6,7,11b-hexahydrobenzo[6,7]cyclohepta[1,2-d][1,3]thiazin-2-amine, bis(2,2,2-trifluoroacetate);
rel-(4aS,11bS)-11b-Methyl-10-(5-(prop-1-yn-1-yl)pyridin-3-yl)-4,4a,5,6,7,11b-hexahydrobenzo[6,7]cyclohepta[1,2-d][1,3]thiazin-2-amine, bis(2,2,2-trifluoroacetate);
rel-(4aR,10bS)-8-Fluoro-10b-methyl-9-(pyrimidin-5-yl)-4,4a,5,10b-tetrahydrochromeno[4,3-d][1,3]thiazin-2-amine, bis(2,2,2-trifluoroacetate);
rel-(4aS,10bS)-10b-methyl-9-(5-(prop-1-yn-1-yl)pyridin-3-yl)-4a,5,6,10b-tetrahydro-4H-naphtho[1,2-d][1,3]thiazin-2-amine, bis(2,2,2-trifluoroacetate);
(4aS,11bS)-11b-Methyl-10-(5-(prop-1-yn-1-yl)pyridin-3-yl)-4a,5,6,11b-tetrahydro-4H-benzo[2,3]oxepino[4,5-d][1,3]thiazin-2-amine;
rel-(4aS,11bS)-11b-Methyl-10-(1-methyl-1H-pyrazol-4-yl)-4a,5,6,11b-tetrahydro-4H-benzo[2,3]oxepino[4,5-d][1,3]thiazin-2-amine, bis(2,2,2-trifluoroacetate);
(4aS,11bS)-11b-Methyl-10-(2-methylthiazol-5-yl)-4a,5,6,11b-tetrahydro-4H-benzo[2,3]oxepino[4,5-d][1,3]thiazin-2-amine;
rel-(4aS,11bS)-11b-methyl-10-(pyrimidin-5-yl)-4a,5,6,11b-tetrahydro-4H-benzo[2,3]oxepino[4,5-d][1,3]thiazin-2-amine, bis(2,2,2-trifluoroacetate);
rel-(4aS,11bS)-10-(isoquinolin-4-yl)-11b-methyl-4a,5,6,11b-tetrahydro-4H-benzo[2,3]oxepino[4,5-d][1,3]thiazin-2-amine, bis(2,2,2-trifluoroacetate);
N-((4aS,11bS)-2-amino-11b-methyl-4a,5,6,11b-tetrahydro-4H-benzo[2,3]oxepino[4,5-d][1,3]thiazin-10-yl)-5-chloropicolinamide;

N-((4aS,11bS)-2-Amino-11b-methyl-4a,5,6,11b-tetrahydro-4H-benzo[2,3]oxepino[4,5-d][1,3]thiazin-10-yl)-3,5-dichloropicolinamide;

N-((4aS,11bS)-2-amino-11b-methyl-4a,5,6,11b-tetrahydro-4H-benzo[2,3]oxepino[4,5-d][1,3]thiazin-10-yl)-5-cyanopicolinamide;

N-((4aS,11bS)-2-Amino-11b-methyl-4a,5,6,11b-tetrahydro-4H-benzo[2,3]oxepino[4,5-d][1,3]thiazin-10-yl)-5-fluoropicolinamide;

rel-(4aS,11bS)—N10-(3-Chloropyridin-2-yl)-11b-methyl-4a,5,6,11b-tetrahydro-4H-benzo[2,3]oxepino[4,5-d][1,3]thiazine-2,10-diamine, bis(2,2,2-trifluoroacetate);

rel-(4aS,11bS)—N10-(3-Methoxypyridin-2-yl)-11b-methyl-4a,5,6,11b-tetrahydro-4H-benzo[2,3]oxepino[4,5-d][1,3]thiazine-2,10-diamine, bis(2,2,2-trifluoroacetate);

rel-(4aS,11bS)—N10-(4-Methoxypyrimidin-2-yl)-11b-methyl-4a,5,6,11b-tetrahydro-4H-benzo[2,3]oxepino[4,5-d][1,3]thiazine-2,10-diamine, bis(2,2,2-trifluoroacetate);

N-((4aS,11bS)-2-Amino-11b-methyl-4,4a,5,6,7,11b-hexahydrobenzo[6,7]cyclohepta[1,2-d][1,3]thiazin-10-yl)-5-fluoropicolinamide;

N-((4aS,11bS)-2-Amino-11b-methyl-4,4a,5,6,7,11b-hexahydrobenzo[6,7]cyclohepta[1,2-d][1,3]thiazin-10-yl)-5-cyanopicolinamide;

N-((4aS,11bS)-2-Amino-11b-methyl-4,4a,5,6,7,11b-hexahydrobenzo[6,7]cyclohepta[1,2-d][1,3]thiazin-10-yl)-3,5-dichloropicolinamide;

N-((4aS,11bS)-2-Amino-11b-methyl-4,4a,5,6,7,11b-hexahydrobenzo[6,7]cyclohepta[1,2-d][1,3]thiazin-10-yl)-5-(difluoromethoxy)picolinamide; and rel-(4aS,11bS)-9-fluoro-11b-methyl-10-(pyrimidin-5-yl)-4,4a,5,6,7,11b-hexahydrobenzo[6,7]cyclohepta[1,2-d][1,3]thiazin-2-amine, bis(2,2,2-trifluoroacetate).

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), or a pharmaceutically acceptable salt thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of β-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phosphatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present invention will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "dba" for dibenzylideneacetone; "t-Bu" for tert-butyl; "DCM" for dichloromethane; "DIEA" for N,N-diisopropylethylamine; "LDA" for lithium diisopropylamide; "Ph" for phenyl; "TFA" for trifluoroacetic acid; "Et" for ethyl; "DMF" for N,N-dimethylformamide; "OAc" for acetate; "h" for hours, "min" for minutes; and "THF" for tetrahydrofuran.

A general synthesis of one class of the compounds of claim 1 is presented below in Scheme 1. 3-bromobenzocycloheptanones 1 can be acylated under basic conditions with dimethyl carbonate to form the beta-ketoesters 2. Reduction with sodium borohydride or other reducing agents produces the alcohols 3, which eliminate under acidic conditions forming the α,β unsaturated esters 4. Reduction of the ester followed by halogenation of the resulting alcohol leads to the allylic chlorides 6, which can be condensed with thiourea followed by acidic cyclization to prepare the aminothiazines 7. Following protection of the aminothiazine using standard conditions including preparation of the bis-boc protected intermediate, the core can undergo a number of reactions to functionalize the 3-bromo group. These include palladium-catalyzed coupling reactions to install aryl or vinyl groups, or copper- and palladium-catalyzed reactions that install N-linked heterocycles or aminoheterocycles. Final deprotection of the protected compounds using acids including TFA provides the title compounds of claim I.

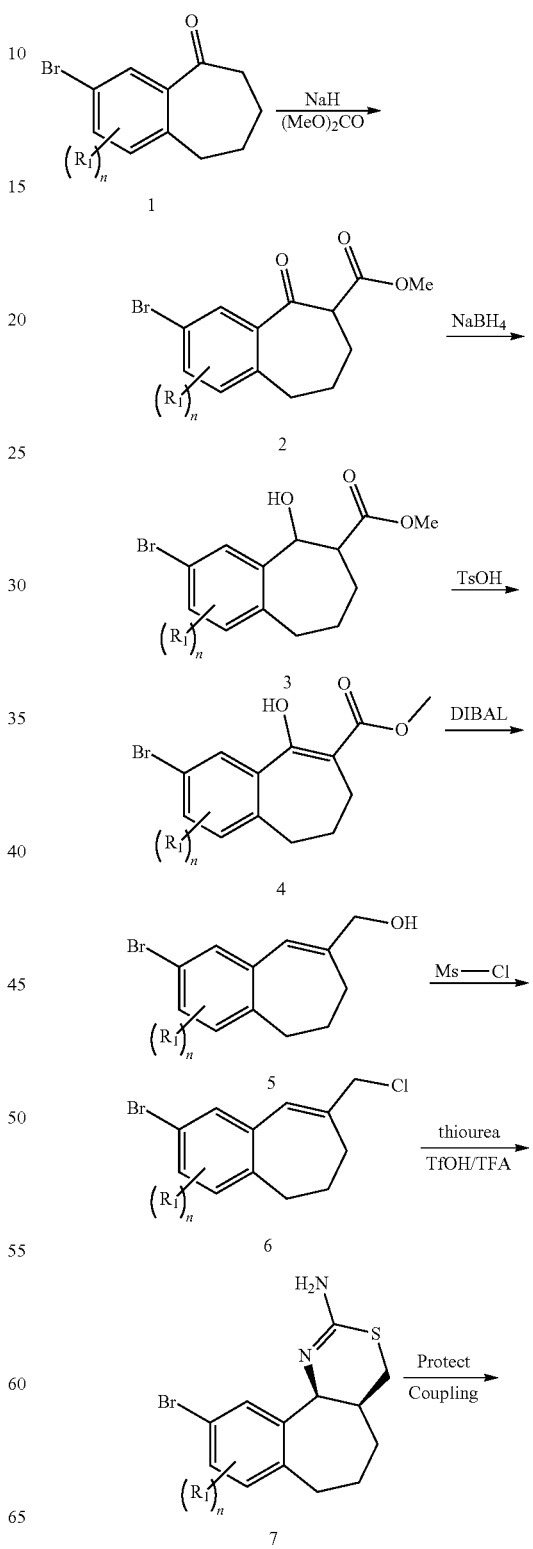

SCHEME 1

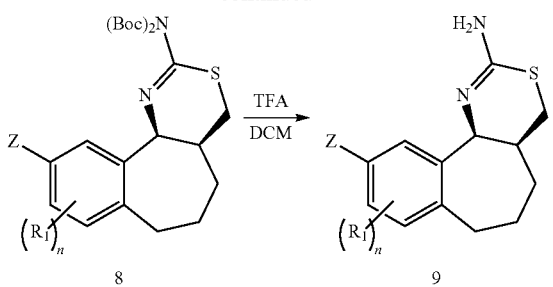

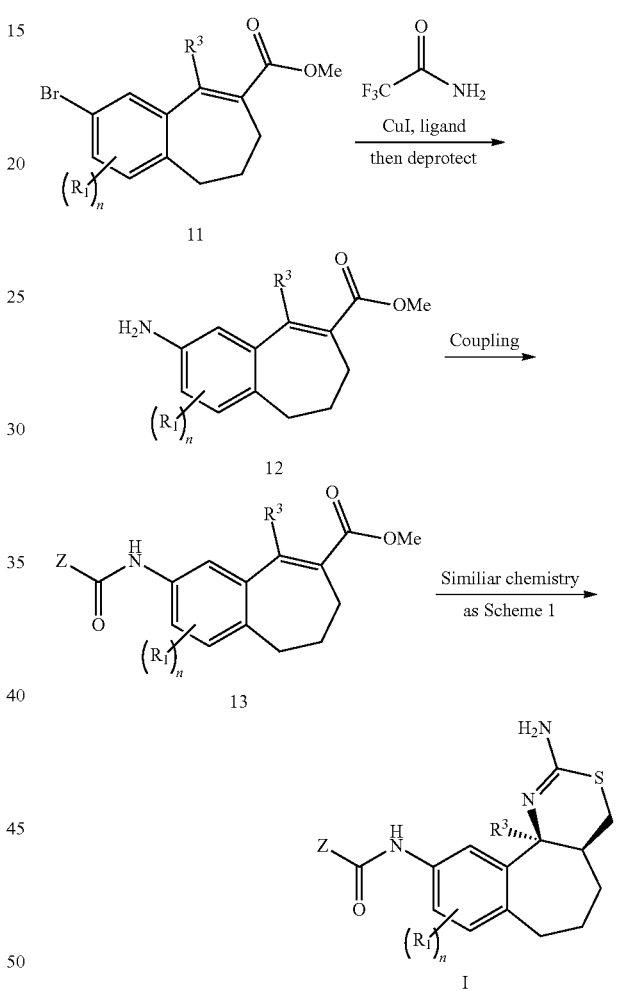

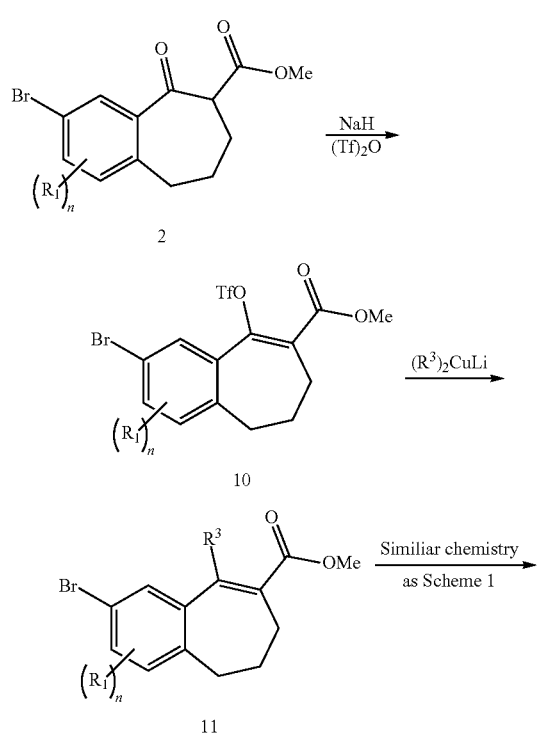

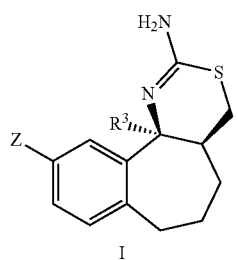

In one useful variant of the chemistry presented in Scheme 1, intermediates 2 can be reacted with triflic anhydride under basic conditions to yield the vinyl triflates (Scheme 2). These intermediates react with lithiocuprates including dimethyl cuprate to produce the beta-methyl enones 11. These intermediates can then be carried through chemistry analogous to that shown in scheme 1 to provide additional analogs of claim I retaining the additional alkyl group.

In one useful variant of the chemistry presented in Scheme 1, the bromine atom on intermediates 11 (or the corresponding dimethyl intermediates 4) is replaced with a N-trifluoroacetamide group (Scheme 3). The trifluoroacetamide group is then easily deprotected under mild basic conditions to reveal the aniline. The anilines 12 serve as precursors for coupling reactions known to those skilled in the art, including condensation with carboxylic acids or acid equivalents to make amides (13), or similar reactions with sulfonyl chlorides to make sulfonamides, or isocyanates to make ureas. Deprotection of the coupled intermediates then provides the desired compounds of claim I.

Additional compounds of the invention can be made using the chemistry described in scheme 4. Bromination of phenols 14 produces intermediates of type 15, which can be alkylated by homoallyl bromide to produce intermediates 16. Suzuki coupling under standard conditions can introduce a variety of aryl groups at the bromide position, here pyrimidinyl boronic acid is used as one such example. Additional known copper-based chemistry can couple primary amides through the amide nitrogen atom to the same position, including the reaction sequence demonstrated in scheme 3. Cyclization of the resulting intermediates 17 results in formation of the products 18 which represent an additional class of compounds of formula I.

SCHEME 4

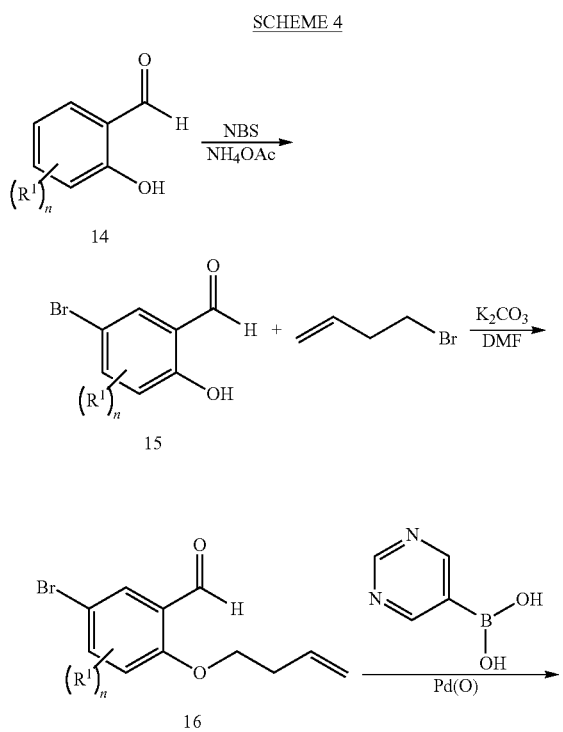

SCHEME 5

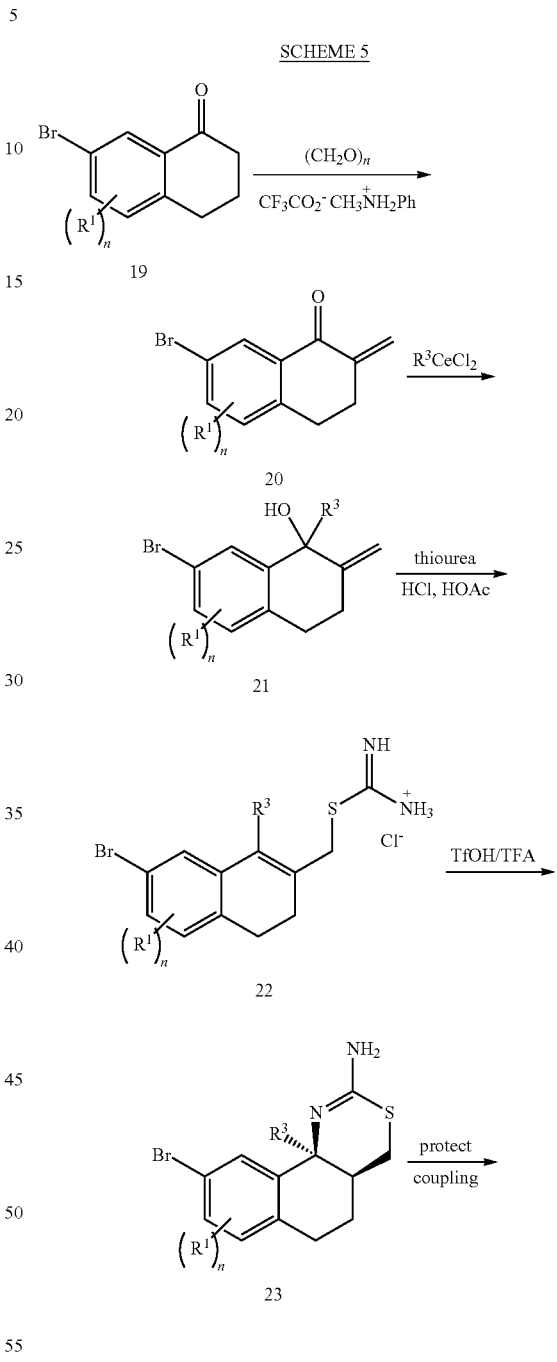

to those skilled in the art, including the sequence shown in scheme 3, provides the coupled products 24. Deprotection then provides additional products of claim I.

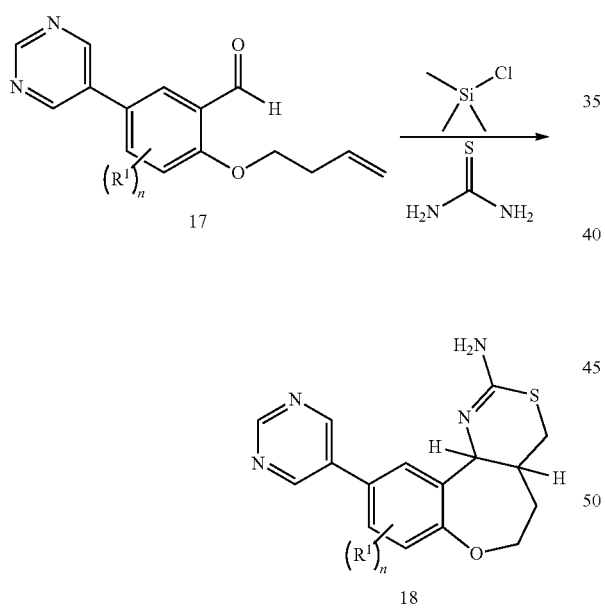

Further compounds of claim I can be prepared as is shown in scheme 5. Substituted tetralones 19 can be reacted with paraformaldehyde to create the exocyclic enones 20. Reaction with methyl cerium dichloride or other alkyl metals produces alcohols 21. Acidic condensation with thiourea proceeds in a Michael (1,4-addition) sense to create the S-linked precursors 22. Cyclization with triflic acid in trifluoroacetic acid provides the tricyclic aminothiazine 23. The free amino group is then protected, and coupling of aryl boronic acids, amides, or additional reagents according to techniques known -continued

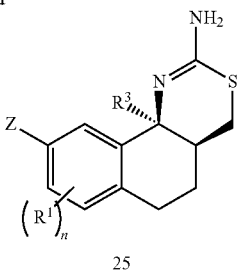

"HPLC" is an abbreviation used herein for high pressure liquid chromatography. When described as performed under "standard conditions", samples were dissolved in methanol (1 mg/mL) and run using a gradient program with a solvent flow rate of 1.0 mL/min. Reverse phase preparatory HPLC: When described as performed under "standard conditions", samples (approx. 20 mg) were dissolved in methanol (10 mg/mL) and purified on a 30 mm×100 mm Waters-Atlantis S5 column using a 10 minute gradient elution from 0% to 100% buffer B in buffer A (buffer A=10% $CH_3OH$/90% water/0.1% TFA and buffer B=90% MeOH/10% water/0.1% TFA).at 40 mL/minute. "MS" refers to mass spectrometry data collected on a high pressure liquid chromatography system with a mass spectrometry detector, and are typically collected using electrospray ionization. "TLC" is an abbreviation used herein for thin layer chromatography. Proton NMR spectra were obtained on a Bruker 400 or 500 spectrometer. Data were referred to the lock solvent.

The examples provided are intended to assist in a further understanding of the present invention. Particular materials employed, species and conditions are intended to further illustrate the specific embodiments of the invention and not limit the reasonable scope thereof.

SYNTHESIS OF INTERMEDIATES

Preparation A rel-(4aS,11bS)-10-Bromo-4,4a,5,6,7,11b-hexahydro-3-thia-1-aza-dibenzo[a,c]cyclohepten-2-ylamine, bis-N,N-(tert-butyl)carbamate

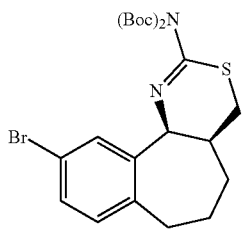

Step A1. 3-Bromo-6,7,8,9-tetrahydro-5H-benzo[7]annulen-5-one

A 3-neck 250 mL flask fitted with a condenser was charged with aluminum trichloride (45.0 g, 337 mmol) which was then heated to 75° C. under nitrogen. 6,7,8,9-Tetrahydro-5H-benzo[7]annulen-5-one (20.0 g, 125 mmol) was added slowly dropwise via additional funnel. After complete addition, a dark brown slurry was formed. After stirring for 20 min, bromine (8.36 ml, 162 mmol) was added dropwise very slowly at 75° C., and the reaction mixture was stirred at 75° C. for an additional 20 min. The hot mixture was slowly poured into 400 g of ice and 30 mL of concentrated HCl. The resulting mixture was stirred for 30 min, then extracted with diethyl ether (3×400 mL). The ethereal extract was concentrated and the residue was purified using silica gel column chromatography (hexanes-10% EtOAc) to afford 3-bromo-6,7,8,9-tetrahydro-5H-benzo[7]annulen-5-one (8.3 g, 28%). $^1$H NMR (500 MHz, chloroform-d) δ 7.86 (d, J=2.1 Hz, 1H), 7.54 (dd, J=8.2, 2.1 Hz, 1H), 7.10 (d, J=8.2 Hz, 1H), 2.94-2.88 (m, 2H), 2.80-2.72 (m, 2H), 1.94-1.80 (m, 4H).

Step A2. Methyl 3-bromo-5-oxo-6,7,8,9-tetrahydro-5H-benzo[7]annulene-6-carboxylate To a solution of 3-bromo-6,7,8,9-tetrahydro-5H-benzo[7]annulen-5-one from step A1 (600 mg, 2.51 mmol) in neat dimethyl carbonate (2.81 mL, 33.3 mmol) was slowly added 60% NaH dispersed in mineral oil (251 mg, 6.27 mmol). The mixture was stirred at 85° C. for 3 h, then cooled to rt, treated with 1 N HCl (40 mL), and extracted with EtOAc (2×50 mL). The combined organic layers were dried over sodium sulfate, filtered, and concentrated in vacuo to afford crude methyl 3-bromo-5-oxo-6,7,8,9-tetrahydro-5H-benzo[7]annulene-6-carboxylate (800 mg, 2.69 mmol, 107% yield), which was used for the next step without purification. LCMS $(M+H)^+=297.2$. $^1$H NMR (500 MHz, chloroform-d) δ 12.56 (s, 1H), 7.78 (d, J=2.1 Hz, 1H), 7.47 (dd, J=8.2, 2.1 Hz, 1H), 7.12 (d, J=7.9 Hz, 1H), 3.86 (s, 3H), 2.61 (t, J=6.9 Hz, 2H), 2.18-2.05 (m, 4H).

Step A3. Methyl 3-bromo-5-hydroxy-6,7,8,9-tetrahydro-5H-benzo[7]annulene-6-carboxylate To a solution of the crude methyl 3-bromo-5-oxo-6,7,8,9-tetrahydro-5H-benzo[7]annulene-6-carboxylate from step A2 (350 mg, 1.18 mmol) in MeOH (5 mL) was slowly added $NaBH_4$ (44.6 mg, 1.18 mmol) at 0° C. The mixture was stirred at 0° C. for 30 min. The solvent was removed in vacuo at rt. EtOAc (100 mL) was added and the organic layer was washed with water. The organic layer was concentrated, and the residue was purified using silica gel column chromatography (hexanes-60% EtOAc) to give methyl 3-bromo-5-hydroxy-6,7,8,9-tetrahydro-5H-benzo[7]annulene-6-carboxylate (230 mg, 0.769 mmol, 65% yield). $^1$H NMR (500 MHz, chloroform-d) δ 7.81-7.39 (m, 1H), 7.35-7.23 (m, 1H), 7.01-6.87 (m, 1H), 5.13-4.96 (m, 1H), 3.77-3.65 (m, 3H), 3.39-3.22 (m, 1H), 3.20-2.56 (m, 3H), 2.47-1.86 (m, 3H), 1.65-1.30 (m, 1H).

Step A4. (E)-Methyl 2-bromo-6,7-dihydro-5H-benzo[7]annulene-8-carboxylate

To a solution of methyl 3-bromo-5-hydroxy-6,7,8,9-tetrahydro-5H-benzo[7]annulene-6-carboxylate from step A3 (230 mg, 0.769 mmol) in toluene (3 mL) was added p-toluenesulfonic acid monohydrate (29.2 mg, 0.154 mmol). The mixture was heated at reflux for 4 h. The solvent was removed in vacuo, and the residue was purified using silica gel column chromatography (hexanes-10% EtOAc) to give methyl 2-bromo-6,7-dihydro-5H-benzo[7]annulene-8-carboxylate (175 mg, 0.622 mmol, 81% yield). $^1$H NMR (500 MHz, chloroform-d) δ 7.61 (s, 1H), 7.44 (d, J=1.8 Hz, 1H), 7.32 (dd, J=8.1, 2.0 Hz, 1H), 7.02 (d, J=7.9 Hz, 1H), 3.83 (s, 3H), 2.79-2.72 (m, 2H), 2.63 (t, J=6.6 Hz, 2H), 2.09-2.00 (m, 2H).

Step A5. (E)-(2-Bromo-6,7-dihydro-5H-benzo[7]annulen-8-yl)methanol

To a solution of methyl 2-bromo-6,7-dihydro-5H-benzo[7]annulene-8-carboxylate from step A4 (170 mg, 0.605 mmol) in diethyl ether (2 mL) and THF (1 mL) was added 1.0 M DIBAL-H/hexanes (0.726 mL, 0.726 mmol) at −78° C. The mixture was stirred at rt for 16 h. Another 0.726 mL portion of DIBAL-H was added at 0° C., and the mixture was stirred at rt for an additional 2 h. The reaction mixture was diluted with 50 mL of diethyl ether, quenched with water, and extracted with EtOAc (100 mL). The organic layer was dried over sodium sulfate, filtered, and concentrated to give (2-bromo-6,7-dihydro-5H-benzo[7]annulen-8-yl)methanol (150 mg, 0.593 mmol, 98% yield). $^1$H NMR (500 MHz, chloroform-d) δ 7.30 (s, 1H), 7.22 (dd, J=7.9, 1.8 Hz, 1H), 6.98 (d, J=7.9 Hz, 1H), 6.45 (s, 1H), 4.21 (br. s., 2H), 2.81-2.71 (m, 2H), 2.34 (t, J=6.4 Hz, 2H), 2.08-1.98 (m, 2H).

Step A6. (E)-2-Bromo-8-(chloromethyl)-6,7-dihydro-5H-benzo[7]annulene

To a solution of (2-bromo-6,7-dihydro-5H-benzo[7]annulen-8-yl)methanol from step A5 (150 mg, 0.593 mmol) in dichloromethane (2 mL) was added DIEA (0.310 mL, 1.78 mmol) followed by methanesulfonyl chloride (0.053 mL, 0.681 mmol) at 0° C. The mixture was gradually warmed up to rt and stirred for 18 h. Diethyl ether (50 mL) was added, the mixture was washed with water, the organic layer was partioned and concentrated. The residue was purified using silica gel column chromatography (hexanes-10% EtOAc) to give 2-bromo-8-(chloromethyl)-6,7-dihydro-5H-benzo[7]annulene (135 mg, 0.497 mmol, 84% yield). $^1$H NMR (500 MHz, chloroform-d) δ 7.31-7.29 (m, 1H), 7.26 (dd, J=8.2, 1.8 Hz, 1H), 7.00 (d, J=7.9 Hz, 1H), 6.51 (s, 1H), 4.21 (s, 2H), 2.80-2.74 (m, 2H), 2.48 (t, J=6.7 Hz, 2H), 2.10-2.02 (m, 2H).

Step A7. rel-(4aS,11bS)-10-Bromo-4,4a,5,6,7,11b-hexahydro-3-thia-1-aza-dibenzo[a,c]cyclohepten-2-ylamine To a solution of 2-bromo-8-(chloromethyl)-6,7-dihydro-5H-benzo[7]annulene from step A6 (60 mg, 0.221 mmol) in ethanol (1 mL) was added thiourea (16.82 mg, 0.221 mmol). The mixture was heated at reflux for 4 h. The solvent was removed, and the solid residue was triturated with hexanes and dried in vacuo to give (2-bromo-6,7-dihydro-5H-benzo[7]annulen-8-yl)methyl carbamimidothioate hydrochloride (70 mg, 0.201 mmol, 91% yield). To a solution of (2-bromo-6,7-dihydro-5H-benzo[7]annulen-8-yl)methyl carbamimidothioate, hydrochloride (60 mg, 0.173 mmol) in TFA (1 mL) was added triflic acid (0.2 mL) at 0° C. The mixture was stirred at rt for 18 h and then heated to 80° C. for 4 h. Another 2 mL of TFA and 0.2 mL of trifilic acid were added, and the mixture was stirred at 60° C. for 20 h. The solvent was removed. The residue was dissolved in 50 mL of EtOAc and the organic layer was washed with saturated sodium bicarbonate/water, dried over sodium sulfate, filtered, and concentrated in vacuo to afford crude product (60 mg, 0.193 mmol, 112% yield), which was used for the next step without purification.

Step A8. rel-(4aS,11bS)-10-Bromo-4,4a,5,6,7,11b-hexahydro-3-thia-1-aza-dibenzo[a,c]cyclohepten-2-ylamine, bis-N,N-(tert-butyl)carbamate To the crude product of step A7 (60 mg, 0.193 mmol) in acetonitrile (1 mL) was added DMAP (18 mg, 0.147 mmol) and di-tert-butyl dicarbonate (0.340 mL, 1.47 mmol). The mixture was stirred at rt for 20 h. The solvent was removed, and the residue was purified using silica gel column chromatography (hexanes-100% EtOAc) to give the titled compound of preparation A (22 mg, 0.043 mmol, 22% yield). LCMS (M+H)$^+$=513.3. $^1$H NMR (500 MHz, chloroform-d) δ 7.55 (d, J=1.8 Hz, 1H), 7.35 (dd, J=7.9, 1.8 Hz, 1H), 7.00 (d, J=7.9 Hz, 1H), 5.70 (br. s., 1H), 2.89-2.76 (m, 3H), 2.66-2.58 (m, 3H), 1.98-1.77 (m, 3H), 1.56 (s, 9H), 1.41 (s, 9H).

Preparation B rel-(4aS,11bS)-10-Bromo-11b-methyl-4,4a,5,6,7,11b-hexahydro-3-thia-1-aza-dibenzo[a,c]cyclohepten-2-ylamine, bis-N,N-(tert-butyl)carbamate

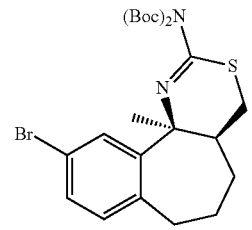

Step B1. (Z)-Methyl 2-bromo-9-(trifluoromethylsulfonyloxy)-6,7-dihydro-5H-benzo[7]annulene-8-carboxylate To a solution of the crude methyl 3-bromo-5-oxo-6,7,8,9-tetrahydro-5H-benzo[7]annulene-6-carboxylate from step A2 (150 mg, 0.505 mmol) in DME (3 mL) was slowly added 60% NaH (20.2 mg, 0.505 mmol) at 0° C. After stirring for 10 min, trifluoromethanesulfonic anhydride (0.111 mL, 0.656 mmol) was added. The mixture was stirred at rt for 2 h. The reaction mixture was diluted with 50 mL of diethyl ether, and the organic layer was washed with saturated aqueous sodium bicarbonate and water. The organic layer was separated and concentrated. The residue was purified by silica gel column chromatography (hexanes-10% EtOAc) to give (Z)-methyl 2-bromo-9-(trifluoromethylsulfonyloxy)-6,7-dihydro-5H-benzo[7]annulene-8-carboxylate (52 mg, 0.121 mmol, 24% yield). $^1$H NMR (500 MHz, chloroform-d) δ 7.61 (d, J=1.8 Hz, 1H), 7.53 (dd, J=8.1, 2.0 Hz, 1H), 7.18 (d, J=7.9 Hz, 1H), 3.92 (s, 3H), 2.70 (t, J=6.9 Hz, 2H), 2.32-2.24 (m, 4H).

Step B2. (E)-Methyl 2-bromo-9-methyl-6,7-dihydro-5H-benzo[7]annulene-8-carboxylate To a suspension of CuI (760 mg, 4.0 mmol) in anhydrous diethyl ether (5 mL) was dropwise added a 1.6 M solution of methyllithium (8 mmol, 5 mL) in an ice-salt bath (−10° C.). After stirring for 20 min, a homogeneous 0.4 M (Me)$_2$CuLi solution was ready for use. To a solution of (Z)-methyl 2-bromo-9-(trifluoromethylsulfonyloxy)-6,7-dihydro-5H-benzo[7]annulene-8-carboxylate from step B1 (52 mg, 0.121 mmol) in diethyl ether (0.5 mL) was dropwise added the above Me$_2$CuLi solution (0.727 mmol, 1.82 mL) at −78° C. The mixture was stirred from −78° C. to −40° C. over 2 h. The reaction mixture was then quenched with 10 mL of water, and the mixture was extracted with diethyl ether (3×15 mL). The combined organic layers were dried over sodium sulfate, filtered, and concentrated in vacuo to give (E)-methyl 2-bromo-9-methyl-6,7-dihydro-5H-benzo[7]annulene-8-carboxylate (38 mg, 0.129 mmol, 106% yield). The material was used for the next step without purification. LCMS (M+H)+=297.0. $^1$H NMR (500 MHz, chloroform-d) δ 7.43 (d, J=1.8 Hz, 1H), 7.35 (dd, J=8.1, 2.0 Hz, 1H), 7.07 (d, J=8.2 Hz, 1H), 3.82 (s, 3H), 2.56-2.49 (m, 2H), 2.38 (s, 3H), 2.17-2.07 (m, 4H).

Step B3. (E)-(2-Bromo-9-methyl-6,7-dihydro-5H-benzo[7]annulen-8-yl)methanol

In a manner similar to the procedure of step A5, the compound of step B2 was converted to the compound of step B3 in 77% yield. $^1$H NMR (500 MHz, chloroform-d) δ 7.39 (d, J=1.8 Hz, 1H), 7.32-7.28 (m, 1H), 7.06 (d, J=7.9 Hz, 1H), 4.39 (s, 2H), 2.51 (t, J=7.2 Hz, 2H), 2.17-2.06 (m, 5H), 2.01-1.93 (m, 2H).

Step B4. (E)-2-Bromo-8-(chloromethyl)-9-methyl-6,7-dihydro-5H-benzo[7]annulene

In a manner similar to the procedure of step A6, the compound of step B3 was converted to the compound of step B4 in 84% yield. $^1$H NMR (500 MHz, chloroform-d) δ 7.38 (t, J=2.6 Hz, 1H), 7.33-7.27 (m, 1H), 7.06 (dd, J=7.9, 3.4 Hz, 1H), 4.34 (d, J=3.4 Hz, 2H), 2.53 (td, J=7.1, 3.2 Hz, 2H), 2.22-2.12 (m, 5H), 2.02-1.95 (m, 2H).

Step B5. rel-(4aS,11bS)-10-Bromo-11b-methyl-4,4a,5,6,7,11b-hexahydro-3-thia-1-aza-dibenzo[a,c]cyclohepten-2-ylamine, bis-N,N-(tert-butyl)carbamate In a manner similar to that reported for steps A7 and A8 the compound of step B4 was converted to the titled compound of preparation B. LCMS (M+H)+=527.1. $^1$H NMR (500 MHz, chloroform-d) δ 7.68 (d, J=2.1 Hz, 1H), 7.27 (dd, J=7.9, 2.1 Hz, 1H), 6.98 (d, J=7.9 Hz, 1H), 3.07-2.97 (m, 1H), 2.88 (dd, J=12.2, 10.7 Hz, 1H), 2.81 (dd, J=14.8, 5.0 Hz, 1H), 2.76-2.65 (m, 1H), 2.33-2.21 (m, 1H), 2.14 (ddt, J=8.0, 5.1, 2.7 Hz, 1H), 2.08-1.98 (m, 1H), 1.89-1.76 (m, 1H), 1.71 (s, 3H), 1.56 (s, 18H), 1.35-1.25 (m, 1H).

Preparation C tert-Butyl rel-(4aS,10bS)-9-bromo-10b-methyl-4a,5,6,10b-tetrahydro-4H-naphtho[1,2-d][1,3]thiazin-2-ylcarbamate

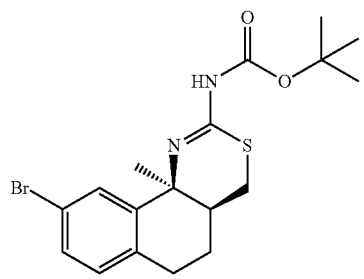 [SMILES: CC(C)(C)OC(=O)NC1=N[C@]2(C)c3cc(Br)ccc3CC[C@@H]2CS1]

Step C1. 7-Bromo-2-methylene-3,4-dihydronaphthalen-1(2H)-one

A solution of 7-bromo-3,4-dihydronaphthalen-1(2H)-one (2.00 g, 8.89 mmol) in THF (50 mL) was added to a mixture of N-methylanilinium trifluoroacetate (2.95 g, 13.3 mmol) and paraformaldehyde (1.20 g, 40.0 mmol) at rt. The resulting mixture was heated at reflux for 6 hours. The oil bath was removed and the mixture was allowed to cool to rt. Diethyl ether was added to the reaction mixture, which induced the separation of a red gum. The ethereal solution was decanted from the red gum into a separatory funnel and washed with half-saturated sodium bicarbonate solution. The red gum was triturated with diethyl ether, and the resulting ethereal solution was then used to extract the washing water. The combined organic layers were dried over magnesium sulfate. Filtration and concentration of the organic layer afforded a heavy red oil. The oil was purified using silica gel column chromatography (20:1 hexanes/EtOAc) to afford 7-bromo-2-methylene-3,4-dihydronaphthalen-1(2H)-one (0.850 g, 3.59 mmol, 40% yield) as a thick viscous yellow oil. $^1$H NMR (400 MHz, chloroform-d) δ 8.23 (d, J=2.0 Hz, 1H), 7.60 (dd, J=8.2, 2.1 Hz, 1H), 7.16 (d, J=8.3 Hz, 1H), 6.26 (q, J=1.3 Hz, 1H), 5.50 (q, J=1.7 Hz, 1H), 3.01-2.91 (m, 2H), 2.91-2.82 (m, 2H).

Step C2. 7-Bromo-1-methyl-2-methylene-1,2,3,4-tetrahydronaphthalen-1-ol

Anhydrous THF (200 mL) was added to a flame dried flask charged with anhydrous cerium (III) chloride (3.90 g, 15.8 mmol) under dry nitrogen. The mixture was vigorously stirred for 2 hours to provide an opaque suspension. The suspension was cooled to –78° C. Methyllithium (1.6 M in diethylether) (9.89 mL, 15.8 mmol) was added to the suspension of cerium(III) chloride to produce a bright yellow solution of methylcerium(III) dichloride. After stirring for 1 hour at –78° C., a solution of 7-bromo-2-methylene-3,4-dihydronaphthalen-1(2H)-one from step C1 (1.5 g, 6.33 mmol) in THF (20 mL) was added. The reaction mixture was allowed to stir for 30 min at –78° C., then it was poured into an Erlenmeyer flask charged with saturated aqueous ammonium chloride solution. The aqueous mixture was extracted with ethyl acetate. The combined organic layers were washed with brine, dried over sodium sulfate, filtered, and concentrated in vacuo. The residue was purified using silica gel column chromatography (10:1 Hex/EtOAc) to afford 7-bromo-1-methyl-2-methylene-1,2,3,4-tetrahydronaphthalen-1-ol (0.670 g, 2.66 mmol, 42% yield) as a clear viscous oil. $^1$H NMR (500 MHz, chloroform-d) δ 7.81 (d, J=2.0 Hz, 1H), 7.29 (dd, J=8.1, 2.1 Hz, 1H), 6.93 (d, J=8.1 Hz, 1H), 5.29-5.25 (m, 1H), 4.98 (d, J=1.2 Hz, 1H), 2.86-2.76 (m, 2H), 2.65-2.57 (m, 2H), 1.87-1.84 (m, 1H), 1.60 (s, 3H).

Step C3. (7-Bromo-1-methyl-3,4-dihydronaphthalen-2-yl)methyl carbamimidothioate, hydrochloride A 1.0 M solution of hydrochloric acid/acetic acid (5.93 mL, 5.93 mmol) was added to a stirred mixture of 7-bromo-1-methyl-2-methylene-1,2,3,4-tetrahydronaphthalen-1-ol from step C2 (1.0 g, 3.95 mmol) and thiourea (0.316 g, 4.15 mmol) in acetic acid (10 mL). The resulting mixture was capped and heated at 40° C. for 20 h. The mixture was cooled to rt and a solid slowly precipitated. After 4 h, the solid was collected using vacuum filtration. The solid was rinsed with EtOAc (150 mL) and dried under high vacuum to afford (7-bromo-1-methyl-3,4-dihydronaphthalen-2-yl)methyl carbamimidothioate, HCl (810 mg, 2.330 mmol, 59.0% yield) as a white solid. $^1$H NMR (500 MHz, methanol-$d_4$) δ 7.46 (d, J=2.0 Hz, 1H), 7.32 (dd, J=7.9, 2.0 Hz, 1H), 7.08 (d, J=7.9 Hz, 1H), 4.17 (s, 2H), 2.77-2.70 (m, 2H), 2.43-2.35 (m, 2H), 2.14 (t, J=1.5 Hz, 3H).

Step C4. tert-Butyl rel-(4aS,10bS)-9-bromo-10b-methyl-4a,5,6,10b-tetrahydro-4H-naphtho[1,2-d][1,3]thiazin-2-ylcarbamate Triflic acid (0.25 mL, 2.82 mmol) was added to flask charged with a stirred solution of (7-bromo-1-methyl-3,4-dihydronaphthalen-2-yl)methyl carbamimidothioate from step C3 (255 mg, 0.819 mmol) in TFA (2.5 mL) at 0° C. The resulting mixture was capped and left to stir at 0° C. for 2 h. The reaction contents were carefully added to a swirled mixture of ice and excess solid sodium bicarbonate. After gas evolution had ceased, the resulting mixture was extracted with EtOAc. The combined organic layers were washed with brine, dried over sodium sulfate, filtered, and concentrated in vacuo to afford rel-(4aS,10bR)-9-bromo-10b-methyl-4a,5,6,10b-tetrahydro-4H-naphtho[1,2-d][1,3]thiazin-2-amine as a white solid. The crude product was dissolved in THF (2.5 mL). Triethylamine (0.457 mL, 3.28 mmol), di-tert-butyl dicarbonate (0.571 mL, 2.458 mmol), and DMAP (5.00 mg, 0.041 mmol) were added to the crude product. After 16 h, the reaction mixture was concentrated in vacuo and purified using silica gel column chromatography (10:1 hexanes/EtOAc) to afford tert-butyl rel-((4aS,10bS)-9-bromo-10b-methyl-4a,5,6,10b-tetrahydro-4H-naphtho[1,2-d][1,3]thiazin-2-yl)carbamate (244 mg, 0.581 mmol, 71.0% yield) as a white solid. LCMS (M+H)$^+$=225.0. $^1$H NMR (500 MHz, chloroform-d) δ 7.61 (br. s., 1H), 7.32 (dd, J=8.2, 1.8 Hz, 1H), 6.98 (d, J=8.2 Hz, 1H), 3.04 (dd, J=12.9, 3.6 Hz, 1H), 2.88 (dd, J=13.0, 8.2 Hz, 1H), 2.83 (t, J=6.9 Hz, 2H), 2.36-2.20 (m, 1H), 2.19-2.08 (m, 1H), 2.04-1.95 (m, 1H), 1.62 (s, 3H), 1.49 (s, 9H).

Preparation D tert-Butyl rel-(4aS,10bS)-9-amino-10b-methyl-4a,5,6,10b-tetrahydro-4H-naphtho[1,2-d][1,3]thiazin-2-ylcarbamate

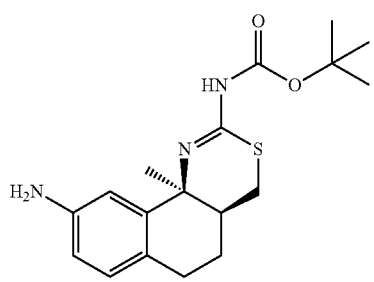 [SMILES: CC(C)(C)OC(=O)NC1=N[C@]2(C)c3cc(N)ccc3CC[C@@H]2CS1]

Step D1. tert-Butyl rel-(4aS,10bS)-9-azido-10b-methyl-4a,5,6,10b-tetrahydro-4H-naphtho[1,2-d][1,3]thiazin-2-ylcarbamate To a solution of tert-butyl rel-((4aS,10bS)-9-bromo-10b-methyl-4a,5,6,10b-tetrahydro-4H-naphtho[1,2-d][1,3]thiazin-2-yl)carbamate from preparation C (300 mg, 0.729 mmol) in ethanol (3.6 mL) was added sodium azide (228 mg, 3.51 mmol), trans-1,2-bis(methylamino)cyclohexane (55 mg, 0.387 mmol), 0.66 M solution of aqueous L-ascorbic acid sodium salt (0.780 mL, 0.515 mmol) and water (0.70 mL) and the mixture was purged with nitrogen for 10 min. A 0.33 M solution of aqueous copper(II) sulfate pentahydrate (0.780 mL, 0.257 mmol) was added and the reaction was heated to 80° C. for 12 min. The reaction was poured into water and was extracted three times with ethyl acetate. The combined organic layers were washed with brine, dried over sodium sulfate, filtered and concentrated in vacuo. The crude product was purified using silica gel column chromatography (2:1 hexanes/EtOAc) to afford tert-butyl rel-((4aS,10bS)-9-azido-10b-methyl-4a,5,6,10b-tetrahydro-4H-naphtho[1,2-d][1,3]thiazin-2-yl)carbamate (190 mg, 0.509 mmol, 70% yield) as a clear viscous oil. LCMS (M+Na)$^+$=396.1. $^1$H NMR (500 MHz, chloroform-d) δ 7.11 (br. s., 1H), 7.09 (d, J=8.2 Hz, 1H), 6.89 (dd, J=8.2, 2.1 Hz, 1H), 3.03 (dd, J=12.9, 3.6 Hz, 1H), 2.94-2.79 (m, 3H), 2.27 (br. s., 1H), 2.21-2.07 (m, 1H), 1.99 (dq, J=13.8, 6.7 Hz, 1H), 1.62 (s, 3H), 1.48 (s, 9H).

Step D2. tert-Butyl rel-(4aS,10bS)-9-amino-10b-methyl-4a,5,6,10b-tetrahydro-4H-naphtho[1,2-d][1,3]thiazin-2-ylcarbamate 10% Palladium on carbon (54 mg, 0.051 mmol) was added to a flask charged with a solution of tert-butyl rel-((4aS,10bS)-9-azido-10b-methyl-4a,5,6,10b-tetrahydro-4H-naphtho[1,2-d][1,3]thiazin-2-yl)carbamate from step D1 (190 mg, 0.509 mmol) in methanol (40 mL) under dry nitrogen. The vessel was repeatedly flushed with hydrogen gas. The reaction mixture was allowed to stir under a balloon of hydrogen gas for 20 h. The vessel was flushed with nitrogen. The contents were filtered through celite. The celite and vessel were rinsed with methanol. The combined filtrates were concentrated in vacuo. The residue was dried under high vacuum to afford tert-butyl((4aS,10bS)-9-amino-10b-methyl-4a,5,6,10b-tetrahydro-4H-naphtho[1,2-d][1,3]thiazin-2-yl)carbamate (180 mg, 0.518 mmol, 100% yield) as a gray oil. LCMS (M+Na)$^+$=270.1. $^1$H NMR (500 MHz, chloroform-d) δ 6.89 (d, J=8.1 Hz, 1H), 6.81-6.72 (m, 1H), 6.58 (dd, J=8.1, 2.4 Hz, 1H), 3.66 (br. s, 2H), 3.03 (dd, J=13.0, 3.7 Hz, 1H), 2.92 (dd, J=12.9, 8.3 Hz, 1H), 2.77 (t, J=6.9 Hz, 2H), 2.26 (dt, J=7.2, 3.6 Hz, 1H), 2.11 (dtd, J=14.0, 7.1, 3.6 Hz, 1H), 1.97 (dq, J=13.7, 6.7 Hz, 1H), 1.63 (s, 3H), 1.49 (s, 9H).

Preparation E tert-Butyl rel-((4aS,11bS)-10-bromo-11b-methyl-4,4a,5,6,7,11b-hexahydrobenzo[6,7]cyclohepta[1,2-d][1,3]thiazin-2-yl)carbamate

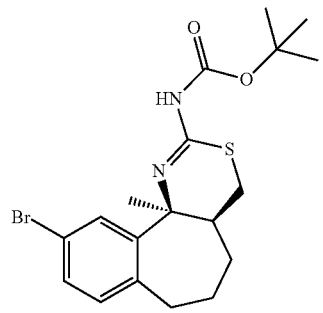 [SMILES: CC(C)(C)OC(=O)NC1=N[C@]2(C)c3cc(Br)ccc3CCC[C@@H]2CS1]

Step E1. 3-Bromo-6-methylene-6,7,8,9-tetrahydro-5H-benzo[7]annulen-5-one

In a manner similar to the procedure of step C1, but using 3-bromo-6,7,8,9-tetrahydro-5H-benzo[7]annulen-5-one from step A1 (2.36 g, 9.89 mmol), the titled compound of Step E1 (1.2 g, 4.78 mmol, 48% yield) was isolated as a thick viscous yellow oil. Analysis of the product using ¹H NMR revealed the product to be contaminated with approximately 20% by weight of an isomeric compound, 3-bromo-6-methyl-8,9-dihydro-5H-benzo[7]annulen-5-one. Data for 3-bromo-6-methylene-6,7,8,9-tetrahydro-5H-benzo[7]annulen-5-one: ¹H NMR (500 MHz, chloroform-d) δ 7.85 (d, J=2.1 Hz, 1H), 7.60-7.56 (m, 1H), 7.08 (d, J=8.1 Hz, 1H), 6.28 (d, J=1.8 Hz, 1H), 5.48 (dt, J=1.8, 0.9 Hz, 1H), 2.78 (t, J=6.9 Hz, 2H), 2.42-2.35 (m, 2H), 1.93 (quin, J=6.9 Hz, 2H).

Step E2. 7-Bromo-1-methyl-2-methylene-1,2,3,4-tetrahydronaphthalen-1-ol

In a manner similar to the procedure of step C2, but using 3-bromo-6-methylene-6,7,8,9-tetrahydro-5H-benzo[7]annulen-5-one from step E1 (1.15 g, 4.58 mmol), the titled compound of Step E2 was isolated (400 mg, 1.50 mmol, 33% yield) as a clear oil. Analysis of the product using ¹H NMR revealed that it was contaminated with approximately 50% of an isomeric compound, 3-bromo-6-ethyl-6,7,8,9-tetrahydro-5H-benzo[7]annulen-5-one. Data for 7-bromo-1-methyl-2-methylene-1,2,3,4-tetrahydronaphthalen-1-ol: ¹H NMR (400 MHz, chloroform-d) δ 7.86 (d, J=2.3 Hz, 1H), 7.29 (dd, J=8.0, 2.3 Hz, 1H), 7.01 (d, J=8.3 Hz, 1H), 5.39-5.25 (m, 1H), 4.99 (d, J=1.0 Hz, 1H), 2.86-2.69 (m, 2H), 2.55 (dd, J=7.7, 5.9 Hz, 1H), 2.37-2.31 (m, 2H), 2.02-1.96 (m, 1H), 1.71 (s, 3H).

Step E3. (2-Bromo-9-methyl-6,7-dihydro-5H-benzo[7]annulen-8-yl)methyl carbamimidothioate, hydrochloride In a manner similar to the procedure of step C3, but using 7-bromo-1-methyl-2-methylene-1,2,3,4-tetrahydronaphthalen-1-ol from step E2 (0.298 g, 1.12 mmol), the titled compound of step E3 (543 mg, quantitative yield) was isolated as white solid.

Step E4. rel-(4aS,11bS)-10-Bromo-11b-methyl-4,4a,5,6,7,11b-hexahydrobenzo[6,7]cyclohepta[1,2-d][1,3]thiazin-2-amine, 2,2,2-trifluoroacetate Triflic acid (1.33 mL, 15.0 mmol) was added to flask charged with a stirred solution of (2-bromo-9-methyl-6,7-dihydro-5H-benzo[7]annulen-8-yl)methyl carbamimidothioate, HCl from step E3 (540 mg, 1.5 mmol) in TFA (5.0 mL) at 0° C. The reaction mixture was allowed to warm to rt and stir for 6 h. The reaction contents were carefully added to a swirled mixture of ice and excess solid sodium bicarbonate. After gas evolution had ceased, the resulting mixture was extracted with ethyl acetate. The combined organic layers were washed with brine, dried over sodium sulfate, filtered, and concentrated in vacuo. The crude product was purified using preparatory HPLC (SunFire PrepC18 OBD 10 mm, 50×250 mm column, 90% MeOH/10% water/0.1% TFA-90% MeOH/10% water/0.1% TFA, linear gradiant over 34 min, 50 ml/min) to afford (4aS,11bS)-10-bromo-11b-methyl-4,4a,5,6,7,11b-hexahydrobenzo[6,7]cyclohepta[1,2-d][1,3]thiazin-2-amine, TFA (77 mg, 0.18 mmol, 12% yield) as a white solid. LCMS (M+H)⁺=327.0. ¹H NMR (500 MHz, methanol-d₄) δ 7.43 (dd, J=8.1, 2.1 Hz, 1H), 7.26 (d, J=2.1 Hz, 1H), 7.20 (d, J=8.1 Hz, 1H), 3.17-3.06 (m, 1H), 2.96 (dd, J=12.1, 3.1 Hz, 1H), 2.89 (dd, J=15.4, 5.6 Hz, 1H), 2.80 (t, J=12.4 Hz, 1H), 2.57-2.39 (m, 2H), 2.08 (dd, J=14.8, 4.0 Hz, 1H), 1.94-1.86 (m, 1H), 1.84 (s, 3H), 1.67-1.48 (m, 1H).

Step E5. tert-Butyl rel-((4aS,11bS)-10-bromo-11b-methyl-4,4a,5,6,7,11b-hexahydrobenzo[6,7]cyclohepta[1,2-d][1,3]thiazin-2-yl)carbamate A mixture of rel-(4aS,11bS)-10-bromo-11b-methyl-4,4a,5,6,7,11b-hexahydrobenzo[6,7]cyclohepta[1,2-d][1,3]thiazin-2-amine, TFA from step E4 (176 mg, 0.401 mmol), di-tert-butyl dicarbonate (0.279 mL, 1.20 mmol), TEA (0.223 mL, 1.60 mmol), and DMAP (2.5 mg, 0.020 mmol) were stirred in THF (5 mL) at rt for 2 h. The reaction mixture was concentrated in vacuo and purified using silica gel column chromatography (5:1-2:1 hexanes/EtOAc) to afford tert-butyl rel-((4aS,11bS)-10-bromo-11b-methyl-4,4a,5,6,7,11b-hexahydrobenzo[6,7]cyclohepta[1,2-d][1,3]thiazin-2-yl)carbamate (142 mg, 0.327 mmol, 82% yield) as a clear residue. LCMS (M+Na)⁺ 449.0. ¹H NMR (500 MHz, chloroform-d) δ 7.37 (d, J=2.0 Hz, 1H), 7.29 (dd, J=8.0, 2.1 Hz, 1H), 6.99 (d, J=8.1 Hz, 1H), 3.04-2.93 (m, 1H), 2.79 (dd, J=15.3, 5.6 Hz, 1H), 2.74-2.65 (m, 1H), 2.50 (dd, J=12.1, 2.7 Hz, 1H), 2.41-2.29 (m, 2H), 1.98 (dd, J=13.9, 2.6 Hz, 1H), 1.89-1.78 (m, 1H), 1.71 (s, 3H), 1.52 (s, 9H), 1.55-1.44 (m, 1H).

Preparation F tert-Butyl (4aR,10bS)-9-bromo-8-fluoro-10b-methyl-4,4a,5,10b-tetrahydrochromeno[4,3-d][1,3]thiazin-2-ylcarbamate

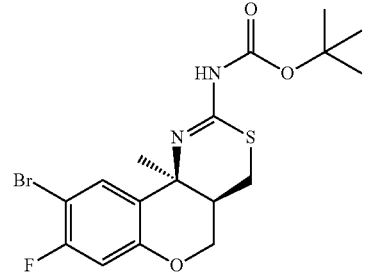 [SMILES: CC(C)(C)OC(=O)NC1=N[C@]2(C)c3cc(Br)c(F)cc3OC[C@@H]2CS1]

Step F1. 1-(2-(Allyloxy)-4-fluorophenyl)ethanone

A mixture of 1-(4-fluoro-2-hydroxyphenyl)ethanone (7.50 g, 48.7 mmol), 3-bromoprop-1-ene (6.48 g, 53.5 mmol), and potassium carbonate (13.5 g, 97.0 mmol) in DMF (75 mL) was vigorously stirred at rt for 24 h. The reaction mixture was diluted with water (100 mL) while stirring. The white precipitate was collected by vacuum filtration. The solid was rinsed with water (300 mL). The solid was dried under high vacuum to afford 1-(2-(allyloxy)-4-fluorophenyl)ethanone (7.92 g, 40.0 mmol, 82% yield) as a white solid. LCMS (M+Na)⁺=217.1. ¹H NMR (500 MHz, chloroform-d) δ 7.82 (dd, J=8.7, 7.0 Hz, 1H), 6.71 (ddd, J=8.7, 7.6, 2.3 Hz, 1H), 6.66 (dd, J=10.8, 2.3 Hz, 1H), 6.08 (ddt, J=17.3, 10.6, 5.3 Hz, 1H), 5.55-5.41 (m, 1H), 5.41-5.29 (m, 1H), 4.63 (dt, J=5.4, 1.4 Hz, 2H), 2.62 (s, 3H).

Step F2. rel-(3aR,9bS)-1-Benzyl-7-fluoro-9b-methyl-3,3a,4,9b-tetrahydro-1H-chromeno[4,3-c]isoxazole N-Benzylhydroxylamine, HCl (2.99 g, 18.7 mmol) was added to a solution of 1-(2-(allyloxy)-4-fluorophenyl)ethanone from step F1 (2.8 g, 14.42 mmol), in ethanol (100 mL) at rt. The reaction mixture was heated in a sealed tube at 70° C. for 2 h. The temperature was increase to 100° C. and stirring was continued for 4 d. The mixture was cooled to rt and allowed to age for 20 h. A crystalline solid formed in the reaction solution. The solid was collected using vacuum filtration and was rinsed with ethanol (3 mL). The solid was dried under high vacuum to afford rel-(3aR,9bS)-1-benzyl-7-fluoro-9b-methyl-3,3a,4,9b-tetrahydro-1H-chromeno[4,3-c]isoxazole (1.2 g, 4.0 mmol, 28% yield) as a white crystalline solid. LCMS (M+H)$^+$=300.2. $^1$H NMR (500 MHz, chloroform-d) δ 7.42 (dd, J=8.6, 6.5 Hz, 1H), 7.38 (d, J=7.5 Hz, 2H), 7.34-7.28 (m, 2H), 7.26-7.22 (m, 1H), 6.71 (td, J=8.5, 2.6 Hz, 1H), 6.60 (dd, J=10.0, 2.5 Hz, 1H), 4.32-4.21 (m, 2H), 4.21-4.14 (m, 1H), 4.01-3.92 (m, 1H), 3.92-3.88 (m, 1H), 3.87 (dd, J=8.1, 5.5 Hz, 1H), 2.80 (dtd, J=9.0, 5.5, 3.4 Hz, 1H), 1.59 (s, 3H).

Step F3. rel-((3S,4S)-4-Amino-7-fluoro-4-methylchroman-3-yl)methanol

10% Palladium on carbon (0.213 g, 0.200 mmol) was added under a nitrogen atmosphere to a solution of rel-(3aR,9bS)-1-benzyl-7-fluoro-9b-methyl-3,3a,4,9b-tetrahydro-1H-chromeno[4,3-c]isoxazole from step F2 (1.2 g, 4.01 mmol), in MeOH (200 mL). The resulting flask was repeatedly flushed with hydrogen gas and vigorously stirred under an atmosphere of hydrogen (double balloon) for 24 h. The reaction mixture was purged with nitrogen, filtered through celite, and concentrated in vacuo. The filtrate was dissolved in MeOH and passed through a 0.45 um filter. The filtrate was concentrated in vacuo and dried under high vacuum to afford rel-((3S,4S)-4-amino-7-fluoro-4-methylchroman-3-yl)methanol (0.80 g, 3.8 mmol, 94% yield) as a viscous oil. The crude product was used for subsequent chemistry without purification or characterization.

Step F4. rel-N-(((3S,4S)-7-Fluoro-3-(hydroxymethyl)-4-methylchroman-4-yl)carbamothioyl)benzamide A solution of ((3S,4S)-4-amino-7-fluoro-4-methylchroman-3-yl)methanol from step F3 (795 mg, 3.76 mmol), and benzoyl isothiocyanate (614 mg, 3.76 mmol) in THF (50 mL) was stirred at rt for 1.5 h. The resulting mixture was concentrated in vacuo. The crude residue was purified using silica gel column chromatography (95:5 chloroform/MeOH) to afford rel-N-(((3S,4S)-7-fluoro-3-(hydroxymethyl)-4-methylchroman-4-yl)carbamothioyl)benzamide (1.32 g, 3.53 mmol, 94% yield). LCMS (M+Na)$^+$=397.2. $^1$H NMR (500 MHz, DMSO-d$_6$) δ 11.45 (s, 1H), 11.26 (s, 1H), 7.91 (dd, J=8.4, 1.2 Hz, 2H), 7.68-7.58 (m, 1H), 7.57-7.41 (m, 3H), 6.86 (td, J=8.5, 2.7 Hz, 1H), 6.70 (dd, J=10.4, 2.7 Hz, 1H), 4.84 (t, J=4.7 Hz, 1H), 4.56 (dd, J=11.4, 3.1 Hz, 1H), 4.20 (dd, J=11.4, 1.6 Hz, 1H), 3.64-3.52 (m, 1H), 3.26-3.12 (m, 2H), 2.07 (s, 2H).

Step F5. rel-N-((4aR,10bS)-8-Fluoro-10b-methyl-4,4a,5,10b-tetrahydrochromeno[4,3-d][1,3]thiazin-2-yl)benzamide DCM (40 mL) and pyridine (0.539 mL, 6.67 mmol) were added to rel-N-(((3S,4S)-7-fluoro-3-(hydroxymethyl)-4-methylchroman-4-yl)carbamothioyl)benzamide from step F4 (832 mg, 2.22 mmol), under an atmosphere of dry nitrogen. The mixture was cooled to −78° C. Triflic anhydride (0.751 mL, 4.44 mmol) was slowly added to the reaction solution over 10 min. The resulting mixture was stirred for 15 min and then further stirred for 1 h while warming to 0° C. After adding ethyl acetate, a saturated solution of sodium bicarbonate was added. The mixture was extracted with ethyl acetate, the combined organic extracts were washed with brine, dried over sodium sulfate, filtered and concentrated in vacuo. The crude product was dissolved in dichloromethane and one drop of water and one drop of TFA was added. The reaction was stirred for 15 min, then concentrated in vacuo to afford rel-N-((4aR,10bS)-8-fluoro-10b-methyl-4,4a,5,10b-tetrahydrochromeno[4,3-d][1,3]thiazin-2-yl)benzamide. The crude product was used for subsequent chemistry without further purification. LCMS (M+H)$^+$=357.2.

Step F6. rel-(4aR,10bS)-8-Fluoro-10b-methyl-4,4a,5,10b-tetrahydrochromeno[4,3-d][1,3]thiazin-2-amine A mixture of rel-N-((4aR,10bS)-8-Fluoro-10b-methyl-4,4a,5,10b-tetrahydrochromeno[4,3-d][1,3]thiazin-2-yl)benzamide from step F5 (1.27 g, 3.56 mmol), pyridine (1.0 mL, 12.36 mmol), and hydroxylamine methyl ether hydrochloride (1.0 g, 12.0 mmol) in ethanol (100 mL) was heated at 50° C. for 24 h. The mixture was concentrated under reduced pressure. The residue was diluted with saturated aqueous sodium bicarbonate solution. The aqueous layer was extracted with EtOAc. The combined organic layers were washed with brine, dried over sodium sulfate, filtered and concentrated in vacuo. The crude product was purified using silica gel column chromatography (5-10% MeOH/dichloromethane) to afford rel-(4aR,10bS)-8-fluoro-10b-methyl-4,4a,5,10b-tetrahydrochromeno[4,3-d][1,3]thiazin-2-amine (644 mg, 2.50 mmol, 70% yield) as a viscous yellow oil. LCMS (M+H)$^+$=253.1. $^1$H NMR (500 MHz, chloroform-d) δ 7.59 (dd, J=8.8, 6.6 Hz, 1H), 6.73-6.65 (m, 1H), 6.51 (dd, J=10.1, 2.6 Hz, 1H), 4.40 (dd, J=11.4, 2.8 Hz, 1H), 4.21 (dd, J=11.4, 5.7 Hz, 1H), 3.15-3.02 (m, 2H), 2.14 (dddd, J=8.4, 5.7, 3.7, 2.9 Hz, 1H), 1.60 (s, 3H).

Step F7. rel-(4aR,10bS)-9-bromo-8-fluoro-10b-methyl-4,4a,5,10b-tetrahydrochromeno[4,3-d][1,3]thiazin-2-amine Bromine (0.20 mL, 3.80 mmol) was added dropwise to a solution of rel-(4aR,10bS)-8-fluoro-10b-methyl-4,4a,5,10b-tetrahydrochromeno[4,3-d][1,3]thiazin-2-amine from step F6 (644 mg, 2.55 mmol), in acetic acid (20 mL) at rt. The mixture was stirred for 30 min. The reaction was poured onto ice. The slurry was made pH 3 upon slow addition of 50% NaOH/water. The aqueous mixture was made basic pH 7-8 by the addition of solid sodium bicarbonate. The aqueous layers were extracted with EtOAc. The combined organic layers were dried over sodium sulfate, filtered, and concentrated in vacuo. The residue was purified using silica gel column chromatography (0.25%-10% MeOH/CHCl$_3$) to afford rel-(4aR,10bS)-9-bromo-8-fluoro-10b-methyl-4,4a,5,10b-tetrahydrochromeno[4,3-d][1,3]thiazin-2-amine (667 mg, 1.62 mmol, 64% yield) as a viscous oil. LCMS (M+H)$^+$=333.02. $^1$H NMR (500 MHz, methanol-d$_4$) δ 7.73 (d, J=7.5 Hz, 1H), 6.79 (d, J=9.8 Hz, 1H), 4.53 (dd, J=11.9, 2.9 Hz, 1H), 4.30 (dd, J=12.0, 6.0 Hz, 1H), 3.50 (dd, J=13.7, 3.9 Hz, 1H), 3.23 (dd, J=13.6, 8.1 Hz, 1H), 2.64 (dtd, J=10.0, 3.9, 3.0 Hz, 1H), 1.80 (s, 3H).

Step F8. tert-Butyl rel-((4aR,10bS)-9-bromo-8-fluoro-10b-methyl-4,4a,5,10b-tetrahydrochromeno[4,3-d][1,3]thiazin-2-yl)carbamate Di-tert-butyl dicarbonate (1.37 mL, 5.89 mmol) was added to flask charged with a stirred solution of rel-(4aR,10bS)-9- bromo-8-fluoro-10b-methyl-4,4a,5,10b-tetrahydro-chromeno[4,3-d][1,3]thiazin-2-amine from step F7 (650 mg, 1.963 mmol), in THF (50 mL) at rt. The resulting mixture was capped and left to stir for 24 h. The reaction mixture was concentrated in vacuo. The crude residue was purified using silica gel column chromatography (20:1 hexanes/EtOAc) to afford tert-butyl rel-((4aR,10bS)-9-bromo-8-fluoro-10b-methyl-4,4a,5,10b-tetrahydrochromeno[4,3-d][1,3]thiazin-2-yl)carbamate (615 mg, 1.43 mmol, 73% yield) as a clear viscous oil. LCMS (M+Na)$^+$=433.2. $^1$H NMR (500 MHz, chloroform-d) δ 7.76-7.52 (m, 1H), 6.61 (d, J=9.5 Hz, 1H), 4.40 (dd, J=11.4, 2.6 Hz, 1H), 4.22 (dd, J=11.4, 5.3 Hz, 1H), 3.11-3.00 (m, 1H), 3.00-2.88 (m, 1H), 2.25 (br. s., 1H), 1.63 (br. s., 3H), 1.49 (s, 9H).

Preparation G tert-Butyl rel-(4aR,10bS)-9-amino-8-fluoro-10b-methyl-4,4a,5,10b-tetrahydrochromeno[4,3-d][1,3]thiazin-2-ylcarbamate

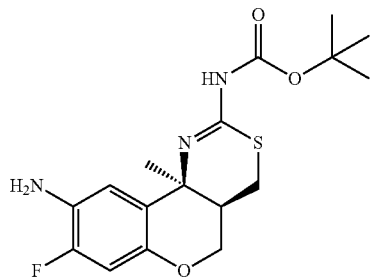 [SMILES: CC(C)(C)OC(=O)NC1=N[C@]2(C)c3cc(N)c(F)cc3OC[C@@H]2CS1]

In a manner similar to the two-step procedure used for preparation D, but using tert-butyl rel-((4aR,10bS)-9-bromo-8-fluoro-10b-methyl-4,4a,5,10b-tetrahydrochromeno[4,3-d][1,3]thiazin-2-yl)carbamate from preparation F (250 mg, 0.580 mmol), the titled compound of preparation G (204 mg, 0.555 mmol, 95% yield) was prepared as a gray oil. LCMS (M+Na)$^+$=390.2.

Preparation H tert-Butyl rel-((4aS,11bS)-10-bromo-11b-methyl-4a,5,6,11b-tetrahydro-4H-benzo[2,3]oxepino[4,5-d][1,3]thiazin-2-yl)carbamate

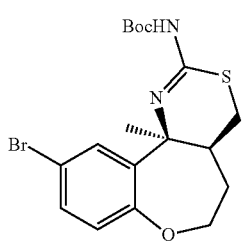 [SMILES: CC(C)(C)OC(=O)NC1=N[C@]2(C)c3cc(Br)ccc3OCC[C@@H]2CS1]

Step H1.
1-(5-Bromo-2-(2-bromoethoxy)phenyl)ethanone

To a stirred solution of 1-(5-bromo-2-hydroxyphenyl)ethanone (9.66 g, 44.9 mmol) in 2-butanone (100 mL) was added potassium carbonate (13 g, 94 mmol) then 1,2-dibromoethane (19.4 mL, 225 mmol). The reaction mixture was heated to reflux and stirred for 16 h. The crude mixture was filtered was washed with acetone, and the filtrate was concentrated in vacuo. The residue was treated with a mixture of diethyl ether/EtOAc (4:1; 250 mL) and the resulting solid was removed by filtration. The filtrate was washed with 2 M NaOH (150 mL), dried over sodium sulfate and concentrated in vacuo to give 1-(5-bromo-2-(2-bromoethoxy)phenyl)ethanone (9.0 g, 28.0 mmol, 62% yield) as a light yellow solid. $^1$H NMR (500 MHz, chloroform-d) δ 7.96-7.80 (m, 1H), 7.63-7.48 (m, 1H), 6.82 (d, J=8.7 Hz, 1H), 4.41 (t, J=5.7 Hz, 2H), 3.73 (t, J=5.7 Hz, 2H), 2.77-2.63 (m, 3H).

Step H2.
7-Bromo-3,4-dihydrobenzo[b]oxepin-5(2H)-one 1-(5-bromo-2-(2-bromoethoxy)phenyl)ethanone from step H (9.0 g, 28.0 mmol) was dissolved in THF (175 mL), cooled to 0° C. and treated with sodium hydride (0.805 g, 33.5 mmol). The reaction mixture was carefully heated to reflux and continued heating for 20 h. The crude mixture was cooled, quenched with 2 M HCl (50 mL) and partitioned between brine (300 mL) and EtOAc (250 mL). The organic layer was dried over sodium sulfate, concentrated in vacuo and purified by silica gel column chromatography (10-30% EtOAc/hexanes). The clean fractions were concentrated in vacuo to afford 7-bromo-3,4-dihydrobenzo[b]oxepin-5(2H)-one (5.41 g, 22.4 mmol, 80% yield) as a colorless oil. LCMS (M+H)$^+$=242.95. $^1$H NMR (500 MHz, chloroform-d) δ 7.91-7.85 (m, 1H), 7.54-7.48 (m, 1H), 6.98 (d, J=8.5 Hz, 1H), 4.25 (t, J=6.6 Hz, 2H), 2.91 (t, J=6.9 Hz, 2H), 2.23 (quin, J=6.8 Hz, 2H).

Step H3. Methyl-7-bromo-5-oxo-2,3,4,5-tetrahydrobenzo[b]oxepine-4-carboxylate

To a solution of 7-bromo-3,4-dihydrobenzo[b]oxepin-5(2H)-one from step H2 (5.41 g, 22.4 mmol) in dimethyl carbonate (28.3 ml, 337 mmol) was slowly added a sodium hydride dispersion in mineral oil (2.69 g, 112 mmol). The mixture was stirred at rt for 15 min, then at 80° C. for 2 h. The mixture was then cooled to rt and stirred for 16 h. The mixture was concentrated in vacuo and diethyl ether (150 mL) of was added. The organic layer was washed with of 1 N HCl (100 mL) followed by water, and dried over sodium sulfate. The solvent was removed in vacuo. The crude product was purified by silica-gel column chromatography (10-40% EtOAc/hexanes, linear gradient) to afford methyl 7-bromo-5-oxo-2,3,4,5-tetrahydrobenzo[b]oxepine-4-carboxylate (3.32 g, 11.1 mmol, 50% yield) as a white solid. LCMS (M+H)$^+$=300.95. $^1$H NMR (500 MHz, chloroform-d) δ 7.91 (d, J=2.4 Hz, 1H), 7.61-7.48 (m, 1H), 7.03-6.89 (m, 1H), 4.49 (ddd, J=12.4, 6.7, 3.9 Hz, 1H), 4.15-4.03 (m, 2H), 3.77 (s, 3H), 2.68-2.47 (m, 2H).

Step H4. Methyl 7-bromo-5-(((trifluoromethyl)sulfonyl)oxy)-2,3-dihydrobenzo[b]oxepine-4-carboxylate To a solution of methyl 7-bromo-5-oxo-2,3,4,5-tetrahydrobenzo[b]oxepine-4-carboxylate from step H3 (6.5 g, 21.73 mmol), in DME (150 mL) was slowly added sodium hydride (1.22 g, 30.4 mmol) at 0° C. under nitrogen. After stirring for 10 min, triflic anhydride (4.41 mL, 26.1 mmol) was slowly added. The mixture was stirred from 0° C. to rt over a period of 12 h. The mixture was diluted with diethyl ether (100 mL). The organic layer was washed with water, brine, dried over sodium sulfate and concentrated in vacuo to afford methyl 7-bromo-5-(((trifluoromethyl)sulfonyl)oxy)-2,3-dihydrobenzo[b]oxepine-4-carboxylate (8.55 g, 19.9 mmol, 92% yield) as a yellow-waxy solid. LCMS (M+H)$^+$=430.9. $^1$H NMR (500 MHz, chloroform-d) δ 7.64 (d, J=2.4 Hz, 1H), 7.53 (dd, J=8.7, 2.4 Hz, 1H), 7.01 (d, J=8.7 Hz, 1H), 4.61 (t, J=5.7 Hz, 2H), 3.92 (s, 3H), 2.76 (t, J=5.7 Hz, 2H).

Step H5. Methyl 7-bromo-5-methyl-2,3-dihydrobenzo[b]oxepine-4-carboxylate

A solution of 0.4 M (Me)$_2$CuLi was prepared via dropwise addition of methyl lithium in hexanes (1.6 M, 72 mmol, 45 mL) to a suspension of CuI (6.86 g, 36 mmol) in anhydrous diethyl ether (45 mL) in a ice-salt bath. After stirring for 20 min, a homogeneous solution resulted. The solution of dimethyl cuprate was slowly added to a solution of methyl 7-bromo-5-(((trifluoromethyl)sulfonyl)oxy)-2,3-dihydrobenzo[b]oxepine-4-carboxylate from step H4 (5.1 g, 11.8 mmol) in diethyl ether (40 mL) at −78° C. The mixture was stirred from −78° C. to −40° C. over 2 h. The reaction was quenched with 30 mL of water and the mixture was extracted with diethyl ether (2×200 mL). The combined organic layers were dried over sodium sulfate and concentrated to give methyl 7-bromo-5-methyl-2,3-dihydrobenzo[b]oxepine-4-carboxylate (3.41 g, 11.5 mmol, 97% yield). The crude mixture was used in the next step without purification. $^1$H NMR (500 MHz, chloroform-d) δ 7.45 (d, J=2.4 Hz, 1H), 7.40 (dd, J=8.5, 2.4 Hz, 1H), 6.95 (d, J=8.5 Hz, 1H), 4.53 (t, J=6.1 Hz, 2H), 3.84 (s, 3H), 2.54-2.49 (m, 2H), 2.45-2.42 (m, 3H).

Step H6. (7-Bromo-5-methyl-2,3-dihydrobenzo[b]oxepin-4-yl)methanol

To a stirred solution of methyl 7-bromo-5-methyl-2,3-dihydrobenzo[b]oxepine-4-carboxylate from step H5 (2.0 g, 6.73 mmol), in THF (75 mL) was added DIBAL-H/THF (1.0 M, 67.3 mL, 67.3 mmol) at −60° C. The mixture was allowed to warm to rt over 3 h. The reaction was chilled to −78° C. and additional DIBAL-H in THF (5.0 equivalents) was added. The reaction was again allowed to warm to rt over 3 h. After an additional 20 h, the reaction mixture was carefully quenched with water. The aqueous mixture was extracted with diethyl ether. The organic layer was concentrated in vacuo. The residue was purified by silica-gel column chromatography (hexanes-50% EtOAc) to give (7-bromo-5-methyl-2,3-dihydrobenzo[b]oxepin-4-yl)methanol (1.53 g, 5.68 mmol, 84% yield). MS (M+H-water)$^+$=251.

Step H7. 7-Bromo-4-(chloromethyl)-5-methyl-2,3-dihydrobenzo[b]oxepine

To a solution of (7-bromo-5-methyl-2,3-dihydrobenzo[b]oxepin-4-yl)methanol from step H6 (1.53 g, 5.68 mmol) in dichloromethane (10 mL) was added DIPEA (2.98 mL, 17.1 mmol) followed by methanesulfonyl chloride (0.886 mL, 11.4 mmol) at 0° C. The mixture was allowed to gradually warm up to rt. After 18 h at rt, diethyl ether (50 mL) was added, the mixture was washed with water, and the organic layer was separated, dried over sodium sulfate, filtered, and concentrated in vacuo to give 7-bromo-4-(chloromethyl)-5-methyl-2,3-dihydrobenzo[b]oxepine (2.05 g, 7.13 mmol, 125% yield). The crude material was used in the next step without further purification. $^1$H NMR (500 MHz, chloroform-d) δ 7.40 (d, J=2.4 Hz, 1H), 7.36-7.32 (m, 1H), 6.96 (s, 1H), 4.56 (t, J=6.3 Hz, 2H), 4.37 (s, 2H), 2.34 (t, J=1.0 Hz, 2H), 2.17 (s, 3H).

Step H8. (7-Bromo-5-methyl-2,3-dihydrobenzo[b]oxepin-4-yl)methyl carbamimidothioate, hydrochloride To a solution of 7-bromo-4-(chloromethyl)-5-methyl-2,3-dihydrobenzo[b]oxepine from step H7 (2.05 g, 7.13 mmol) in ethanol (75 mL) was added thiourea (0.651 g, 8.55 mmol). The mixture was refluxed for 3 h. A white solid precipitated. The solvent was removed. The solid residue was washed with hexanes and dried in vacuo to give a (7-bromo-5-methyl-2,3-dihydrobenzo[b]oxepin-4-yl)methyl carbamimidothioate hydrochloride (2.64 g, 7.26 mmol, 102% yield). The crude mixture was used in the next step without further purification. $^1$H NMR (500 MHz, methanol-d$_4$) δ 7.48 (d, J=2.4 Hz, 1H), 7.43-7.36 (m, 1H), 6.97 (d, J=8.5 Hz, 1H), 4.53 (t, J=6.3 Hz, 2H), 4.25 (s, 2H), 2.34 (t, J=6.1 Hz, 2H), 2.18 (s, 3H).

Step H9. rel-(4aS,11bS)-10-Bromo-11b-methyl-4a,5,6,11b-tetrahydro-4H-benzo[2,3]oxepino[4,5-d][1,3]thiazin-2-amine To a solution of (7-bromo-5-methyl-2,3-dihydrobenzo[b]oxepin-4-yl)methyl carbamimidothioate hydrochloride from step H8 (2.59 g, 7.12 mmol) in TFA (20 mL) was added triflic acid (5.0 mL). The mixture was stirred at rt for 3 h. The reaction mixture was chilled to 0° C. then diluted with diethyl ether (150 mL). The resulting mixture was slowly neutralized with 50% aqueous NaOH and made basic (pH=12) with saturated aqueous NaHCO$_3$ solution. The organic layer was separated, dried over sodium sulfate, filtered, and concentrated in vacuo. The crude material was purified by silica gel column chromography (30-100% EtOAc/hexanes) to afford rel-(4aS,11bS)-10-bromo-11b-methyl-4a,5,6,11b-tetrahydro-4H-benzo[2,3]oxepino[4,5-d][1,3]thiazin-2-amine (1.31 g, 4.00 mmol, 56% yield). LCMS (M+H)$^+$=329.0. $^1$H NMR (500 MHz, methanol-d$_4$) δ 7.50 (dd, J=8.5, 2.4 Hz, 1H), 7.18 (d, J=2.4 Hz, 1H), 7.05 (d, J=8.4 Hz, 1H), 4.38-4.31 (m, 1H), 3.76 (td, J=13.2, 1.5 Hz, 1H), 3.05-2.92 (m, 2H), 2.85 (ddt, J=15.5, 13.4, 4.5 Hz, 1H), 2.55-2.47 (m, 1H), 1.96-1.88 (m, 1H), 1.86 (s, 3H).

Step H10. tert-Butyl rel-((4aS,11bS)-10-bromo-11b-methyl-4a,5,6,11b-tetrahydro-4H-benzo[2,3]oxepino[4,5-d][1,3]thiazin-2-yl)carbamate A mixture of rel-(4aS,11bS)-10-bromo-11b-methyl-4a,5,6,11b-tetrahydro-4H-benzo[2,3]oxepino[4,5-d][1,3]thiazin-2-amine from step A9 (500 mg, 1.53 mmol), di-tert-butyl dicarbonate (1.06 mL, 4.58 mmol), and TEA (0.852 mL, 6.11 mmol), were stirred in THF (10 mL) at rt for 2 h. The reaction mixture was concentrated in vacuo and purified using silica gel column chromatography (0-50% EtOAc/hexanes, linear gradient) to afford tert-butyl rel-((4aS,11bS)-10-bromo-11b-methyl-4a,5,6,11b-tetrahydro-4H-benzo[2,3]oxepino[4,5-d][1,3]thiazin-2-yl)carbamate (235 mg, 0.550 mmol, 36% yield) as a pale-yellow solid. LCMS (M+H)$^+$=429.0. $^1$H NMR (500 MHz, chloroform-d) δ 7.40 (d, J=8.2 Hz, 1H), 7.28 (s, 1H), 6.96 (s, 1H), 4.35 (d, J=11.3 Hz, 1H), 3.65 (t, J=12.5 Hz, 1H), 2.96-2.77 (m, 2H), 2.63 (br. s., 1H), 2.41 (d, J=11.9 Hz, 1H), 2.09-1.76 (m, 4H), 1.64-1.44 (m, 9H).

Preparation I tert-Butyl rel-((4aS,11bS)-10-amino-11b-methyl-4a,5,6,11b-tetrahydro-4H-benzo[2,3]oxepino[4,5-d][1,3]thiazin-2-yl)carbamate

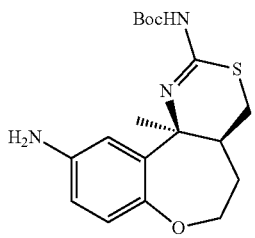 [SMILES: CC(C)(C)OC(=O)NC1=N[C@]2(C)c3cc(N)ccc3OCC[C@@H]2CS1]

In a manner similar to the two-step procedure used for preparation D, but using tert-butyl rel-((4aS,11bS)-10-bromo-11b-methyl-4a,5,6,11b-tetrahydro-4H-benzo[2,3]oxepino[4,5-d][1,3]thiazin-2-yl)carbamate from preparation H (500 mg, 1.17 mmol), the titled compound of preparation I (93 mg, 0.256 mmol, 22% yield) was prepared as a gray solid. LCMS (M+H)+ 364.1.

Preparation J (E)-(2-Amino-9-methyl-6,7-dihydro-5H-benzo[7]annulen-8-yl)methanol

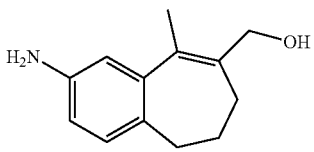

Step J1. (E)-Methyl 2-amino-9-methyl-6,7-dihydro-5H-benzo[7]annulene-8-carboxylate To a solution of (E)-methyl 2-bromo-9-methyl-6,7-dihydro-5H-benzo[7]annulene-8-carboxylate from step B2 of preparation B (500 mg, 1.694 mmol) in dioxane (5 mL) was added 2,2,2-trifluoroacetamide (1.92 g, 16.94 mmol), copper (I) iodide (323 mg, 1.69 mmol), N1,N2-dimethylethane-1,2-diamine (448 mg, 5.08 mmol) and potassium carbonate (702 mg, 5.08 mmol). The mixture was heated in a microwave reactor at 120° C. for 2 h and 15 min. Then water (3 mL), MeOH (3 mL), and potassium carbonate (1 g) were added. The mixture was stirred at rt for 16 h. The mixture was concentrated, the residue was diluted with water (50 mL), and the mixture was extracted with EtOAc. The organic layers were combined, and concentrated. The residue was purified by silica gel column chromatography (hexanes-50% EtOAc) to afford methyl 2-amino-9-methyl-6,7-dihydro-5H-benzo[7]annulene-8-carboxylate (260 mg, 1.12 mmol, 66% yield). ¹H NMR (400 MHz, chloroform-d) δ 6.96 (d, J=8.0 Hz, 1H), 6.65 (d, J=2.3 Hz, 1H), 6.58 (dd, J=7.8, 2.5 Hz, 1H), 3.80 (s, 3H), 3.62 (br. s., 2H), 2.46 (t, J=6.9 Hz, 2H), 2.37 (s, 3H), 2.17-2.01 (m, 4H).

Step J2. (2-amino-9-methyl-6,7-dihydro-5H-benzo[7]annulen-8-yl)methanol

To a stirred solution of methyl 2-amino-9-methyl-6,7-dihydro-5H-benzo[7]annulene-8-carboxylate from step J1 (65 mg, 0.281 mmol) in THF (2 mL) was added a solution of LAH in THF (1.0 M, 0.337 mL, 0.337 mmol) at −20° C. The mixture was warmed to rt over 2 h. The reaction was quenched with a couple of drops of 1 N NaOH. EtOAc was added. The mixture was dried over sodium sulfate, filtered, and concentrated in vacuo to afford (2-amino-9-methyl-6,7-dihydro-5H-benzo[7]annulen-8-yl)methanol (55.0 mg, 0.271 mmol, 96% yield). LCMS (M+H)+=204.1. ¹H NMR (500 HMz, chloroform-d) δ 6.96 (d, J=7.9 Hz, 1H), 6.63 (d, J=2.4 Hz, 1H), 6.54 (dd, J=7.9, 2.4 Hz, 1H), 4.36 (d, J=3.4 Hz, 2H), 3.59 (br. s., 2H), 2.45 (t, J=6.9 Hz, 2H), 2.19 (d, J=2.9 Hz, 1H), 2.08 (s, 3H), 2.07-2.01 (m, 2H), 1.99-1.94 (m, 2H).

Preparation K 5-(Difluoromethoxy)picolinic acid

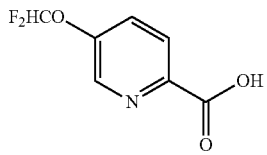 [SMILES: O=C(O)c1ccc(OC(F)F)cn1]

Step K1. Methyl 5-hydroxypicolinate hydrochloride

To solution of 5-hydroxypicolinic acid (820 mg, 5.89 mmol) in methanol (20 mL) was dropwise added thionyl chloride (0.430 mL, 5.89 mmol) at rt. The mixture was stirred at 60° C. for 20 h. The mixture was concentrated in vacuo to give a crude methyl 5-hydroxypicolinate hydrochloride (1.12 g, 5.89 mmol, 100% yield), which was used for the next step without purification. LCMS (M+H)+=154.01. ¹H NMR (500 HMz, methanol-d₄) δ 8.45 (d, J=6.0 Hz, 2H), 8.08 (dd, J=9.0, 2.3 Hz, 1H), 4.09 (s, 3H)

Step K2. Methyl 5-(difluoromethoxy)picolinate

A mixture of methyl 5-hydroxypicolinate hydrochloride from step K1 (1.12 g, 5.91 mmol), potassium carbonate (8.16 g, 59.1 mmol) and α-chloro-α,α-difluoroacetophenone (3.92 mL, 26.6 mmol) in water (20 mL) and acetonitrile (20 mL) was stirred at 75° C. for 5 h. The solid was filtered out and washed with diethyl ether. The filtrate was washed with water and concentrated. The residue was purified using silica gel column chromatography (hexanes-50% EtOAc) to give methyl 5-(difluoromethoxy)picolinate (730 mg, 3.59 mmol, 61% yield). ¹H NMR (500 HMz, chloroform-d) δ 8.60 (d, J=2.4 Hz, 1H), 8.20 (dd, J=8.6, 0.5 Hz, 1H), 7.62 (dd, J=8.7, 2.7 Hz, 1H), 6.81-6.49 (m, 1H), 4.03 (s, 3H).

Step K3. 5-(Difluoromethoxy)picolinic acid

To a solution of methyl 5-(difluoromethoxy)picolinate from step K2 (730 mg, 3.59 mmol) in THF (8 mL), was added a solution of lithium hydroxide (430 mg, 18.0 mmol) in water (5 mL). The mixture was stirred at rt for 3 h, then concentrated in vacuo. After the addition of 10 mL of 1 N HCl, 150 mL of EtOAc was added. The resulting mixture was washed with water. The organic layer was dried over sodium sulfate, filtered, and concentrated in vacuo to afford 5-(difluoromethoxy)picolinic acid (610 mg, 3.23 mmol, 90% yield). LCMS (M+H)$^+$=190.1. $^1$H NMR (500 HMz, chloroform-d) δ 8.52 (d, J=2.0 Hz, 1H), 8.30 (d, J=8.5 Hz, 1H), 7.74 (dd, J=8.5, 2.6 Hz, 1H), 6.84-6.53 (m, 1H).

Preparation L rel-(4aS,11bS)-10-Bromo-9-fluoro-4,4a,5,6,7,11b-hexahydro-3-thia-1-aza-dibenzo[a,c]cyclohepten-2-ylamine, bis-N,N-(tert-butyl)carbamate

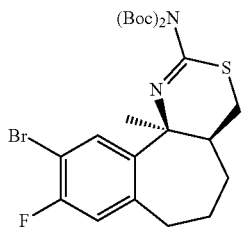

Step L1. (E)-5-(4-Bromo-3-fluorophenyl)pent-4-enoic acid

To a solution of 3-carboxypropyltriphenylphosphonium bromide (8.6 g, 20 mmol) in DMSO (20 mL) was added solid KOt-Bu (4.49 g, 40.0 mmol) at rt. After stirring for 40 min, a solution of 4-bromo-3-fluorobenzaldehyde (3.45 g, 17.00 mmol) in DMSO was added slowly. The mixture was stirred at rt for 16 h. The reaction was quenched with water (200 mL), washed with EtOAc/hexanes (1/1). The aqueous layer was neutralized with concentrated hydrochloric acid to pH=2, extracted with EtOAc. The organic layer was concentrated. The residue was purified by silica gel column chromatography (hexanes-100% EtOAc) to give (E)-5-(4-bromo-3-fluorophenyl)pent-4-enoic acid (2.2 g, 8.06 mmol, 40% yield). LCMS (M-H)$^-$=273.1. $^1$H NMR (500 HMz, chloroform-d) δ 7.47 (dd, J=8.2, 7.2 Hz, 1H), 7.12 (dd, J=9.9, 2.0 Hz, 1H), 7.00 (dd, J=8.2, 2.0 Hz, 1H), 6.41-6.36 (m, 1H), 6.29-6.22 (m, 1H), 2.58-2.56 (m, 4H).

Step L2. 5-(4-Bromo-3-fluorophenyl)pentanoic acid

To a solution of (E)-5-(4-bromo-3-fluorophenyl)pent-4-enoic acid from step L1 (420 mg, 1.54 mmol) in 2-propanol (5 mL), was added sulfide platinum 5 weight % on carbon (100 mg, 0.513 mmol). The mixture was stirred under a hydrogen filled balloon for 3 h. The solid was filtered off. The filtrate concentrated in vacuo to afford 5-(4-bromo-3-fluorophenyl)pentanoic acid (400 mg, 1.45 mmol, 95% yield). $^1$H NMR (500 HMz, chloroform-d) δ 7.45 (dd, J=8.0, 7.4 Hz, 1H), 6.96 (dd, J=9.7, 1.9 Hz, 1H), 6.86 (dd, J=8.1, 1.5 Hz, 1H), 2.66-2.60 (m, 2H), 2.43-2.38 (m, 2H), 1.72-1.64 (m, 4H).

Step L3. 3-Bromo-2-fluoro-6,7,8,9-tetrahydro-5H-benzo[7]annulen-5-one

A mixture of 5-(4-bromo-3-fluorophenyl)pentanoic acid from step L2 (5.1 g, 18.54 mmol) in polyphosphoric acid (75 g, 18.5 mmol) was stirred at 145-150° C. for 3 h. After cooling to rt, the mixture was poured into ice, neutralized with 50% NaOH/water, and extracted with EtOAc/diethyl ether. The organic layer was dried over sodium sulfate and concentrated. The residue was purified via silica gel column chromatography (hexanes-8% EtOAc) to give 3-bromo-2-fluoro-6,7,8,9-tetrahydro-5H-benzo[7]annulen-5-one (2.7 g, 10.5 mmol, 57% yield). LCMS (M+H)$^+$=257.0. $^1$H NMR (500 HMz, chloroform-d) δ 7.98 (d, J=7.3 Hz, 1H), 6.99 (d, J=8.9 Hz, 1H), 2.93-2.89 (m, 2H), 2.77-2.73 (m, 2H), 1.95-1.88 (m, 2H), 1.87-1.81 (m, 2H).

Step L4. Methyl 3-bromo-2-fluoro-5-oxo-6,7,8,9-tetrahydro-5H-benzo[7]annulene-6-carboxylate In a manner similar to the procedure of step A2, but using 3-bromo-2-fluoro-6,7,8,9-tetrahydro-5H-benzo[7]annulen-5-one from step L3, the titled compound of step L4 was prepared. LCMS (M+H)$^+$=314.95. $^1$H NMR (500 HMz, chloroform-d) δ 12.57 (s, 1H), 7.84 (d, J=7.2 Hz, 1H), 7.02 (d, J=8.8 Hz, 1H), 3.86 (s, 3H), 2.61 (t, J=6.8 Hz, 2H), 2.16-2.13 (m, 2H), 2.13-2.09 (m, 2H).

Step L5. (Z)-Methyl 2-bromo-3-fluoro-9-(trifluoromethylsulfonyloxy)-6,7-dihydro-5H-benzo[7]annulene-8-carboxylate In a manner similar to the procedure of step B1, but using methyl 3-bromo-2-fluoro-5-oxo-6,7,8,9-tetrahydro-5H-benzo[7]annulene-6-carboxylate from step L4, the titled compound of step L5 was prepared. $^1$H NMR (500 HMz, chloroform-d) δ 7.68 (d, J=6.7 Hz, 1H), 7.09 (d, J=8.7 Hz, 1H), 3.92 (s, 3H), 2.73-2.69 (m, 2H), 2.32-2.27 (m, 4H)

Step L6. (E)-Methyl 2-bromo-3-fluoro-9-methyl-6,7-dihydro-5H-benzo[7]annulene-8-carboxylate In a manner similar to the procedure of step B2, but using (Z)-methyl 2-bromo-3-fluoro-9-(trifluoromethylsulfonyloxy)-6,7-dihydro-5H-benzo[7]annulene-8-carboxylate from step L5 the titled compound of step L6 was prepared. $^1$H NMR (500 HMz, chloroform-d) δ 7.47 (d, J=6.9 Hz, 1H), 6.98 (d, J=9.2 Hz, 1H), 3.82 (s, 3H), 2.55-2.51 (m, 2H), 2.37 (s, 3H), 2.15-2.11 (m, 4H).

Step L7. (E)-(2-Bromo-3-fluoro-9-methyl-6,7-dihydro-5H-benzo[7]annulen-8-yl)methanol In a manner similar to the procedure of step A5, but using (E)-Methyl 2-bromo-3-fluoro-9-methyl-6,7-dihydro-5H-benzo[7]annulene-8-carboxylate from step L6 the titled compound of step L7 was prepared. $^1$H NMR (500 HMz, chloroform-d) δ 7.39 (d, J=7.0 Hz, 1H), 6.95 (d, J=9.2 Hz, 1H), 4.37 (s, 2H), 2.50 (t, J=7.1 Hz, 2H), 2.12-2.08 (m, 2H), 2.07 (s, 3H), 1.98-1.93 (m, 2H), 1.80 (br. s., 1H).

Step L8. (E)-2-Bromo-8-(chloromethyl)-3-fluoro-9-methyl-6,7-dihydro-5H-benzo[7]annulene In a manner similar to the procedure of step A6, but using (E)-(2-bromo-3-fluoro-9-methyl-6,7-dihydro-5H-benzo[7]annulen-8-yl)methanol from step L7 the titled compound of step L8 was prepared. $^1$H NMR (500 HMz, chloroform-d) δ 7.41 (d, J=6.9 Hz, 1H), 6.96 (d, J=9.2 Hz, 1H), 4.33 (s, 2H), 2.53 (t, J=7.1 Hz, 2H), 2.17 (t, J=7.2 Hz, 2H), 2.14 (s, 3H), 2.01-1.96 (m, 2H).

Step L9. rel-(4aS,11bS)-10-Bromo-9-fluoro-4,4a,5,6,7,11b-hexahydro-3-thia-1-aza-dibenzo[a,c]cyclohepten-2-ylamine, bis-N,N-(tert-butyl)carbamate In a manner similar to the procedures of steps A7 and A8, but using (E)-2-Bromo-8-(chloromethyl)-3-fluoro-9-methyl-6,7-dihydro-5H-benzo[7]annulene from step L8 the titled compound of preparation L was prepared. LCMS (M+H)$^+$=545.3. $^1$H NMR (500 HMz, chloroform-d) δ 7.76 (d, J=7.5 Hz, 1H), 6.89 (d, J=9.3 Hz, 1H), 3.07-2.99 (m, 1H), 2.86 (dd, J=12.1, 10.8 Hz, 1H), 2.78 (dd, J=15.0, 5.5 Hz, 1H), 2.72 (dd, J=12.1, 2.1 Hz, 1H), 2.30-2.22 (m, 1H), 2.16-2.10 (m, 1H), 1.86-1.78 (m, 1H), 1.70 (s, 3H), 1.64-1.60 (m, 1H), 1.56 (s, 18H).

EXAMPLES

The following examples set forth certain specific aspects of the invention, but should not be construed as limiting the scope thereof:

Example 1 rel-(4aS,11bS)-10-Pyrimidin-5-yl-4,4a,5,6,7,11b-hexahydro-3-thia-1-aza-dibenzo[a,c]cyclohepten-2-ylamine, bis(2,2,2-trifluoroacetate)

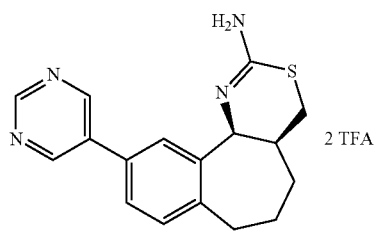 [SMILES: NC1=N[C@@H]2c3cc(-c4cncnc4)ccc3CCC[C@@H]2CS1]

Step 1A. rel-(4aS,11bS)-10-Pyrimidin-5-yl-4,4a,5,6,7,11b-hexahydro-3-thia-1-aza-dibenzo[a,c]cyclohepten-2-ylamine, bis-N,N-(tert-butyl)carbamate To a solution of the compound of preparation A (22 mg, 0.043 mmol) in DME (0.2 mL) was added pyrimidin-5-ylboronic acid (37.3 mg, 0.301 mmol), Cs$_2$CO$_3$ (98 mg, 0.301 mmol) and bis(triphenylphosphine)palladium (II) dichloride (6.04 mg, 8.60 μmol). Water (0.1 mL) and ethanol (0.1 mL) were added to make a homogeneous solution. The reaction mixture was stirred at 115° C. for 1.5 h. The reaction mixture was then concentrated in vacuo, and the crude reaction product was dissolved in 20 mL of EtOAc and washed with water. The organic layer was separated and concentrated, and the residue was purified using silica gel column chromatography (hexanes-100% EtOAc) to give the titled compound of step A1 (4 mg, 7.83 μmol, 18% yield). $^1$H NMR (500 MHz, chloroform-d) δ 9.02 (s, 1H), 8.99 (s, 2H), 7.76 (s, 1H), 7.46 (d, J=1.0 Hz, 1H), 7.30 (d, J=1.0 Hz, 1H), 5.91 (d, J=4.3 Hz, 1H), 2.93-2.88 (m, 2H), 2.82-2.73 (m, 2H), 2.70-2.64 (m, 1H), 2.04-1.85 (m, 3H), 1.85-1.76 (m, 1H), 1.56 (s, 9H), 1.45 (s, 9H).

Step 1B. rel-(4aS,11bS)-10-Pyrimidin-5-yl-4,4a,5,6,7,11b-hexahydro-3-thia-1-aza-dibenzo[a,c]cyclohepten-2-ylamine To a solution of the compound of step 1A (55 mg, 0.108 mmol) in dichloromethane (2 mL) was added TFA (1 mL, 12.98 mmol). The mixture was stirred at rt for 3 h. The solvents were removed, and the crude produce was purified by azeotropic drying with toluene to afford a clean product (53 mg, 0.097 mmol, 90% yield). LCMS (M+H)$^+$=331.2. $^1$H NMR (500 MHz, methanol-d$_4$) δ 9.16 (s, 1H), 9.08 (s, 2H), 7.68 (dd, J=7.8, 2.0 Hz, 1H), 7.59-7.52 (m, 1H), 7.43 (d, J=7.9 Hz, 1H), 5.15 (d, J=2.7 Hz, 1H), 3.35 (d, J=2.7 Hz, 1H), 2.99 (t, J=5.5 Hz, 2H), 2.91 (dd, J=12.1, 7.8 Hz, 1H), 2.63 (dt, J=7.9, 4.0 Hz, 1H), 2.12-2.01 (m, 1H), 1.95-1.71 (m, 3H).

Example 1a (4aS,11bS)-10-Pyrimidin-5-yl-4,4a,5,6,7,11b-hexahydro-3-thia-1-aza-dibenzo[a,c]cyclohepten-2-ylamine

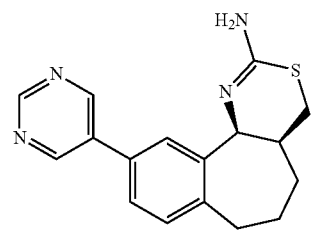 [SMILES: NC1=N[C@@H]2c3cc(-c4cncnc4)ccc3CCC[C@@H]2CS1]

Example 1b (4aR,11bR)-10-Pyrimidin-5-yl-4,4a,5,6,7,11b-hexahydro-3-thia-1-aza-dibenzo[a,c]cyclohepten-2-ylamine

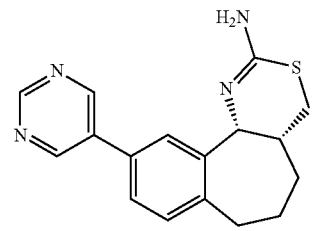 [SMILES: NC1=N[C@H]2c3cc(-c4cncnc4)ccc3CCC[C@H]2CS1]

A sample of the compound of example 1 (racemic) was separated by chiral HPLC under the following conditions: column=Chiralcel OJ 21×250 mm 10 um, flow rate=15 mL/min, isocratic elution of 25% solvent B/80% solvent A, where solvent A=0.1% diethylamine in n-heptane and solvent B=ethanol. The compound of example 1a eluted at 11.5 min and the compound of example 1b eluted at 20.1 min. $^1$H NMR and LCMS data were identical to those reported for the racemic compound of example 1. The absolute configuration of compound 1a was unambiguously determined by X-ray crystallography.

Example 2 rel-(4aS,11bS)-11b-Methyl-10-pyrimidin-5-yl-4,4a,5,6,7,11b-hexahydro-3-thia-1-aza-dibenzo[a,c]cyclohepten-2-ylamine, bis(2,2,2-trifluoroacetate)

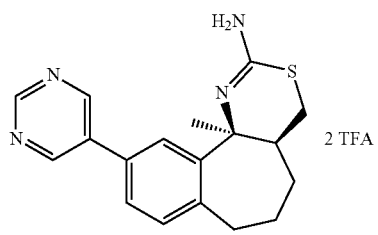 [SMILES: C[C@]12N=C(N)SC[C@H]1CCCc1ccc(-c3cncnc3)cc12]

Step 2A. rel-(4aS,11bS)-11b-Methyl-10-pyrimidin-5-yl-4,4a,5,6,7,11b-hexahydro-3-thia-1-aza-dibenzo[a,c]cyclohepten-2-ylamine, bis-N—N-(tert-butyl) carbamate In a manner similar to that reported for step 1A of example 1, the compound of preparation B was converted to the compound of step 2A in 67% yield. LCMS (M+H)$^+$=525.3. $^1$H NMR (500 MHz, chloroform-d) δ 9.17 (s, 1H), 9.10 (s, 2H), 7.96 (d, J=1.8 Hz, 1H), 7.40 (dd, J=7.8, 2.0 Hz, 1H), 7.27 (d, J=1.0 Hz, 2H), 3.21 (t, J=13.4 Hz, 1H), 2.98-2.85 (m, 2H), 2.66 (dd, J=11.9, 2.4 Hz, 1H), 2.50-2.38 (m, J=13.9, 13.9 Hz, 1H), 2.21-2.12 (m, 1H), 2.11-2.03 (m, J=3.7 Hz, 1H), 1.97-1.86 (m, 1H), 1.84 (s, 3H), 1.64-1.58 (m, J=13.7 Hz, 1H), 1.55 (s, 18H)

Step 2B. rel-(4aS,11bS)-11b-Methyl-10-pyrimidin-5-yl-4,4a,5,6,7,11b-hexahydro-3-thia-1-aza-dibenzo[a,c]cyclohepten-2-ylamine In a manner similar to that reported for step 1B of example 1, the compound of Step 2A was converted to the compound of example 2 in 87% yield. MS (M+H)$^+$=325.1 $^1$H NMR (500 MHz, chloroform-d) δ 9.16 (s, 1H), 8.90 (s, 2H), 7.45-7.38 (m, 2H), 7.31 (d, J=7.6 Hz, 1H), 3.18-3.08 (m, 1H), 2.91 (dd, J=15.1, 5.0 Hz, 1H), 2.83 (t, J=12.4 Hz, 1H), 2.71 (dd, J=11.9, 2.7 Hz, 1H), 2.53-2.36 (m, 2H), 2.08-1.99 (m, 1H), 1.98-1.90 (m, 1H), 1.88 (s, 3H), 1.62-1.49 (m, 1H).

Example 3

5-Chloro-pyridine-2-carboxylic acid (rel-(4aS,11bS)-2-amino-11b-methyl-4,4a,5,6,7,11b-hexahydro-3-thia-1-aza-dibenzo[a,c]cyclohepten-10-yl)-amide, 2,2,2-trifluoroacetate

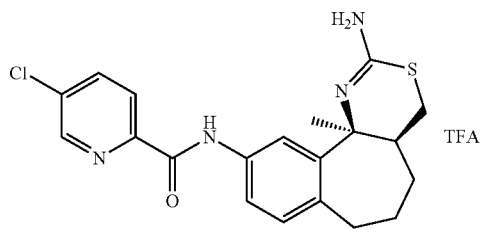 [SMILES: C[C@]12N=C(N)SC[C@H]1CCCc1ccc(NC(=O)c3ccc(Cl)cn3)cc12]

Step 3A. (E)-Methyl 2-(5-chloropicolinamido)-9-methyl-6,7-dihydro-5H-benzo[7]annulene-8-carboxylate To a solution of 5-chloropicolinic acid (354 mg, 2.248 mmol) in dichloromethane (5 mL) was added HATU (940 mg, 2.473 mmol) and DIPEA (0.589 mL, 3.37 mmol). After stirring for 10 min, methyl 2-amino-9-methyl-6,7-dihydro-5H-benzo[7]annulene-8-carboxylate from preparation J, step J1 (260 mg, 1.124 mmol) was added. The mixture was stirred at rt for 4 h. Ethyl acetate (100 mL) was added and the organic layer was washed with water. After concentration of the organic layer, the residue was purified using silica gel column chromatography (hexanes-100% EtOAc) to give methyl 2-(5-chloropicolinamido)-9-methyl-6,7-dihydro-5H-benzo[7]annulene-8-carboxylate (345 mg, 0.930 mmol, 83% yield). LCMS (M+H)$^+$=371.3. $^1$H NMR (400 MHz, chloroform-d) δ 9.84 (s, 1H), 8.56 (dd, J=2.4, 0.6 Hz, 1H), 8.25 (dd, J=8.4, 0.6 Hz, 1H), 7.88 (dd, J=8.4, 2.4 Hz, 1H), 7.73 (d, J=2.3 Hz, 1H), 7.63 (dd, J=8.0, 2.3 Hz, 1H), 7.20 (d, J=8.3 Hz, 1H), 3.82 (s, 3H), 2.55 (t, J=6.5 Hz, 2H), 2.44 (s, 3H), 2.18-2.08 (m, 4H).

Step 3B. (E)-5-Chloro-N-(8-(hydroxymethyl)-9-methyl-6,7-dihydro-5H-benzo[7]annulen-2-yl)picolinamide To a solution of methyl 2-(5-chloropicolinamido)-9-methyl-6,7-dihydro-5H-benzo[7]annulene-8-carboxylate from step 3A (345 mg, 0.930 mmol) in THF (2 mL) was slowly added 1.0 M DIBAL-H/THF (4.65 mL, 4.65 mmol) at −78° C. The mixture was stirred at −78° C. for 4 h and then allowed to warm to rt. Brine was added slowly to quench the reaction. The reaction mixture was then extracted with 3×100 mL of EtOAc and the organic layers were combined, dried over sodium sulfate, and concentrated. The residue was purified using silica gel column chromatography (hexanes-60% EtOAc) to give a clean (E)-5-chloro-N-(8-(hydroxymethyl)-9-methyl-6,7-dihydro-5H-benzo[7]annulen-2-yl)picolinamide (120 mg, 0.350 mmol, 37.6% yield). LCMS (M+H)$^+$=343.2. $^1$H NMR (500 MHz, chloroform-d) δ 9.81 (s, 1H), 8.56 (dd, J=2.3, 0.6 Hz, 1H), 8.25 (dd, J=8.4, 0.6 Hz, 1H), 7.87 (dd, J=8.4, 2.3 Hz, 1H), 7.66 (d, J=2.3 Hz, 1H), 7.55 (dd, J=8.1, 2.3 Hz, 1H), 7.18 (d, J=8.2 Hz, 1H), 4.39 (s, 2H), 2.54 (t, J=7.0 Hz, 2H), 2.14 (s, 3H), 2.10 (quin, J=7.1 Hz, 2H), 2.01-1.95 (m, 2H)

Step 3C. (E)-5-Chloro-N-(8-(chloromethyl)-9-methyl-6,7-dihydro-5H-benzo[7]annulen-2-yl)picolinamide To a solution of 5-chloro-N-(8-(hydroxymethyl)-9-methyl-6,7-dihydro-5H-benzo[7]annulen-2-yl)picolinamide from step 3B (52 mg, 0.15 mmol) in dichloromethane (1 mL) was added methanesulfonylchloride (0.015 mL, 0.20 mmol) and DIPEA (0.048 mL, 0.27 mmol). The mixture was stirred at rt for 20 h. The mixture was subjected to chromatography (hexanes-100% EtOAc) to give 5-chloro-N-(8-(chloromethyl)-9-methyl-6,7-dihydro-5H-benzo[7]annulen-2-yl)picolinamide (30 mg, 0.083 mmol, 55% yield). LCMS (M+H)$^+$=361.2. $^1$H NMR (500 MHz, chloroform-d) δ 9.81 (br. s., 1H), 8.58 (dd, J=2.3, 0.6 Hz, 1H), 8.27 (dd, J=8.4, 0.6 Hz, 1H), 7.90 (dd, J=8.4, 2.3 Hz, 1H), 7.70 (d, J=2.3 Hz, 1H), 7.57 (dd, J=8.1, 2.3 Hz, 1H), 7.20 (d, J=8.1 Hz, 1H), 4.37 (s, 2H), 2.57 (t, J=7.0 Hz, 2H), 2.21 (s, 3H), 2.17 (quin, J=7.1 Hz, 2H), 2.05-1.98 (m, 2H)

Step 3D. 5-Chloro-pyridine-2-carboxylic acid (rel-(4aS,11bS)-2-amino-11b-methyl-4,4a,5,6,7,11b-hexahydro-3-thia-1-aza-dibenzo[a,c]cyclohepten-10-yl)-amide, 2,2,2-trifluoroacetate To a solution of (E)-5-chloro-N-(8-(chloromethyl)-9-methyl-6,7-dihydro-5H-benzo[7]annulen-2-yl)picolinamide from step 3C (30 mg, 0.083 mmol) in ethanol (0.5 mL) was added thiourea (6.32 mg, 0.083 mmol). The mixture was heated to reflux for 3 h. The solvent was removed to give crude (2-(5-chloropicolinamido)-9-methyl-6,7-dihydro-5H-benzo[7]annulen-8-yl)methyl carbamimidothioate hydrochloride (36.3 mg, 0.083 mmol, 100% yield), which was used directly for the next step without purification. To a solution of the crude (2-(5-chloropicolinamido)-9-methyl-6,7-dihydro-5H-benzo[7]annulen-8-yl)methyl carbamimidothioate hydrochloride (36 mg, 0.082 mmol) in TFA (2 mL) was added trifluoromethanesulfonic acid (0.5 mL). The reaction mixture was stirred at rt for 16 h. The mixture was then concentrated and dried by azetropic distillation with toluene. The residue was then dissolved in 1.5 mL of MeOH, and a precipitate was removed by filtration. The mother liquor was purified via HPLC under standard conditions to give 5-chloro-pyridine-2-carboxylic acid (rel-(4aS,11bS)-2-amino-11b-methyl-4,4a,5,6,7,11b-hexahydro-3-thia-1-aza-dibenzo[a,c]cyclohepten-10-yl)-amide, 2,2,2-trifluoroacetate salt (16 mg, 0.030 mmol, 36% yield). LCMS (M+H)$^+$=401.2. $^1$H NMR (500 MHz, methanol-d$_4$) δ 8.72 (br. s., 1H), 8.21 (br. s., 1H), 8.08 (dd, J=8.4, 2.0 Hz, 1H), 7.90 (d, J=2.1 Hz, 1H), 7.58 (dd, J=8.1, 2.1 Hz, 1H), 7.28 (d, J=8.1 Hz, 1H), 3.22-3.10 (m, 1H), 2.99-2.80 (m, 3H), 2.57-2.40 (m, 2H), 2.10 (dd, J=14.7, 3.7 Hz, 1H), 1.90 (dd, J=14.5, 3.5 Hz, 1H), 1.87 (s, 3H), 1.64-1.52 (m, 1H)

Example 3a

5-Chloro-pyridine-2-carboxylic acid ((4aS,11bS)-2-amino-11b-methyl-4,4a,5,6,7,11b-hexahydro-3-thia-1-aza-dibenzo[a,c]cyclohepten-10-yl)-amide

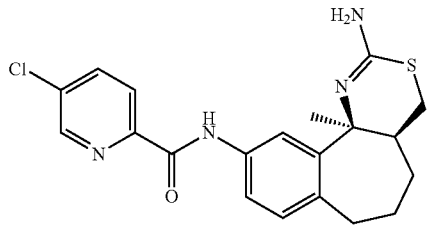 [SMILES: C[C@]12N=C(N)SC[C@H]1CCCc1ccc(NC(=O)c3ccc(Cl)cn3)cc12]

Example 3b

5-Chloro-pyridine-2-carboxylic acid ((4aR,11bR)-2-amino-11b-methyl-4,4a,5,6,7,11b-hexahydro-3-thia-1-aza-dibenzo[a,c]cyclohepten-10-yl)-amide

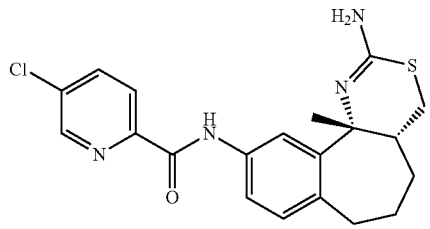 [SMILES: C[C@@]12N=C(N)SC[C@@H]1CCCc1ccc(NC(=O)c3ccc(Cl)cn3)cc12]

A sample of the compound of example 3 (racemic) was separated by chiral HPLC under the following conditions: column=Chiralcel OD 21×250 mm 10 um, flow rate=15 mL/min, isocratic elution of 20% solvent B/80% solvent A, where solvent A=0.1% diethylamine in n-heptane and solvent B=ethanol. The compound of example 3a eluted at 13.4 min and the compound of example 3b eluted at 19.9 min. $^1$H NMR and LCMS data were identical to those reported for the racemic compound of example 3.

Example 4 rel-(4aS,11bS)-8-fluoro-10-pyrimidin-5-yl-4a,5,6,11b-tetrahydro-4H-7-oxa-3-thia-1-aza-dibenzo[a,c]cyclohepten-2-ylamine

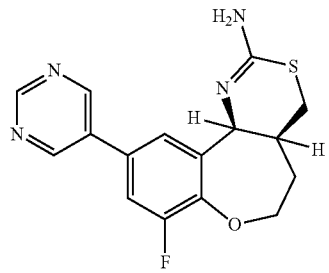 [SMILES: NC1=N[C@@H]2c3cc(-c4cncnc4)cc(F)c3OCC[C@@H]2CS1]

Step 4A. 5-Bromo-3-fluoro-2-hydroxybenzaldehyde

This material was prepared as reported in J. Molecular Catalysis A, 2007, 30-33. Commercial 3-fluoro-2-hydroxybenzaldehyde (0.280 g, 2 mmol) was dissolved in MeCN (10 mL, 191 mmol) and ammonium acetate (0.015 g, 0.200 mmol) and NBS (0.392 g, 2.200 mmol) were added at rt. The mixture was stirred at rt for 1 h. The reaction mixture was then concentrated and the crude compound was dissolved in a small amount of dichloromethane and charged to a 12 g silica gel cartridge which was eluted with a 25 min gradient of from 0% to 30% ethyl acetate in hexanes at 30 mL/min. Fractions containing product were pooled and concentrated in vacuo to give 5-bromo-3-fluoro-2-hydroxybenzaldehyde (0.43 g, 1.963 mmol, 98% yield). $^1$H NMR (400 MHz, chloroform-d) δ ppm 10.89 (s, 1H) 9.87 (s, 1H) 7.39-7.65 (m, 2H).

Step 4B.
5-bromo-2-(but-3-enyloxy)-3-fluorobenzaldehyde

To a solution of 5-bromo-3-fluoro-2-hydroxybenzaldehyde from step 4A (2.0 g, 9.13 mmol) in DMF (36.5 ml) was added 4-bromo-1-butene (3.71 ml, 36.5 mmol) and potassium carbonate (1.58 g, 11.4 mmol). The resulting mixture was stirred at rt overnight. The reaction mixture was diluted with EtOAc (100 mL), washed with water (3×30 mL) and brine (30 mL), dried over magnesium sulfate, and then filtered and concentrated in vacuo. Purification by silica gel column chromatography (0-20% EtOAc/hexanes) gave 5-bromo-2-(but-3-enyloxy)-3-fluorobenzaldehyde (2.38 g, 8.71 mmol, 95% yield). $^1$H NMR (500 MHz, DMSO-d$_6$) δ 10.22 (d, J=0.9 Hz, 1H), 7.98 (dd, J=11.3, 2.4 Hz, 1H), 7.63 (dd, J=2.4, 1.2 Hz, 1H), 5.89 (ddt, J=17.1, 10.4, 6.7 Hz, 1H), 5.17 (dd, J=17.2, 1.7 Hz, 1H), 5.12-5.07 (m, 1H), 4.29 (t, J=6.4 Hz, 1H), 2.57-2.49 (m, 3H).

Step 4C. 2-(but-3-enyloxy)-3-fluoro-5-(pyrimidin-5-yl)benzaldehyde

To a solution of 5-bromo-2-(but-3-enyloxy)-3-fluorobenzaldehyde from step 4B (932 mg, 3.41 mmol) and pyrimidin- 5-ylboronic acid hemihydrate (1.81 g, 13.7 mmol) in DME (15.5 mL), ethanol (7.75 mL), and water (7.75 mL) was added bis(triphenylphosphine)palladium(II) chloride (479 mg, 0.683 mmol) and cesium carbonate (4.44 g, 13.7 mmol). The resulting mixture was brought to 150° C. under microwave irradiation in a sealed tube and stirred for 15 min. The reaction mixture was then cooled and diluted with EtOAc (50 mL), washed with water (2×25 mL), brine (25 mL), dried over magnesium sulfate, filtered and concentrated in vacuo. Purification by silica gel column chromatography (~65% EtOAc/hexanes) gave 2-(but-3-enyloxy)-3-fluoro-5-(pyrimidin-5-yl)benzaldehyde (662 mg, 2.43 mmol, 71% yield). MS (ESI, M+H)$^+$=273.12. $^1$H NMR (500 MHz, DMSO-d6) δ 10.36 (s, 1H), 9.26-9.17 (m, 3H), 8.20 (dd, J=13.0, 2.3 Hz, 1H), 7.95 (d, J=2.4 Hz, 1H), 5.93 (ddt, J=17.2, 10.3, 6.6 Hz, 1H), 5.24-5.09 (m, 2H), 4.37 (td, J=6.1, 1.5 Hz, 2H), 2.57 (q, J=6.4 Hz, 2H).

Step 4D. rel-(4aS,11bS)-8-Fluoro-10-pyrimidin-5-yl-4a,5,6,11b-tetrahydro-4H-7-oxa-3-thia-1-aza-dibenzo[a,c]cyclohepten-2-ylamine To a solution of 2-(but-3-enyloxy)-3-fluoro-5-(pyrimidin-5-yl)benzaldehyde from step 4C (662 mg, 2.43 mmol) in acetonitrile (1.62 ml) and DMF (0.810 ml) was added thiourea (185 mg, 2.43 mmol) and chlorotrimethylsilane (0.311 ml, 2.43 mmol). The resulting mixture was brought to reflux and stirred for 1 h. The reaction mixture was then diluted with EtOAc (10 mL), washed with water (3×2 mL), brine (5 mL), dried over magnesium sulfate, filtered and concentrated in vacuo. Purification by silica gel column chromatography (0-80% EtOAc/hexanes) gave the desired product (3.1 mg, 8.44 μmol, 0.35% yield). $^1$H NMR (500 MHz, methanol-d$_4$) δ 7.63 (d, J=2.1 Hz, 1H), 7.57 (d, J=2.1 Hz, 2H), 6.03 (s, 1H), 5.99 (d, J=10.4 Hz, 1H), 3.12-3.01 (m, J=6.1, 6.1 Hz, 1H), 2.29-2.16 (m, J=4.6 Hz, 1H), 1.82 (d, J=1.2 Hz, 1H), 1.58 (t, J=12.1 Hz, 1H), 1.35 (dd, J=12.5, 3.1 Hz, 1H), 0.62-0.47 (m, 2H), 0.35-0.18 (m, 1H), -0.07--0.31 (m, 1H). MS (ESI, M+H)$^+$=331.16

Example 5 rel-(4aS,10bS)-10b-Methyl-9-(pyrimidin-5-yl)-4a,5,6,10b-tetrahydro-4H-naphtho[1,2-d][1,3]thiazin-2-amine, bis(2,2,2-trifluoroacetate)

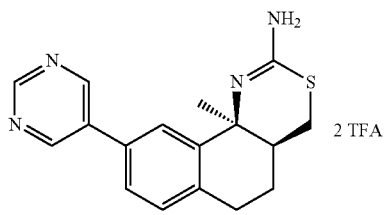 [SMILES: C[C@]12N=C(N)SC[C@H]1CCc1ccc(-c3cncnc3)cc12]

Step 5A. rel-(4aS,10bS)-9-Bromo-10b-methyl-4a,5,6,10b-tetrahydro-4H-naphtho[1,2-d][1,3]thiazin-2-amine-bis-N,N-((tert-butyl)carbamate A mixture of 1,2-dimethoxyethane (5 mL), water (2.5 mL), and ethanol (2 mL) was purged with nitrogen gas for 15 min. The degassed solvent was transferred to a vial charged with a mixture of the tert-butyl rel-((4a,5,10bS)-9-bromo-10b-methyl-4a,5,6,10b-tetrahydro-4H-naphtho[1,2-d][1,3]thiazin-2-yl)carbamate from preparation C (161 mg, 0.391 mmol), pyrimidin-5-ylboronic acid (388 mg, 3.13 mmol), bis(triphenylphosphine)palladium(II) chloride (54.9 mg, 0.078 mmol), and cesium carbonate (1.14 g, 3.52 mmol). The vial was capped and heated to 100° C. for 20 min. The reaction mixture was cooled, diluted with water, and extracted with ethyl acetate. The combined organic layers were dried over sodium sulfate, filtered and concentrated in vacuo. Di-tert-butyl dicarbonate (0.272 mL, 1.173 mmol), triethylamine (0.218 mL, 1.564 mmol), and N,N-dimethylpyridin-4-amine (2.388 mg, 0.020 mmol) were sequentially added to a solution of the coupling reaction product mixture in THF (20 mL). The reaction mixture was allowed to stir for 20 hours and then it was concentrated in vacuo. The residue was purified using silica gel column chromatography (20:1 hexane/EtOAc) to afford rel-(4aS,10bS)-9-bromo-10b-methyl-4a,5,6,10b-tetrahydro-4H-naphtho[1,2-d][1,3]thiazin-2-amine-bis-N,N-((tert-butyl)carbamate (89 mg, 0.174 mmol, 45% yield) as a clear viscous oil. $^1$H NMR (500 MHz, chloroform-d) δ 9.16 (s, 1H), 8.95 (s, 2H), 7.91 (d, J=1.8 Hz, 1H), 7.37 (dd, J=7.9, 2.0 Hz, 1H), 7.21 (d, J=7.9 Hz, 1H), 3.31 (dd, J=12.8, 3.5 Hz, 1H), 3.04-2.84 (m, 3H), 2.20-2.09 (m, 1H), 2.06-1.96 (m, 2H), 1.65 (s, 3H), 1.38 (s, 18H).

Step 5B. rel-(4aS,10bS)-10b-Methyl-9-(pyrimidin-5-yl)-4a,5,6,10b-tetrahydro-4H-naphtho[1,2-d][1,3]thiazin-2-amine, bis(2,2,2-trifluoroacetate)

Trifluoroacetic acid (1 mL) was added to a solution of rel-(4aS,10bS)-9-bromo-10b-methyl-4a,5,6,10b-tetrahydro-4H-naphtho[1,2-d][1,3]thiazin-2-amine-bis-N,N-((tert-butyl)carbamate from step 5A (0.089 g, 0.174 mmol) in dichloromethane (5 mL) at rt. The reaction mixture was allowed to stir at rt for 20 hours. The reaction mixture was concentrated under reduced pressure. The residue was purified using reverse phase preparatory HPLC (SunFire PrepC18 OBD 10 μm, 50×250 mm column, 90% MeOH/10% water/0.1% TFA-90% MeOH/10% water/0.1% TFA, linear gradient over 34 min, 50 ml/min) to afford rel-(4aS,10bS)-10b-methyl-9-(pyrimidin-5-yl)-4a,5,6,10b-tetrahydro-4H-naphtho[1,2-d][1,3]thiazin-2-amine, 2 TFA (53 mg, 0.096 mmol, 55% yield) as a clear solid residue. LCMS (M+H)$^+$=311.1. $^1$H NMR (500 MHz, methanol-d$_4$) δ 9.14 (s, 1H), 9.10 (s, 2H), 7.91 (d, J=1.7 Hz, 1H), 7.64 (dd, J=7.9, 1.8 Hz, 1H), 7.37 (d, J=7.9 Hz, 1H), 3.47 (dd, J=13.3, 3.5 Hz, 1H), 3.15 (dd, J=13.3, 7.8 Hz, 1H), 3.01 (t, J=6.8 Hz, 2H), 2.54 (tt, J=7.5, 3.5 Hz, 1H), 2.25 (dtd, J=14.0, 6.9, 3.4 Hz, 1H), 2.05 (dq, J=14.0, 7.0 Hz, 1H), 1.82 (s, 3H).

Example 6 rel-(4aS,10bS)-9-(5-Chloropyridin-3-yl)-10b-methyl-4a,5,6,10b-tetrahydro-4H-naphtho[1,2-d][1,3]thiazin-2-amine bis(2,2,2-trifluoroacetate)

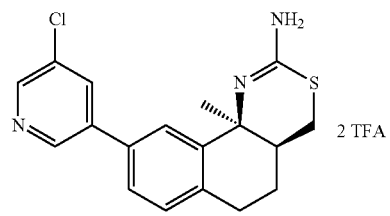 [SMILES: C[C@]12N=C(N)SC[C@H]1CCc1ccc(-c3cncc(Cl)c3)cc12]

A mixture of 1,2-dimethoxyethane (5 mL), water (2.5 mL), and ethanol (2 mL) was purged with nitrogen for 15 min. The degassed solvent was transferred to a vial charged with a mixture of the aryl bromide tert-butyl rel-((4aS,10bS)-9-bromo-10b-methyl-4a,5,6,10b-tetrahydro-4H-naphtho[1,2-d][1,3]thiazin-2-yl)carbamate from preparation C (80 mg, 0.194 mmol), (5-chloropyridin-3-yl)boronic acid (122 mg, 0.778 mmol), bis(triphenylphosphine)palladium(II) chloride (27.3 mg, 0.039 mmol), and cesium carbonate (285 mg, 0.875 mmol). The vial was capped and heated to 100° C. for 20 min. The reaction was cooled, diluted with water, and extracted with EtOAc. The organic layer was dried over sodium sulfate, filtered and concentrated in vacuo. The crude products were dissolved in dichloromethane (5.00 mL). TFA (1.0 mL) was added at rt and the mixture was allowed to stir at rt for 20 hours. The reaction mixture was concentrated under reduced pressure. The residue was purified using reverse phase preparatory HPLC (SunFire PrepC18 OBD 10 μm, 50×250 mm column, 90% MeOH/10% water/0.1% TFA-90% MeOH/10% water/0.1% TFA, linear gradient over 34 min, 50 ml/min) to afford rel-(4aS,10bS)-9-(5-chloropyridin-3-yl)-10b-methyl-4a,5,6,10b-tetrahydro-4H-naphtho[1,2-d][1,3]thiazin-2-amine, 2 TFA (37 mg, 0.063 mmol, 33% yield) as a clear residue. LCMS (M+H)$^+$=344.1. $^1$H NMR (500 MHz, methanol-d$_4$) δ 8.81 (br. s., 1H), 8.58 (br. s., 1H), 8.23 (s, 1H), 7.96-7.73 (m, 1H), 7.61 (dd, J=7.9, 1.7 Hz, 1H), 7.35 (d, J=7.9 Hz, 1H), 3.47 (dd, J=13.3, 3.2 Hz, 1H), 3.15 (dd, J=13.2, 7.7 Hz, 1H), 3.08-2.86 (m, 2H), 2.62-2.40 (m, 1H), 2.25 (td, J=6.9, 3.2 Hz, 1H), 2.05 (dq, J=14.0, 6.9 Hz, 1H), 1.81 (s, 3H).

Example 7 rel-N-((4aS,10bS)-2-Amino-10b-methyl-4a,5,6,10b-tetrahydro-4H-naphtho[1,2-d][1,3]thiazin-9-yl)-5-chloropicolinamide, 2,2,2-trifluoroacetate

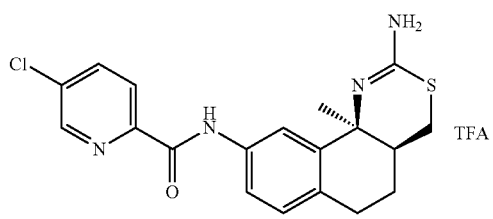 [SMILES: C[C@]12N=C(N)SC[C@H]1CCc1ccc(NC(=O)c3ccc(Cl)cn3)cc12]

HATU (164 mg, 0.432 mmol) and DIEA (0.090 mL, 0.518 mmol) were sequentially added to a mixture of tert-butyl rel-((4aS,10bS)-9-amino-10b-methyl-4a,5,6,10b-tetrahydro-4H-naphtho[1,2-d][1,3]thiazin-2-yl)carbamate from preparation D (60 mg, 0.173 mmol), and 5-chloropicolinic acid (54.4 mg, 0.345 mmol) in DCM (5.0 mL). The resulting mixture was left to stir at rt for 20 h. The mixture was poured into aqueous saturated sodium bicarbonate solution (3 mL) and extracted with EtOAc (2×3 mL). The combined organics were washed with brine (1 mL), dried (sodium sulfate), filtered, and concentrated in vacuo. The residue was dissolved in DCM (5.0 mL) and TFA (1.0 mL, 13.0 mmol. The resulting mixture was allowed to stir at rt for 2 h and concentrated in vacuo. The crude product was purified using reverse phase preparatory HPLC (SunFire PrepC18 OBD 10 mm, 50×250 mm column, 90% MeOH/10% water/0.1% TFA-90% MeOH/10% water/0.1% TFA, linear gradiant over 34 min, 50 ml/min) to afford rel-N-((4aS,10bS)-2-amino-10b-methyl-4a,5,6,10b-tetrahydro-4H-naphtho[1,2-d][1,3]thiazin-9-yl)-5-chloropicolinamide, TFA (45 mg, 0.088 mmol, 51% yield). LCMS (M+H)$^+$=387.1. $^1$H NMR (500 MHz, methanol-d$_4$) δ 8.70 (d, J=1.8 Hz, 1H), 8.28-8.16 (m, J=8.4 Hz, 1H), 8.11-8.01 (m, 2H), 7.61 (dd, J=8.2, 2.1 Hz, 1H), 7.29-7.15 (m, J=8.4 Hz, 1H), 3.50 (dd, J=13.1, 3.7 Hz, 1H), 3.14 (dd, J=13.1, 7.3 Hz, 1H), 2.95 (t, J=6.8 Hz, 2H), 2.51 (tt, J=7.6, 3.6 Hz, 1H), 2.20 (dtd, J=13.8, 6.7, 3.4 Hz, 1H), 2.00 (dq, J=14.2, 7.2 Hz, 1H), 1.78 (s, 3H).

Example 7a

N-((4aR,10bR)-2-Amino-10b-methyl-4a,5,6,10b-tetrahydro-4H-naphtho[1,2-d][1,3]thiazin-9-yl)-5-chloropicolinamide

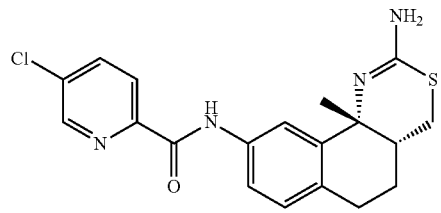 [SMILES: C[C@@]12N=C(N)SC[C@@H]1CCc1ccc(NC(=O)c3ccc(Cl)cn3)cc12]

Example 7b

N-((4aS,10bS)-2-Amino-10b-methyl-4a,5,6,10b-tetrahydro-4H-naphtho[1,2-d][1,3]thiazin-9-yl)-5-chloropicolinamide

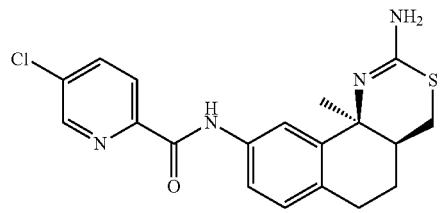 [SMILES: C[C@]12N=C(N)SC[C@H]1CCc1ccc(NC(=O)c3ccc(Cl)cn3)cc12]

A sample of the compound of example 7 (racemic) was separated using chiral HPLC under the following conditions: column=Chiralcel OJ 21×250 mm 10 u, flow rate=15 mL/min, isocratic elution of 40% solvent B/60% solvent A, where solvent A=0.1% diethylamine in n-heptane and solvent B=ethanol. The compound of Example 7a eluted at 8.4 min and the compound of example 7b eluted at 11.5 min. $^1$H NMR and LCMS data were identical to those reported for the racemic compound of example 7.

Example 8 rel-N-((4aS,10bS)-2-Amino-10b-methyl-4a,5,6,10b-tetrahydro-4H-naphtho[1,2-d][1,3]thiazin-9-yl)-3,5-difluoropicolinamide, 2,2,2-trifluoroacetate

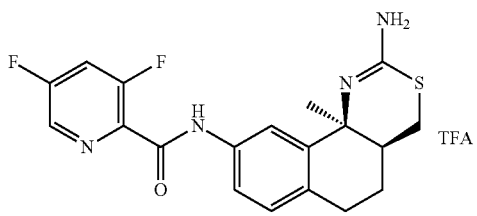 [SMILES: C[C@]12N=C(N)SC[C@H]1CCc1ccc(NC(=O)c3ncc(F)cc3F)cc12]

In a manner similar to the two-step procedure used for the preparation of example 7, but using tert-butyl rel-((4aS,10bS)-9-amino-10b-methyl-4a,5,6,10b-tetrahydro-4H-naphtho[1,2-d][1,3]thiazin-2-yl)carbamate from preparation D (60 mg, 0.173 mmol) and 3,5-difluoropicolinic acid (54.9 mg, 0.345 mmol) as starting materials, the titled compound of Example 8 (46 mg, 0.090 mmol, 52% yield) was prepared as a white solid. LCMS (M+H)$^+$=398.1. $^1$H NMR (500 MHz, methanol-d$_4$) δ 8.51 (d, J=2.1 Hz, 1H), 8.07 (d, J=2.1 Hz, 1H), 7.80 (ddd, J=10.7, 8.6, 2.4 Hz, 1H), 7.54 (dd, J=8.2, 2.1 Hz, 1H), 7.22 (d, J=8.2 Hz, 1H), 3.50 (dd, J=13.2, 3.7 Hz, 1H), 3.14 (dd, J=13.2, 7.4 Hz, 1H), 2.95 (t, J=6.8 Hz, 2H), 2.51 (tt, J=7.5, 3.6 Hz, 1H), 2.21 (dtd, J=13.8, 6.8, 3.5 Hz, 1H), 2.00 (dq, J=14.2, 7.1 Hz, 1H), 1.78 (s, 3H).

Example 9 rel-N-((4aS,10bS)-2-amino-10b-methyl-4a,5,6,10b-tetrahydro-4H-naphtho[1,2-d][1,3]thiazin-9-yl)-5-fluoropicolinamide, 2,2,2-trifluoroacetate

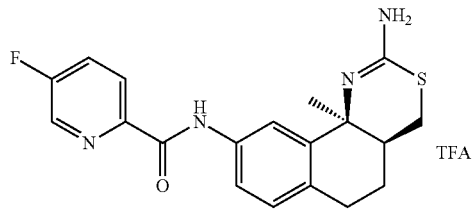 [SMILES: C[C@]12N=C(N)SC[C@H]1CCc1ccc(NC(=O)c3ccc(F)cn3)cc12]

In a manner similar to the two-step procedure used for the preparation of example 7, but using tert-butyl rel-((4aS,10bS)-9-amino-10b-methyl-4a,5,6,10b-tetrahydro-4H-naphtho[1,2-d][1,3]thiazin-2-yl)carbamate from preparation D (60 mg, 0.173 mmol) and 5-fluoropicolinic acid as starting materials, the titled compound of example 9 (51 mg, 0.10 mmol, 60% yield) was prepared as a white solid. LCMS (M+H)$^+$=371.1. $^1$H NMR (500 MHz, methanol-d$_4$) δ 8.61 (d, J=2.7 Hz, 1H), 8.30 (dd, J=8.7, 4.6 Hz, 1H), 8.14-8.03 (m, 1H), 7.82 (td, J=8.5, 2.7 Hz, 1H), 7.60 (dd, J=8.2, 2.1 Hz, 1H), 7.23 (d, J=8.2 Hz, 1H), 3.52 (dd, J=13.2, 3.7 Hz, 1H), 3.15 (dd, J=13.3, 7.2 Hz, 1H), 2.95 (t, J=6.8 Hz, 2H), 2.51 (tt, J=7.6, 3.6 Hz, 1H), 2.19 (dtd, J=13.7, 6.7, 3.6 Hz, 1H), 2.07-1.95 (m, 1H), 1.79 (s, 3H).

Example 10 rel-(4aS,10bS)-9-Bromo-10b-methyl-4a,5,6,10b-tetrahydro-4H-naphtho[1,2-d][1,3]thiazin-2-amine

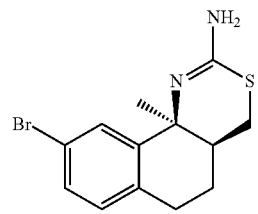 [SMILES: C[C@]12N=C(N)SC[C@H]1CCc1ccc(Br)cc12]

A sample of the crude intermediate from preparation C, step C3 was recrystallized from ethyl acetate to afford rel-(4aS,10bS)-9-bromo-10b-methyl-4a,5,6,10b-tetrahydro-4H-naphtho[1,2-d][1,3]thiazin-2-amine as a white crystalline solid. LCMS (M+H)$^+$=313.0. $^1$H NMR (500 MHz, chloroform-d) δ 7.77 (d, J=2.0 Hz, 1H), 7.35 (dd, J=8.2, 2.0 Hz, 1H), 6.97 (d, J=8.2 Hz, 1H), 3.06 (dd, J=12.8, 10.1 Hz, 1H), 2.96 (dd, J=13.0, 3.4 Hz, 1H), 2.89-2.77 (m, 2H), 2.41-2.30 (m, 2H), 2.05-1.97 (m, 1H), 1.75 (s, 3H).

Example 11 rel-(4aS,11bS)-10-(5-methoxypyridin-3-yl)-11b-methyl-4,4a,5,6,7,11b-hexahydrobenzo[6,7]cyclohepta[1,2-d][1,3]thiazin-2-amine, bis(2,2,2-trifluoroacetate)

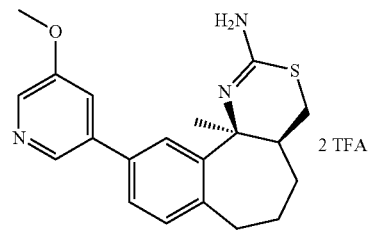 [SMILES: COc1cncc(-c2ccc3c(c2)[C@@]2(C)N=C(N)SC[C@H]2CCC3)c1]

In a manner similar to the two-step procedure used for the preparation of example 6, but using tert-butyl rel-((4aS,11bS)-10-bromo-11b-methyl-4,4a,5,6,7,11b-hexahydrobenzo[6,7]cyclohepta[1,2-d][1,3]thiazin-2-yl)carbamate from preparation E (28 mg, 0.066 mmol) and (5-methoxypyridin-3-yl)boronic acid (81 mg, 0.527 mmol) as starting materials, the titled compound of example 11 (13 mg, 0.0.22 mmol, 33% yield) was prepared as clear residue. LCMS (M+H)$^+$=354.1. $^1$H NMR (500 MHz, methanol-d$_4$) δ 8.55 (br. s., 1H), 8.45 (br. s., 1H), 8.02-7.92 (m, 1H), 7.67 (dd, J=7.8, 2.0 Hz, 1H), 7.47 (d, J=7.8 Hz, 1H), 7.44 (d, J=2.0 Hz, 1H), 3.28-3.20 (m, 1H), 3.04-2.95 (m, 2H), 2.83 (t, J=12.4 Hz, 1H), 2.61-2.47 (m, 2H), 2.12 (dd, J=14.6, 3.6 Hz, 1H), 2.01-1.92 (m, 1H), 1.91 (s, 3H), 1.72-1.56 (m, 1H).

Example 12 rel-(4aS,11bS)-10-(3-methoxyphenyl)-11b-methyl-4,4a,5,6,7,11b-hexahydrobenzo[6,7]cyclohepta[1,2-d][1,3]thiazin-2-amine, 2,2,2-trifluoroacetate

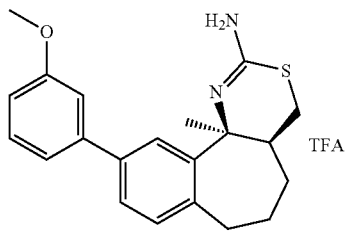 [SMILES: COc1cccc(-c2ccc3c(c2)[C@@]2(C)N=C(N)SC[C@H]2CCC3)c1]

In a manner similar to the two-step procedure used for the preparation of example 6, but using tert-butyl rel-((4aS,11bS)-10-bromo-11b-methyl-4,4a,5,6,7,11b-hexahydrobenzo[6,7]cyclohepta[1,2-d][1,3]thiazin-2-yl)carbamate from preparation E (28 mg, 0.066 mmol) and (3-methoxyphenyl)boronic acid (80 mg, 0.527 mmol) as starting materials, the titled compound of example 12 (10 mg, 0.021 mmol, 33% yield) was prepared as clear residue. LCMS (M+H)$^+$=353.1. $^1$H NMR (500 MHz, methanol-d$_4$) δ 7.50 (dd, J=7.7, 1.9 Hz, 1H), 7.37-7.29 (m, 3H), 7.16-7.11 (m, 1H), 7.11-7.05 (m, 1H), 6.96-6.88 (m, 1H), 3.84 (s, 3H), 3.24-3.13 (m, 1H), 3.00-2.88 (m, 2H), 2.82 (t, J=12.4 Hz, 1H), 2.58-2.40 (m, 2H), 2.09 (dd, J=14.7, 3.7 Hz, 1H), 1.91 (dt, J=14.4, 3.1 Hz, 1H), 1.88 (s, 3H), 1.60 (q, J=13.9 Hz, 1H).

Example 13 rel-(4aS,11bS)-10-(5-Chloropyridin-3-yl)-11b-methyl-4,4a,5,6,7,11b-hexahydrobenzo[6,7]cyclohepta[1,2-d][1,3]thiazin-2-amine, bis(2,2,2-trifluoroacetate)

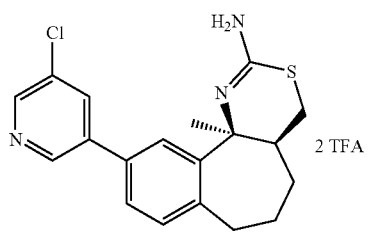 [SMILES: C[C@]12N=C(N)SC[C@H]1CCCc1ccc(-c3cncc(Cl)c3)cc12]

In a manner similar to the two-step procedure used for the preparation of example 6, but using tert-butyl rel-(4aS,11bS)-10-bromo-11b-methyl-4,4a,5,6,7,11b-hexahydrobenzo[6,7]cyclohepta[1,2-d][1,3]thiazin-2-yl)carbamate from preparation E (28 mg, 0.066 mmol) and (5-chloropyridin-3-yl)boronic acid (83 mg, 0.527 mmol) as starting materials, the titled compound of example 13 (19 mg, 0.032 mmol, 48% yield) was prepared as clear residue. LCMS (M+H)$^+$=358.1. $^1$H NMR (500 MHz, methanol-d$_4$) δ 8.77-8.64 (m, 1H), 8.57 (d, J=1.8 Hz, 1H), 8.09 (t, J=2.1 Hz, 1H), 7.59 (dd, J=7.8, 2.0 Hz, 1H), 7.43 (d, J=7.8 Hz, 1H), 7.36 (d, J=2.0 Hz, 1H), 3.26-3.17 (m, 1H), 3.01-2.92 (m, 2H), 2.81 (t, J=12.4 Hz, 1H), 2.59-2.44 (m, 2H), 2.10 (dd, J=14.6, 3.7 Hz, 1H), 1.97-1.91 (m, 1H), 1.89 (s, 3H), 1.62 (q, J=13.8 Hz, 1H).

Example 14 rel-(4aS,11bS)-10-(5-fluoropyridin-3-yl)-11b-methyl-4,4a,5,6,7,11b-hexahydrobenzo[6,7]cyclohepta[1,2-d][1,3]thiazin-2-amine, bis(2,2,2-trifluoroacetate)

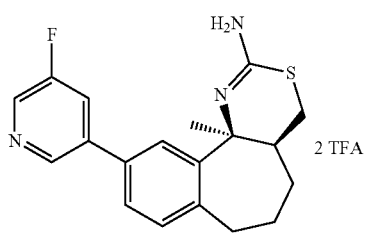 [SMILES: C[C@]12N=C(N)SC[C@H]1CCCc1ccc(-c3cncc(F)c3)cc12]

In a manner similar to the two-step procedure used for the preparation of example 6, but using tert-butyl rel-(4aS,11bS)-10-bromo-11b-methyl-4,4a,5,6,7,11b-hexahydrobenzo[6,7]cyclohepta[1,2-d][1,3]thiazin-2-yl)carbamate from preparation E (28 mg, 0.066 mmol) and (5-fluoropyridin-3-yl)boronic acid (74.2 mg, 0.527 mmol) as starting materials, the titled compound of example 14 (13 mg, 0.022 mmol, 34% yield) was prepared as clear residue. LCMS (M+H)$^+$=342.1. $^1$H NMR (500 MHz, methanol-d$_4$) δ 8.64 (br. s., 1H), 8.49 (br. s., 1H), 7.90-7.82 (m, 1H), 7.61 (dd, J=7.8, 2.0 Hz, 1H), 7.43 (d, J=7.8 Hz, 1H), 7.37 (d, J=1.8 Hz, 1H), 3.26-3.18 (m, 1H), 3.01-2.93 (m, 2H), 2.81 (t, J=12.4 Hz, 1H), 2.59-2.41 (m, 2H), 2.16-2.05 (m, 1H), 1.98-1.90 (m, 1H), 1.89 (s, 3H), 1.69-1.54 (m, 1H).

Example 15 rel-(4aS,11bS)-11b-Methyl-10-(5-(prop-1-yn-1-yl)pyridin-3-yl)-4,4a,5,6,7,11b-hexahydrobenzo[6,7]cyclohepta[1,2-d][1,3]thiazin-2-amine, bis(2,2,2-trifluoroacetate)

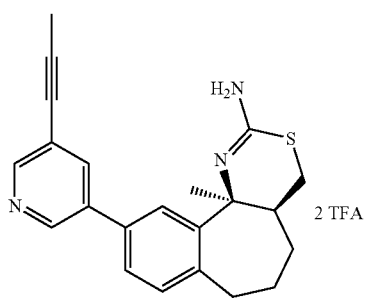 [SMILES: CC#Cc1cncc(-c2ccc3c(c2)[C@@]2(C)N=C(N)SC[C@H]2CCC3)c1]

In a manner similar to the two-step procedure used for the preparation of example 6, but using tert-butyl rel-((4aS,11bS)-10-bromo-11b-methyl-4,4a,5,6,7,11b-hexahydrobenzo[6,7]cyclohepta[1,2-d][1,3]thiazin-2-yl)carbamate from preparation E (28 mg, 0.066 mmol) and (5-(prop-1-yn-1-yl)pyridin-3-yl)boronic acid (85 mg, 0.527 mmol) as starting materials, the titled compound of example 15 (10 mg, 0.016 mmol, 25% yield) was prepared as clear residue. LCMS (M+H)$^+$=362.1. $^1$H NMR (500 MHz, methanol-d$_4$) δ

8.70 (br. s., 1H), 8.57 (br. s., 1H), 8.09 (t, J=1.9 Hz, 1H), 7.58 (dd, J=7.8, 2.0 Hz, 1H), 7.43 (d, J=7.8 Hz, 1H), 7.35 (d, J=2.0 Hz, 1H), 3.22 (t, J=13.6 Hz, 1H), 3.03-2.92 (m, 2H), 2.81 (t, J=12.4 Hz, 1H), 2.61-2.41 (m, 2H), 2.16-2.04 (m, 1H), 2.10 (s, 3H), 1.99-1.85 (m, 1H), 1.89 (s, 3H), 1.62 (q, J=13.9 Hz, 1H).

Example 16 rel-(4aS,11bS)-11b-Methyl-10-(5-(prop-1-yn-1-yl)pyridin-3-yl)-4,4a,5,6,7,11b-hexahydrobenzo[6,7]cyclohepta[1,2-d][1,3]thiazin-2-amine, bis(2,2,2-trifluoroacetate)

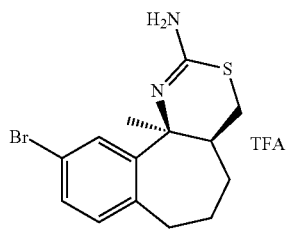 [SMILES: C[C@]12N=C(N)SC[C@H]1CCCc1ccc(Br)cc12]

Prepared as described in preparation E, step E4. LCMS (M+H)+ 327.0. ¹H NMR (500 MHz, methanol-d₄) δ 7.43 (dd, J=8.1, 2.1 Hz, 1H), 7.26 (d, J=2.1 Hz, 1H), 7.20 (d, J=8.1 Hz, 1H), 3.17-3.06 (m, 1H), 2.96 (dd, J=12.1, 3.1 Hz, 1H), 2.89 (dd, J=15.4, 5.6 Hz, 1H), 2.80 (t, J=12.4 Hz, 1H), 2.57-2.39 (m, 2H), 2.08 (dd, J=14.8, 4.0 Hz, 1H), 1.94-1.86 (m, 1H), 1.84 (s, 3H), 1.67-1.48 (m, 1H).

Example 17 rel-(4aR,10bS)-8-Fluoro-10b-methyl-9-(pyrimidin-5-yl)-4,4a,5,10b-tetrahydrochromeno[4,3-d][1,3]thiazin-2-amine, bis(2,2,2-trifluoroacetate)

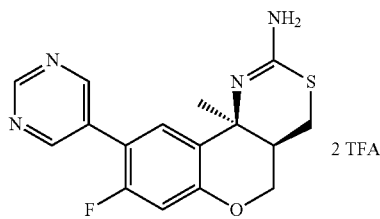 [SMILES: C[C@]12N=C(N)SC[C@H]1COc1cc(F)c(-c3cncnc3)cc12]

In a manner similar to the two-step procedure used for the preparation of example 6, but using tert-butyl rel-((4aR,10bS)-9-bromo-8-fluoro-10b-methyl-4,4a,5,10b-tetrahydrochromeno[4,3-d][1,3]thiazin-2-yl)carbamate preparation F (50 mg, 0.116 mmol) from and pyrimidin-5-ylboronic acid (115 mg, 0.927 mmol) as starting materials, the titled compound of Example 17 (26 mg, 0.045 mmol, 39% yield) was prepared as a clear residue. LCMS (M+H)+=331.1. ¹H NMR (500 MHz, methanol-d₄) δ 7.89 (br. s., 1H), 7.75 (br. s., 2H), 6.51 (d, J=8.2 Hz, 1H), 5.57 (d, J=11.7 Hz, 1H), 3.32 (dd, J=12.1, 2.9 Hz, 1H), 3.10 (dd, J=12.0, 5.7 Hz, 1H), 2.24 (dd, J=13.7, 3.7 Hz, 1H), 1.99 (dd, J=13.6, 8.4 Hz, 1H), 1.46-1.36 (m, 1H), 0.59 (s, 3H).

Example 18 rel-N-((4aR,10bS)-2-Amino-8-fluoro-10b-methyl-4,4a,5,10b-tetrahydrochromeno[4,3-d][1,3]thiazin-9-yl)-5-chloropicolinamide, 2,2,2-trifluoroacetate

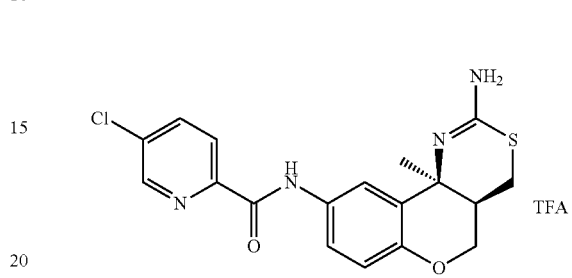

In a manner similar to the two-step procedure used for the preparation of example 7, but using tert-butyl rel-((4aR,10bS)-9-amino-8-fluoro-10b-methyl-4,4a,5,10b-tetrahydrochromeno[4,3-d][1,3]thiazin-2-yl)carbamate from preparation G (100 mg, 0.272 mmol) and 5-chloropicolinic acid (86 mg, 0.544 mmol) as starting materials, the titled compound of Example 18 (40 mg, 0.075 mmol, 28% yield) was prepared as a white solid. LCMS (M+H)+=407.1. ¹H NMR (500 MHz, methanol-d₄) δ 8.73 (dd, J=2.3, 0.6 Hz, 1H), 8.29 (d, J=8.4 Hz, 1H), 8.23 (dd, J=8.4, 0.6 Hz, 1H), 8.11 (dd, J=8.4, 2.4 Hz, 1H), 6.83 (d, J=11.4 Hz, 1H), 4.56 (dd, J=11.7, 2.9 Hz, 1H), 4.31 (dd, J=11.8, 6.2 Hz, 1H), 3.54 (dd, J=13.6, 4.0 Hz, 1H), 3.28 (dd, J=13.7, 7.9 Hz, 1H), 2.68 (tt, J=6.8, 3.6 Hz, 1H), 1.85 (s, 3H).

Example 19 rel-(4aS,10bS)-10b-Methyl-9-(1H-pyrazol-4-yl)-4a,5,6,10b-tetrahydro-4H-naphtho[1,2-d][1,3]thiazin-2-amine, bis(2,2,2-trifluoroacetate)

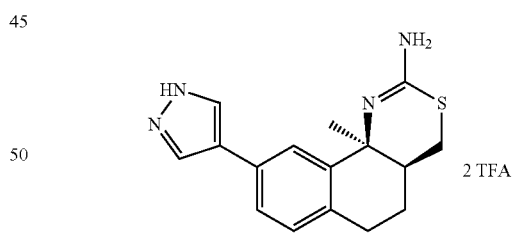

Step 19A. tert-Butyl rel-((4aS,10bS)-10b-methyl-9-(1H-pyrazol-4-yl)-4a,5,6,10b-tetrahydro-4H-naphtho[1,2-d][1,3]thiazin-2-yl)carbamate Dioxane (1 mL) and water (0.1 mL) were added to a mixture of tert-butyl rel-((4aS,10bS)-9-bromo-10b-methyl-4a,5,6,10b-tetrahydro-4H-naphtho[1,2-d][1,3]thiazin-2-yl)carbamate from preparation C (10 mg, 0.024 mmol), (1H-pyrazol-4-yl)boronic acid (27.2 mg, 0.243 mmol) and potassium carbonate (33.6 mg, 0.243 mmol). Nitrogen was bubbled through the mixture for 5 min. 1,1'-Bis(diphenylphosphino)ferrocenepalladium (II) dichloride, toluene (10 mg, 0.012 mmol) was added and the resulting mixture was heated at 100° C. for 1 h. The reaction contents were cooled to rt and were transferred to a separatory funnel containing saturated aqueous NaHCO$_3$ solution (10 mL). The aqueous layer was extracted with EtOAc (3×25 mL). The combined organic layers were washed with brine (10 mL), dried over sodium sulfate, filtered and concentrated. The crude product of step 19A was used in the next step without further purification. LCMS (M+H)$^+$=399.08.

Step 19B. rel-(4aS,10bS)-10b-Methyl-9-(1H-pyrazol-4-yl)-4a,5,6,10b-tetrahydro-4H-naphtho[1,2-d][1,3]thiazin-2-amine, bis(2,2,2-trifluoroacetate)

Trifluoroacetic acid (0.1 ml, 1.3 mmol) was added to a solution of tert-butyl rel-((4aS,10bS)-10b-methyl-9-(1H-pyrazol-4-yl)-4a,5,6,10b-tetrahydro-4H-naphtho[1,2-d][1,3]thiazin-2-yl)carbamate (10 mg, 0.025 mmol) from step 19A in DCM (1 mL). The reaction mixture was stirred at rt for 3 h. The reaction was evaporated to dryness under reduced pressure. The crude residue was purified by Prep HPLC column chromatography (Luna Axia C18, 10 μm, 30×100 mm column, 90% MeOH/10% water/0.1% TFA-90% MeOH/10% water/0.1% TFA, linear gradiant over 20 min, 40 mL/min) to afford the titled compound of example 19 (6.3 mg, 0.012 mmol, 47% yield). LCMS (M+H)$^+$=299.11. $^1$H NMR (500 MHz, methanol-d$_4$) δ 8.01 (s, 2H), 7.75 (s, 1H), 7.52 (dd, J=7.9, 1.8 Hz, 1H), 7.21 (d, J=8.1 Hz, 1H), 3.54 (dd, J=13.2, 3.6 Hz, 1H), 3.18 (dd, J=13.2, 7.1 Hz, 1H), 2.96 (t, J=6.7 Hz, 2H), 2.53 (dt, J=7.8, 3.7 Hz, 1H), 2.28-2.14 (m, 1H), 2.02 (dd, J=13.9, 7.8 Hz, 1H), 1.82 (s, 3H).

Example 20 rel-(4aS,10bS)-9-(1,3-Dimethyl-1H-pyrazol-5-yl)-10b-methyl-4a,5,6,10b-tetrahydro-4H-naphtho[1,2-d][1,3]thiazin-2-amine, bis(2,2,2-trifluoroacetate)

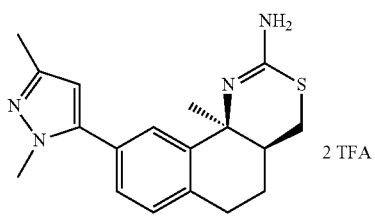 [SMILES: Cc1cc(-c2ccc3c(c2)[C@@]2(C)N=C(N)SC[C@H]2CC3)n(C)n1]

In a manner similar to the two step procedure described for example 19, the compound of preparation C was converted to the compound of example 20 in 83% overall yield. LCMS (M+H)$^+$ 327.13. $^1$H NMR (500 MHz, methanol-d$_4$) δ 7.64 (d, J=1.7 Hz, 1H), 7.42 (dd, J=7.9, 1.8 Hz, 1H), 7.35 (d, J=7.9 Hz, 1H), 6.27 (s, 1H), 3.84 (s, 3H), 3.46 (dd, J=13.1, 3.7 Hz, 1H), 3.16 (dd, J=13.3, 8.1 Hz, 1H), 3.03 (t, J=6.8 Hz, 2H), 2.58-2.51 (m, 1H), 2.32-2.25 (m, 4H), 2.12-2.02 (m, 1H), 1.80 (s, 3H).

Example 21 rel-(4aS,10bS)-10b-methyl-9-(5-(prop-1-yn-1-yl)pyridin-3-yl)-4,5,6,10b-tetrahydro-4H-naphtho[1,2-d][1,3]thiazin-2-amine, bis(2,2,2-trifluoroacetate)

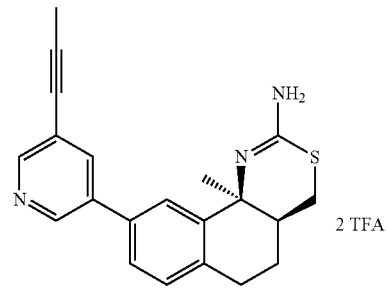 [SMILES: CC#Cc1cncc(-c2ccc3c(c2)[C@@]2(C)N=C(N)SC[C@H]2CC3)c1]

In a manner similar to the two step procedure described for example 19, the compound of preparation C was converted to the compound of example 21 in 29% overall yield. LCMS (M+H)$^+$=348.12. $^1$H NMR (500 MHz, chloroform-d) δ 9.02 (br. s., 1H), 8.71-8.63 (m, 2H), 8.13 (s, 1H), 7.56 (d, J=8.1 Hz, 1H), 7.32 (d, J=7.9 Hz, 1H), 3.26-3.19 (m, 1H), 3.16-3.09 (m, 1H), 3.00 (t, J=6.6 Hz, 2H), 2.47 (br. s., 1H), 2.33-2.24 (m, 1H), 2.18-2.09 (m, 4H), 1.84 (s, 3H).

Example 22 rel-(4aS,11bS)-11b-methyl-10-(5-(prop-1-yn-1-yl)pyridin-3-yl)-4a,5,6,11b-tetrahydro-4H-benzo[2,3]oxepino[4,5-d][1,3]thiazin-2-amine, bis(2,2,2-trifluoroacetate)

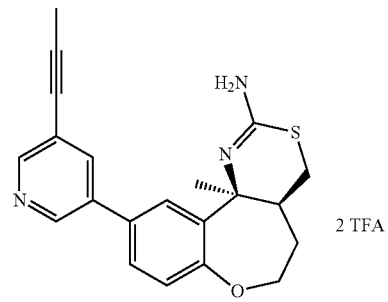 [SMILES: CC#Cc1cncc(-c2ccc3c(c2)[C@@]2(C)N=C(N)SC[C@H]2CCO3)c1]

A mixture of dimethoxyethane (2 mL), water (1.0 mL), and ethanol (0.6 mL) was purged with nitrogen (bubbling via pipette) for 15 min. The degassed solvent was transferred to a vial charged with a mixture of tert-butyl rel-((4aS,11bS)-10-bromo-11b-methyl-4a,5,6,11b-tetrahydro-4H-benzo[2,3]oxepino[4,5-d][1,3]thiazin-2-yl)carbamate from preparation H (25 mg, 0.058 mmol), (5-(prop-1-yn-1-yl)pyridin-3-yl)boronic acid (75 mg, 0.468 mmol), bis(triphenylphosphine)palladium(II) chloride (8.2 mg, 0.012 mmol), and Cs$_2$CO$_3$ (152 mg, 0.468 mmol). The vial was capped and heated to 100° C. for 20 min. The reaction was cooled, diluted with water, and extracted with EtOAc. The organic layer was dried over sodium sulfate, filtered and concentrated in vacuo. The crude products were dissolved in dichloromethane (1.0 mL). TFA (0.3 mL) was added and the mixture was allowed to stir at rt for 20 hours. The reaction mixture was concentrated under reduced pressure. The residue was purified using reverse phase preparatory HPLC (Sunfire PrepC18 OBD 10 µm, 50×250 mm column, 90% MeOH/10% water/0.1% TFA-90% MeOH/10% water/0.1% TFA, linear gradient over 34 min, 50 mL/min) to afford the titled compound of example 22 (7.8 mg, 0.013 mmol, 21% yield) as a colorless residue. LCMS (M+H)$^+$=364.1. $^1$H NMR (500 MHz, methanol-d$_4$) δ 8.68 (br. s., 1H), 8.57 (br. s., 1H), 8.08-8.04 (m, 1H), 7.67 (dd, J=8.2, 2.4 Hz, 1H), 7.32-7.23 (m, 2H), 4.45-4.36 (m, 1H), 3.86-3.76 (m, 1H), 3.08-2.96 (m, 2H), 2.95-2.84 (m, 1H), 2.61-2.52 (m, 1H), 2.12 (s, 3H), 1.98 (d, J=5.5 Hz, 1H), 1.92 (s, 3H).

Example 22a (4aR,11bR)-11b-Methyl-10-(5-(prop-1-yn-1-yl)pyridin-3-yl)-4a,5,6,11b-tetrahydro-4H-benzo[2,3]oxepino[4,5-d][1,3]thiazin-2-amine

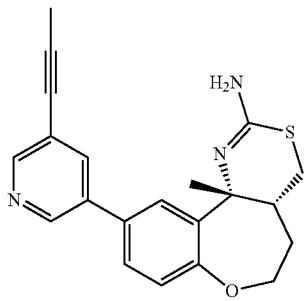 [SMILES: CC#Cc1cncc(-c2ccc3c(c2)[C@]2(C)N=C(N)SC[C@@H]2CCO3)c1]

Example 22b (4aS,11bS)-11b-Methyl-10-(5-(prop-1-yn-1-yl)pyridin-3-yl)-4a,5,6,11b-tetrahydro-4H-benzo[2,3]oxepino[4,5-d][1,3]thiazin-2-amine

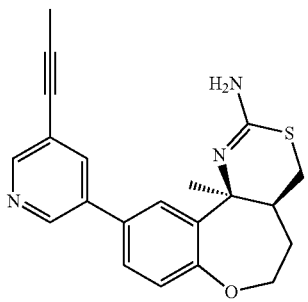 [SMILES: CC#Cc1cncc(-c2ccc3c(c2)[C@@]2(C)N=C(N)SC[C@H]2CCO3)c1]

A sample of example 21 (racemic mixture) was separated using chiral HPLC under the following conditions: column=Chiracel AS-H 4.6×100 mm 5 µm, flow rate=1.0 mL/min, isocratic elution of 10% solvent B/90% solvent A, where solvent A=0.1% diethylamine in n-heptane and solvent B=ethanol. Example 22a eluted at 4.2 min and example 22b eluted at 7.5 min. $^1$H NMR and LCMS data of the individual enantiomers were identical to those reported for the racemic sample of example 22.

Example 23 rel-(4aS,11bS)-11b-Methyl-10-(1-methyl-1H-pyrazol-4-yl)-4a,5,6,11b-tetrahydro-4H-benzo[2,3]oxepino[4,5-d][1,3]thiazin-2-amine, bis(2,2,2-trifluoroacetate)

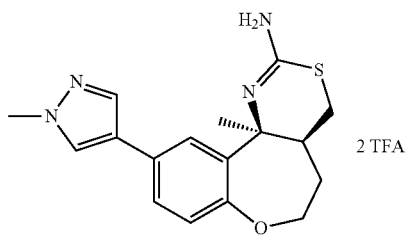 [SMILES: Cn1cc(-c2ccc3c(c2)[C@@]2(C)N=C(N)SC[C@H]2CCO3)cn1]

In a manner similar to the two-step procedure used for the preparation of example 22, but using 1-methyl-4-(4,4,5,5-tetramethyl-1,3,2-dioxaborinan-2-yl)-1H-pyrazole (130 mg, 0.585 mmol), potassium carbonate (81 mg, 0.585 mmol), and bis(diphenylphosphino)ferrocenepalladium(II) dichloride (24 mg, 0.029 mmol) as starting materials, the compound of preparation H was converted to the titled compound of example 23 (19 mg, 0.032 mmol, 55% yield over two steps) was prepared as a white residue. LCMS (M+H)$^+$=329.14. $^1$H NMR (500 MHz, methanol-d$_4$) δ 7.89 (s, 1H), 7.72 (s, 1H), 7.50 (dd, J=8.2, 2.2 Hz, 1H), 7.18 (d, J=2.1 Hz, 1H), 7.11 (d, J=8.1 Hz, 1H), 3.94 (s, 3H), 3.75 (td, J=13.1, 1.4 Hz, 1H), 3.03-2.97 (m, 2H), 2.86 (ddt, J=15.4, 13.4, 4.5 Hz, 1H), 2.52 (td, J=9.8, 4.1 Hz, 1H), 1.90 (s, 3H).

Example 24 rel-(4aS,11bS)-11b-methyl-10-(1H-pyrazol-4-yl)-4a,5,6,11b-tetrahydro-4H-benzo[2,3]oxepino[4,5-d][1,3]thiazin-2-amine, bis(2,2,2-trifluoroacetate)

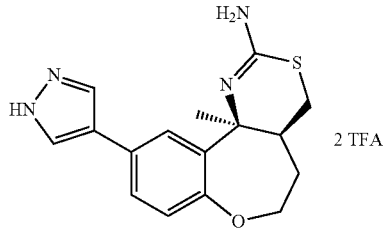 [SMILES: C[C@]12N=C(N)SC[C@H]1CCOc1ccc(-c3cn[nH]c3)cc12]

In a manner similar to the two-step procedure reported for example 23, the compound of preparation H was converted to the titled compound of example 24 in a 35% overall yield. MS (M+H)$^+$=315.13. $^1$H NMR (500 MHz, methanol-d$_4$) δ 7.91 (br. s., 2H), 7.54 (dd, J=8.1, 2.1 Hz, 1H), 7.21 (d, J=2.1 Hz, 1H), 7.12 (d, J=8.2 Hz, 1H), 4.38-4.32 (m, 1H), 3.76 (td, J=13.1, 1.3 Hz, 1H), 3.03-2.97 (m, 2H), 2.92-2.83 (m, 1H), 2.56-2.50 (m, 1H), 1.94 (d, J=2.7 Hz, 1H), 1.91 (s, 3H).

Example 25 rel-(4aS,11bS)-10-(Isoxazol-4-yl)-11b-methyl-4a,5,6,11b-tetrahydro-4H-benzo[2,3]oxepino[4,5-d][1,3]thiazin-2-amine, 2,2,2-trifluoroacetate salt

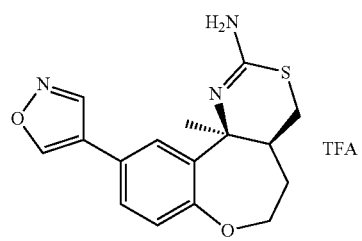 [SMILES: C[C@]12N=C(N)SC[C@H]1CCOc1ccc(-c3cnoc3)cc12]

In a manner similar to the two-step procedure reported for example 23, the compound of preparation H was converted to the titled compound of example 25 in a 22% overall yield. LCMS (M+H)$^+$=316.12. $^1$H NMR (500 MHz, methanol-$d_4$) δ 9.02 (s, 1H), 8.76 (s, 1H), 7.61 (dd, J=8.2, 2.2 Hz, 1H), 7.23 (d, J=2.1 Hz, 1H), 7.19 (d, J=8.2 Hz, 1H), 4.40-4.33 (m, 1H), 3.78 (td, J=13.1, 1.5 Hz, 1H), 3.05-2.95 (m, 2H), 2.92-2.83 (m, 1H), 2.58-2.51 (m, 1H), 1.98-1.92 (m, 1H), 1.90 (s, 3H).

Example 26 rel-(4aS,11bS)-11b-Methyl-10-(2-methylthiazol-5-yl)-4a,5,6,11b-tetrahydro-4H-benzo[2,3]oxepino[4,5-d][1,3]thiazin-2-amine, 2,2,2-trifluoroacetate salt

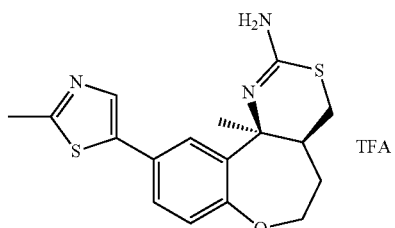

In a manner similar to the two-step procedure reported for example 23, the compound of preparation H was converted to the titled compound of example 26 in a 94% overall yield. MS (M+H)$^+$=346.13. $^1$H NMR (500 MHz, methanol-$d_4$) δ 7.82 (s, 1H), 7.60 (dd, J=8.2, 2.3 Hz, 1H), 7.22 (d, J=2.1 Hz, 1H), 7.18 (d, J=8.2 Hz, 1H), 4.40-4.34 (m, 1H), 3.78 (td, J=13.1, 1.4 Hz, 1H), 3.05-2.95 (m, 2H), 2.93-2.84 (m, 1H), 2.74 (s, 3H), 2.55 (dq, J=12.0, 4.0 Hz, 1H), 1.97-1.91 (m, 1H), 1.90 (s, 3H).

Example 26a (4aR,11bR)-11b-Methyl-10-(2-methylthiazol-5-yl)-4a,5,6,11b-tetrahydro-4H-benzo[2,3]oxepino[4,5-d][1,3]thiazin-2-amine

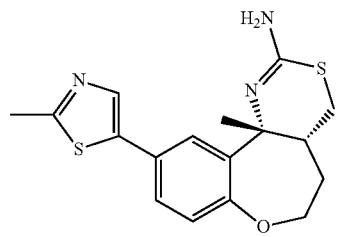 [SMILES: Cc1ncc(-c2ccc3c(c2)[C@]2(C)N=C(N)SC[C@@H]2CCO3)s1]

Example 26b (4aS,11bS)-11b-Methyl-10-(2-methylthiazol-5-yl)-4a,5,6,11b-tetrahydro-4H-benzo[2,3]oxepino[4,5-d][1,3]thiazin-2-amine

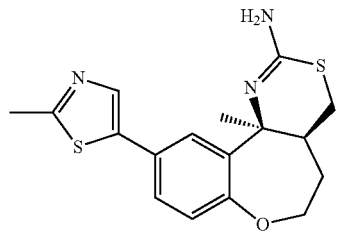 [SMILES: Cc1ncc(-c2ccc3c(c2)[C@@]2(C)N=C(N)SC[C@H]2CCO3)s1]

A sample of the compound of Example 26 (racemic) was separated by chiral HPLC under the following conditions: column=Chiralpak AD-H 30×250 mm 5 μm, flow rate=70 mL/min, isocratic elution of 15% solvent B/85% solvent A, where solvent A=0.1% diethylamine in n-heptane and solvent B=ethanol. The compound of Example 26a eluted at 18.3 min and the compound of example 26b eluted at 22.0 min. $^1$H NMR and LCMS data were identical to those reported for the racemic compound of example 26.

Example 27 rel-(4aS,11bS)-11b-methyl-10-(pyrimidin-5-yl)-4a,5,6,11b-tetrahydro-4H-benzo[2,3]oxepino[4,5-d][1,3]thiazin-2-amine, bis(2,2,2-trifluoroacetate)

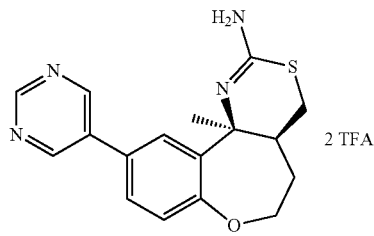 [SMILES: C[C@]12N=C(N)SC[C@H]1CCOc1ccc(-c3cncnc3)cc12]

In a manner similar to the two-step procedure reported for example 23, the compound of preparation H was converted to the titled compound of example 27 in a 17% overall yield. LCMS (M+H)$^+$=327.1. $^1$H NMR (500 MHz, methanol-d$_4$) δ 9.17 (s, 1H), 9.02 (s, 2H), 7.73 (dd, J=8.2, 2.4 Hz, 1H), 7.35-7.27 (m, 2H), 4.45-4.36 (m, 1H), 3.82 (td, J=13.2, 1.6 Hz, 1H), 3.08-2.97 (m, 2H), 2.96-2.85 (m, 1H), 2.62-2.53 (m, 1H), 2.01-1.88 (m, 4H).

Example 28 rel-2-((4aS,11bS)-2-amino-11b-methyl-4a,5,6,11b-tetrahydro-4H-benzo[2,3]oxepino[4,5-d][1,3]thiazin-10-yl)-1H-indole-5-carbonitrile, 2,2,2-trifluoroacetate salt

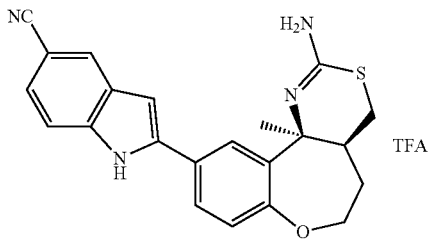 [SMILES: C[C@]12N=C(N)SC[C@H]1CCOc1ccc(-c3cc4cc(C#N)ccc4[nH]3)cc12]

In a manner similar to the two-step procedure reported for example 23, the compound of preparation H was converted to the titled compound of example 28 in a 42% overall yield. LCMS (M+H)$^+$=389.13. $^1$H NMR (500 MHz, chloroform-d) δ 11.36 (s, 1H), 10.43 (br. s., 1H), 7.91 (d, J=1.1 Hz, 1H), 7.73-7.63 (m, 2H), 7.52 (d, J=8.4 Hz, 1H), 7.38 (dd, J=8.4, 1.5 Hz, 1H), 7.16 (d, J=8.2 Hz, 1H), 6.77 (d, J=1.5 Hz, 1H), 4.40 (dt, J=12.9, 3.7 Hz, 1H), 3.81 (td, J=12.6, 1.8 Hz, 1H), 3.22 (t, J=12.4 Hz, 1H), 2.89-2.77 (m, 2H), 2.53 (dd, J=12.6, 3.7 Hz, 3H), 1.93 (s, 3H).

Example 29 rel-(4aS,11bS)-10-(isoquinolin-4-yl)-11b-methyl-4a,5,6,11b-tetrahydro-4H-benzo[2,3]oxepino[4,5-d][1,3]thiazin-2-amine, bis(2,2,2-trifluoroacetate)

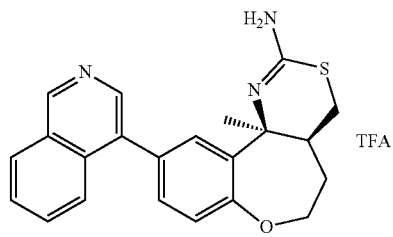 [SMILES: C[C@]12N=C(N)SC[C@H]1CCOc1ccc(-c3cncc4ccccc34)cc12]

In a manner similar to the two-step procedure reported for example 23, the compound of preparation H was converted to the titled compound of example 29 in a 65% overall yield. LCMS (M+H)$^+$=376.13. $^1$H NMR (500 MHz, chloroform-d) δ 9.59 (br. s., 1H), 8.55 (br. s., 1H), 8.39 (d, J=7.9 Hz, 1H), 8.21 (d, J=8.5 Hz, 1H), 8.12 (t, J=7.7 Hz, 1H), 8.00-7.94 (m, 1H), 7.48 (d, J=8.1 Hz, 1H), 7.33 (d, J=8.1 Hz, 2H), 4.49 (d, J=11.4 Hz, 1H), 3.81 (t, J=13.1 Hz, 1H), 3.08 (t, J=12.6 Hz, 1H), 3.03-2.93 (m, 1H), 2.84 (d, J=9.9 Hz, 1H), 2.52 (d, J=10.7 Hz, 1H), 2.05 (s, 3H), 1.92 (d, J=14.8 Hz, 1H).

Example 30 rel-(4aS,11bS)-10-(1H-indol-3-yl)-11b-methyl-4a,5,6,11b-tetrahydro-4H-benzo[2,3]oxepino[4,5-d][1,3]thiazin-2-amine, 2,2,2-trifluoroacetate salt

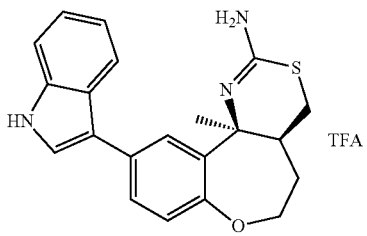 [SMILES: C[C@]12N=C(N)SC[C@H]1CCOc1ccc(-c3c[nH]c4ccccc34)cc12]

In a manner similar to the two-step procedure reported for example 23, the compound of preparation H was converted to the titled compound of example 30 in a 21% overall yield. LCMS (M+H)$^+$=364.13. $^1$H NMR (500 MHz, methanol-d$_4$) δ 7.85 (dd, J=7.9, 0.9 Hz, 1H), 7.59 (dd, J=8.2, 2.2 Hz, 1H), 7.52-7.39 (m, 3H), 7.25-7.06 (m, 3H), 4.44-4.30 (m, 1H), 3.87-3.70 (m, 1H), 3.14-2.99 (m, 2H), 2.90 (d, J=1.8 Hz, 1H), 2.55 (dd, J=12.4, 3.8 Hz, 1H), 2.00-1.85 (m, 4H).

Example 31 rel-(4aS,11bS)-10-(4-(4-Methoxyphenyl)-1H-imidazol-1-yl)-11b-methyl-4a,5,6,11b-tetrahydro-4H-benzo[2,3]oxepino[4,5-d][1,3]thiazin-2-amine, bis(2,2,2-trifluoroacetate)

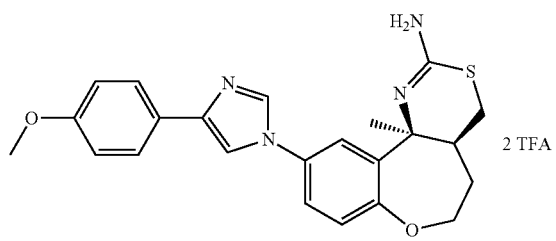 [SMILES: COc1ccc(-c2cn(-c3ccc4c(c3)[C@@]3(C)N=C(N)SC[C@H]3CCO4)cn2)cc1]

Step 31A. Methyl 7-(4-(4-methoxyphenyl)-1H-imidazol-1-yl)-5-methyl-2,3-dihydrobenzo[b]oxepine-4-carboxylate To an oven dried microwave vial was added methyl 7-bromo-5-methyl-2,3-dihydrobenzo[b]oxepine-4-carboxylate from step H5 (200 mg, 0.673 mmol), 4-(4-methoxyphenyl)-1H-imidazole (141 mg, 0.808 mmol), potassium carbonate (186 mg, 1.35 mmol) and copper(I) iodide (72.9 mg, 0.383 mmol). The vial was capped with a septum and the system was degassed and flushed with nitrogen (3×). Then 2,2,6,6-tetramethylheptane-3,5-dione (0.194 mL, 0.944 mmol) and DMF (5 mL) were added and the reaction mixture was degassed and flushed with nitrogen (3×). The vial was sealed and place in a pre-heated oil bath at 120° C. The reaction mixture was stirred at 120° C. for 20 h. The reaction was poured into water to afford a blue mixture that was extracted with ethyl acetate. The combined organic layers were washed with brine, dried over sodium sulfate, filtered and concentrated in vacuo. The crude material was purified by silica gel column chromatography (30-100% EtOAc/hexanes) to afford methyl 7-(4-(4-methoxyphenyl)-1H-imidazol-1-yl)-5-methyl-2,3-dihydrobenzo[b]oxepine-4-carboxylate (180 mg, 0.461 mmol, 69% yield). LCMS (M+H)$^+$=391.1. $^1$H NMR (500 MHz, chloroform-d) δ 7.88 (br. s., 1H), 7.77 (d, J=7.2 Hz, 2H), 7.39-7.33 (m, 3H), 7.18 (d, J=8.4 Hz, 1H), 6.94 (d, J=7.5 Hz, 2H), 4.59 (t, J=6.0 Hz, 2H), 3.87-3.82 (m, 6H), 2.57 (t, J=5.9 Hz, 2H), 2.49 (s, 3H).

Step 31B. (7-(4-(4-Methoxyphenyl)-1H-imidazol-1-yl)-5-methyl-2,3-dihydrobenzo[b]oxepin-4-yl)methanol In a manner similar to that reported for step H6, the compound of step 31A was converted to the compound of step 31B in a quantitative yield. MS (M+H)$^+$=363.15.

Step 31C. 1-(4-(Chloromethyl)-5-methyl-2,3-dihydrobenzo[b]oxepin-7-yl)-4-(4-methoxyphenyl)-1H-imidazole In a manner similar to that reported for step H7, the compound of step 31B was converted to the compound of step 31C in a quantitative yield. MS (M+H)$^+$=381.15.

Step 31D. rel-(4aS,11bS)-10-(4-(4-Methoxyphenyl)-1H-imidazol-1-yl)-11b-methyl-4a,5,6,11b-tetrahydro-4H-benzo[2,3]oxepino[4,5-d][1,3]thiazin-2-amine, bis(2,2,2-trifluoroacetate)

In a manner similar to that reported for steps H8 and H9, the compound of step 31C was converted to the titled compound of example 31 in 27% overall yield. LCMS (M+H)$^+$=421.15. $^1$H NMR (500 MHz, DMSO-d$_6$) δ 9.22 (br. s., 4H), 8.42 (s, 1H), 7.84-7.75 (m, 3H), 7.68 (dd, J=8.7, 2.7 Hz, 1H), 7.25 (d, J=8.7 Hz, 1H), 7.11-7.02 (m, 2H), 4.53 (t, J=6.2 Hz, 2H), 4.25 (br. s., 2H), 3.82 (s, 3H), 2.35-2.27 (m, 2H), 2.21 (s, 3H).

Example 32 rel-(4aS,11bS)-11b-Methyl-10-(1H-pyrazol-1-yl)-4a,5,6,11b-tetrahydro-4H-benzo[2,3]oxepino[4,5-d][1,3]thiazin-2-amine, 2,2,2-trifluoroacetate

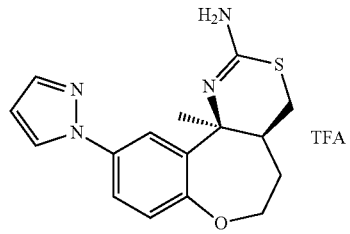 [SMILES: C[C@]12N=C(N)SC[C@H]1CCOc1ccc(-n3cccn3)cc12]

Step 32A. Methyl 5-methyl-7-(1H-pyrazol-1-yl)-2,3-dihydrobenzo[b]oxepine-4-carboxylate In a manner similar to that reported for step 31A, the compound of step H5 was converted to the compound of step 32A in 32% yield. MS (M+H)$^+$=285.1.

Step 32B. (5-Methyl-7-(1H-pyrazol-1-yl)-2,3-dihydrobenzo[b]oxepin-4-yl)methanol

In a manner similar to that reported for step H6, the compound of step 32A was converted to the compound of step 32B in quantitative yield. MS (M+H)$^+$=257.2.

Step 32C. 1-(4-(Chloromethyl)-5-methyl-2,3-dihydrobenzo[b]oxepin-7-yl)-1H-pyrazole In a manner similar to that reported for step H7, the compound of step 32B was converted to the compound of step 32C in quantitative yield. MS (M+H)$^+$=275.1.

Step 32D. rel-(4aS,11bS)-11b-methyl-10-(1H-pyrazol-1-yl)-4a,5,6,11b-tetrahydro-4H-benzo[2,3]oxepino[4,5-d][1,3]thiazin-2-amine, 2,2,2-trifluoroacetate salt In a manner similar to that reported for steps H8 and H9, the compound of step 32C was converted to the titled compound of example 32 in a 62% overall yield. LCMS (M+H)$^+$=315.15. $^1$H NMR (500 MHz, methanol-d$_4$) δ 8.20 (dd, J=2.5, 0.5 Hz, 1H), 7.75-7.69 (m, 2H), 7.60 (dd, J=8.6, 2.7 Hz, 1H), 7.16 (d, J=8.7 Hz, 1H), 6.54 (t, J=2.2 Hz, 1H), 4.56 (t, J=6.3 Hz, 2H), 4.27 (s, 2H), 2.38 (s, 2H), 2.26 (s, 3H).

Example 33 rel-N-((4aS,11bS)-2-amino-11b-methyl-4a,5,6,11b-tetrahydro-4H-benzo[2,3]oxepino[4,5-d][1,3]thiazin-10-yl)-5-chloropicolinamide, 2,2,2-trifluoroacetate salt

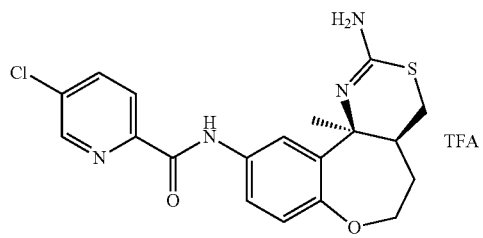 [SMILES: C[C@]12N=C(N)SC[C@H]1CCOc1ccc(NC(=O)c3ccc(Cl)cn3)cc12]

In a manner similar to the two-step procedure used for the preparation of example 7, but using tert-butyl rel-((4aS,11bS)-10-amino-11b-methyl-4a,5,6,11b-tetrahydro-4H-benzo[2,3]oxepino[4,5-d][1,3]thiazin-2-yl)carbamate from preparation I (89 mg, 0.245 mmol) as the starting material, the titled compound of example 33 (52 mg, 0.099 mmol, 40% yield) was prepared as a white solid. LCMS (M+H)$^+$ 403.1. $^1$H NMR (500 MHz, DMSO-d$_6$) δ 10.85 (s, 1H), 10.33 (br. s., 1H), 8.79 (dd, J=2.4, 0.7 Hz, 1H), 8.23-8.18 (m, 1H), 8.16-8.11 (m, 1H), 7.85-7.76 (m, 2H), 7.10-7.03 (m, 1H), 4.26 (dt, J=10.8, 1.8 Hz, 1H), 3.64 (t, J=12.7 Hz, 1H), 3.01 (dd, J=12.3, 3.1 Hz, 1H), 2.78 (t, J=12.7 Hz, 1H), 2.71-2.60 (m, 1H), 2.47-2.34 (m, 1H), 1.87 (d, J=13.9 Hz, 1H), 1.76 (s, 3H).

Example 33a

N-((4aS,11bS)-2-amino-11b-methyl-4a,5,6,11b-tetrahydro-4H-benzo[2,3]oxepino[4,5-d][1,3]thiazin-10-yl)-5-chloropicolinamide

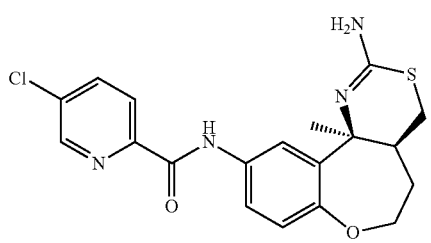 [SMILES: C[C@]12N=C(N)SC[C@H]1CCOc1ccc(NC(=O)c3ccc(Cl)cn3)cc12]

Example 33b

N-((4aR,11bR)-2-amino-11b-methyl-4a,5,6,11b-tetrahydro-4H-benzo[2,3]oxepino[4,5-d][1,3]thiazin-10-yl)-5-chloropicolinamide

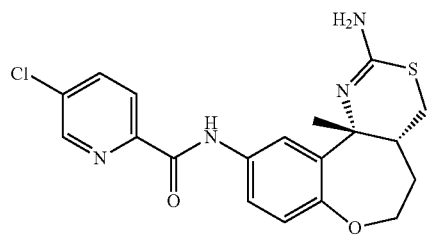 [SMILES: C[C@@]12N=C(N)SC[C@@H]1CCOc1ccc(NC(=O)c3ccc(Cl)cn3)cc12]

A sample of the compound of example 33 (racemic) was separated by chiral HPLC under the following conditions: column=Chiracel OD-H 4.6×100 mm 5 μm, flow rate=1.0 mL/min, isocratic elution of 30% solvent B/90% solvent A, where solvent A=0.1% diethylamine in n-heptane and solvent B=ethanol. The compound of example 33a eluted at 2.95 min and the compound of example 33b eluted at 4.76 min. $^1$H NMR and LCMS data were identical to those reported for the racemic compound of example 33.

Example 34 rel-N-((4aS,11bS)-2-Amino-11b-methyl-4a,5,6,11b-tetrahydro-4H-benzo[2,3]oxepino[4,5-d][1,3]thiazin-10-yl)-3,5-dichloropicolinamide, 2,2,2-trifluoroacetate salt

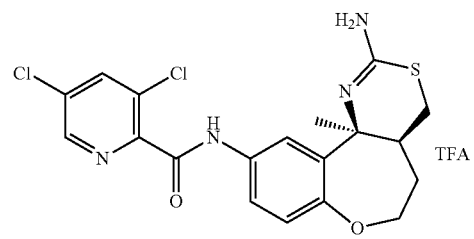 [SMILES: C[C@]12N=C(N)SC[C@H]1CCOc1ccc(NC(=O)c3ncc(Cl)cc3Cl)cc12]

In a manner similar to the two-step procedure used for the preparation of example 7, but using tert-butyl rel-((4aS,11bS)-10-amino-11b-methyl-4a,5,6,11b-tetrahydro-4H-benzo[2,3]oxepino[4,5-d][1,3]thiazin-2-yl)carbamate from preparation I as the starting material, the titled compound of Example 34 was prepared in 41% yield. LCMS (M+H)$^+$=437.1. $^1$H NMR (500 MHz, methanol d$_{-4}$) δ 9.42 (d, J=2.0 Hz, 1H), 9.04 (s, 1H), 8.46 (d, J=1.7 Hz, 1H), 8.36 (dd, J=8.5, 2.5 Hz, 1H), 7.85 (d, J=8.5 Hz, 1H), 4.44 (t, J=12.8 Hz, 1H), 4.03-3.99 (m, 1H), 3.78-3.72 (m, 1H), 3.64 (t, J=12.6 Hz, 1H), 3.57-3.44 (m, 1H), 3.21 (dd, J=12.9, 3.7 Hz, 1H), 2.64 (d, J=13.6 Hz, 1H), 2.58 (s, 3H).

Example 34a

N-((4aS,11bS)-2-Amino-11b-methyl-4a,5,6,11b-tetrahydro-4H-benzo[2,3]oxepino[4,5-d][1,3]thiazin-10-yl)-3,5-dichloropicolinamide

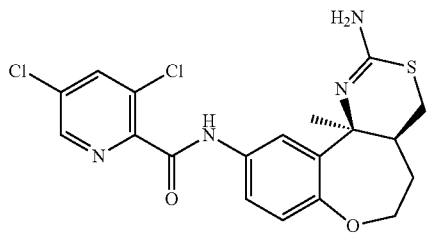 [SMILES: C[C@]12N=C(N)SC[C@H]1CCOc1ccc(NC(=O)c3ncc(Cl)cc3Cl)cc12]

Example 34b

N-((4aR,11bR)-2-Amino-11b-methyl-4a,5,6,11b-tetrahydro-4H-benzo[2,3]oxepino[4,5-d][1,3]thiazin-10-yl)-3,5-dichloropicolinamide

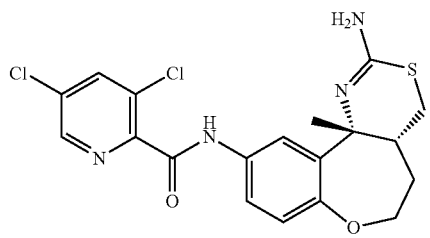 [SMILES: C[C@@]12N=C(N)SC[C@@H]1CCOc1ccc(NC(=O)c3ncc(Cl)cc3Cl)cc12]

A sample of the compound of example 34 (racemic) was separated by chiral HPLC under the following conditions: column=Chiracel OD 21×250 mm 10 μm, flow rate=15 mL/min, isocratic elution of 20% solvent B/90% solvent A, where solvent A=0.1% diethylamine in n-heptane and solvent B=ethanol. The compound of Example 34a eluted at 11.8 min and the compound of example 34b eluted at 17.2 min. $^1$H NMR and LCMS data were identical to those reported for the racemic compound of example 34.

Example 35 rel-N-((4aS,11bS)-2-Amino-11b-methyl-4a,5,6,11b-tetrahydro-4H-benzo[2,3]oxepino[4,5-d][1,3]thiazin-10-yl)-5-cyanopicolinamide, 2,2,2-trifluoroacetate salt

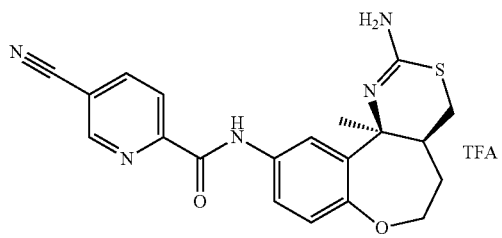 [SMILES: C[C@]12N=C(N)SC[C@H]1CCOc1ccc(NC(=O)c3ccc(C#N)cn3)cc12]

In a manner similar to the two-step procedure used for the preparation of example 7, but using tert-butyl rel-((4aS,11bS)-10-amino-11b-methyl-4a,5,6,11b-tetrahydro-4H-benzo[2,3]oxepino[4,5-d][1,3]thiazin-2-yl)carbamate from preparation I as the starting material, the titled compound of example 35 was prepared in 29% yield. LCMS (M+H)$^+$ 394.21. $^1$H NMR (500 MHz, methanol-d$_4$) δ 9.88 (s, 1H), 9.24 (dd, J=8.1, 1.8 Hz, 1H), 9.06 (d, J=8.1 Hz, 1H), 8.63-8.59 (m, 1H), 8.52 (d, J=8.7 Hz, 1H), 7.86 (d, J=8.7 Hz, 1H), 5.09-5.03 (m, 1H), 4.45 (t, J=12.6 Hz, 1H), 3.75 (dd, J=12.4, 3.2 Hz, 1H), 3.64 (t, J=12.6 Hz, 1H), 3.56-3.44 (m, 1H), 3.25-3.19 (m, 1H), 2.65 (d, J=13.9 Hz, 1H), 2.58 (s, 3H).

Example 35a

N-((4aR,11bR)-2-amino-11b-methyl-4a,5,6,11b-tetrahydro-4H-benzo[2,3]oxepino[4,5-d][1,3]thiazin-10-yl)-5-cyanopicolinamide

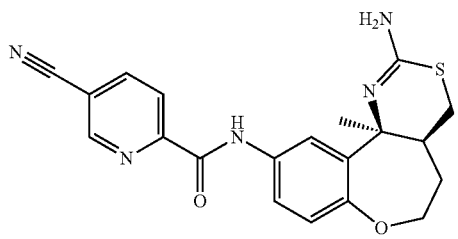 [SMILES: C[C@]12N=C(N)SC[C@H]1CCOc1ccc(NC(=O)c3ccc(C#N)cn3)cc12]

Example 35b

N-((4aS,11bS)-2-amino-11b-methyl-4a,5,6,11b-tetrahydro-4H-benzo[2,3]oxepino[4,5-d][1,3]thiazin-10-yl)-5-cyanopicolinamide

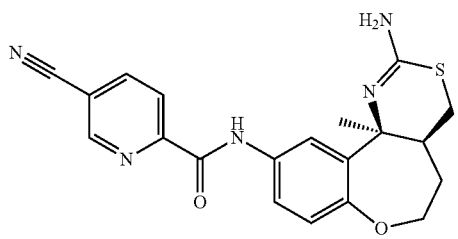 [SMILES: C[C@]12N=C(N)SC[C@H]1CCOc1ccc(NC(=O)c3ccc(C#N)cn3)cc12]

A sample of the compound of example 35 (racemic) was separated by chiral HPLC under the following conditions: column=Chiracel AS 21×250 mm 10 μm, flow rate=15 mL/min, isocratic elution of 25% solvent B/90% solvent A, where solvent A=0.1% diethylamine in n-heptane and solvent B=ethanol. The compound of example 35a eluted at 13.8 min and the compound of example 35b eluted at 21.4 min. $^1$H NMR and LCMS data were identical to those reported for the racemic compound of example 35.

Example 36 rel-N-((4aS,11bS)-2-Amino-11b-methyl-4a,5,6,11b-tetrahydro-4H-benzo[2,3]oxepino[4,5-d][1,3]thiazin-10-yl)-5-fluoropicolinamide, 2,2,2-trifluoroacetate salt

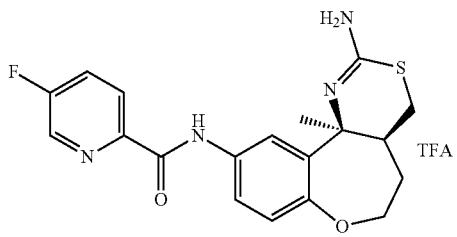 [SMILES: C[C@]12N=C(N)SC[C@H]1CCOc1ccc(NC(=O)c3ccc(F)cn3)cc12]

In a manner similar to the two-step procedure used for the preparation of example 7, but using tert-butyl rel-((4aS,11bS)-10-amino-11b-methyl-4a,5,6,11b-tetrahydro-4H-benzo[2,3]oxepino[4,5-d][1,3]thiazin-2-yl)carbamate from preparation I as the starting material, the titled compound of example 36 was prepared in 48% yield. MS (M+H)$^+$ 387.1. $^1$H NMR (500 MHz, methanol-$d_4$) δ 8.61 (s, 1H), 8.28 (dd, J=8.8, 4.5 Hz, 1H), 7.91-7.76 (m, 2H), 7.63 (dd, J=8.5, 2.6 Hz, 1H), 7.13 (d, J=8.5 Hz, 1H), 4.40-4.26 (m, 1H), 3.75 (td, J=13.2, 1.4 Hz, 1H), 3.03-2.97 (m, 2H), 2.87 (ddt, J=15.3, 13.4, 4.5 Hz, 1H), 2.57-2.49 (m, 1H), 1.95 (br. s., 1H), 1.93-1.89 (m, 3H).

Example 36a

N-((4aS,11bS)-2-Amino-11b-methyl-4a,5,6,11b-tetrahydro-4H-benzo[2,3]oxepino[4,5-d][1,3]thiazin-10-yl)-5-fluoropicolinamide

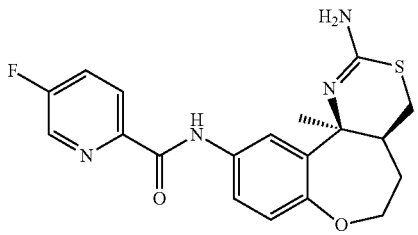 [SMILES: C[C@]12N=C(N)SC[C@H]1CCOc1ccc(NC(=O)c3ccc(F)cn3)cc12]

Example 36b

N-((4aR,11bR)-2-Amino-11b-methyl-4a,5,6,11b-tetrahydro-4H-benzo[2,3]oxepino[4,5-d][1,3]thiazin-10-yl)-5-fluoropicolinamide

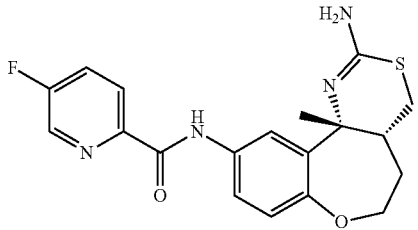 [SMILES: C[C@@]12N=C(N)SC[C@@H]1CCOc1ccc(NC(=O)c3ccc(F)cn3)cc12]

A sample of the compound of Example 36 (racemic) was separated by chiral HPLC under the following conditions: column=Chiracel AD 21×250 mm 10 μm, flow rate=15 mL/min, isocratic elution of 30% solvent B/90% solvent A, where solvent A=0.1% diethylamine in n-heptane and solvent B=ethanol. The compound of example 36a eluted at 14.0 min and the compound of example 36b eluted at 19.1 min. $^1$H NMR and LCMS data were identical to those reported for the racemic compound of example 36.

Example 37 rel-(4aS,11bS)—N10-(3-Chloropyridin-2-yl)-11b-methyl-4a,5,6,11b-tetrahydro-4H-benzo[2,3]oxepino[4,5-d][1,3]thiazine-2,10-diamine, bis(2,2,2-trifluoroacetate)

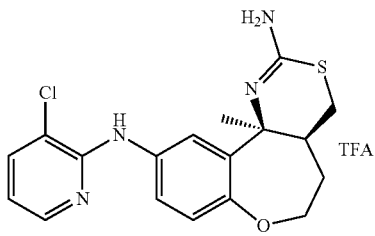 [SMILES: C[C@]12N=C(N)SC[C@H]1CCOc1ccc(Nc3ncccc3Cl)cc12]

Step 37A. tert-butyl rel-((4aS,11bS)-10-((3-chloropyridin-2-yl)amino)-11b-methyl-4a,5,6,11b-tetrahydro-4H-benzo[2,3]oxepino[4,5-d][1,3]thiazin-2-yl)carbamate An oven dried vial was charged with brettphos precatalyst (12 mg, 0.014 mmol), brettphos (7.6 mg, 0.014 mmol), 2,3-dichloropyridine (8.5 mg, 0.058 mmol), tert-butyl rel-((4aS,11bS)-10-amino-11b-methyl-4a,5,6,11b-tetrahydro-4H-benzo[2,3]oxepino[4,5-d][1,3]thiazin-2-yl)carbamate from preparation I (25 mg, 0.069 mmol) and LiHMDS (14 mg, 0.086 mmol). The vial was purged with nitrogen. Dioxane (1 mL) was added. The vial was placed in a preheated oil bath at 100° C. for 1 h. The reaction was then diluted with ethyl acetate and saturated aqueous ammonium chloride solution. The organic layer was washed with water, brine, and dried over sodium sulfate. The organic layer was filtered and concentrated in vacuo to afford tert-butyl rel-((4aS,11bS)-10-((3-chloropyridin-2-yl)amino)-11b-methyl-4a,5,6,11b-tetrahydro-4H-benzo[2,3]oxepino[4,5-d][1,3]thiazin-2-yl) carbamate (27 mg, 0.057 mmol, 99% yield). The crude material was used in the next step without further purification. MS (M+H)$^+$=475.26.

Step 37B. rel-((4aS,11bS)—N10-(3-chloropyridin-2-yl)-11b-methyl-4a,5,6,11b-tetrahydro-4H-benzo[2,3]oxepino[4,5-d][1,3]thiazine-2,10-diamine, bis(2,2,2-trifluoroacetate)

tert-Butyl rel-((4aS,11bS)-10-((3-chloropyridin-2-yl)amino)-11b-methyl-4a,5,6,11b-tetrahydro-4H-benzo[2,3]oxepino[4,5-d][1,3]thiazin-2-yl)carbamate from step 37A (27 mg, 0.057 mmol) was dissolved in DCM (2 mL) and to this was added TFA (0.5 mL, 6.49 mmol). The reaction mixture was stirred at rt for 16 h. The solvent was removed in vacuo. The crude residue was purified by Prep HPLC column chromatography (Luna Axia C18, 10 μm, 30×100 mm column, 90% MeOH/10% water/0.1% TFA-90% MeOH/10% water/0.1% TFA, linear gradiant over 20 min, 40 mL/min) to afford the titled compound of example 37 (5.5 mg, 8.7 μmol, 15% yield) as a light orange residue. LCMS (M+H)$^+$ 375.1. $^1$H NMR (500 MHz, methanol-$d_4$) δ 8.03 (dd, J=5.0, 1.6 Hz, 1H), 7.79 (d, J=2.7 Hz, 1H), 7.75 (dd, J=7.8, 1.5 Hz, 1H), 7.36

(dd, J=8.5, 2.7 Hz, 1H), 7.07 (d, J=8.4 Hz, 1H), 6.81 (dd, J=7.8, 4.9 Hz, 1H), 4.36-4.29 (m, 1H), 3.73 (t, J=12.5 Hz, 1H), 3.10-3.03 (m, 1H), 3.01-2.96 (m, 1H), 2.92-2.82 (m, 1H), 2.54-2.47 (m, 1H), 1.95-1.89 (m, 4H).

Example 38 rel-(4aS,11bS)—N10-(3-Methoxypyridin-2-yl)-11b-methyl-4a,5,6,11b-tetrahydro-4H-benzo[2,3]oxepino[4,5-d][1,3]thiazine-2,10-diamine, bis(2,2,2-trifluoroacetate)

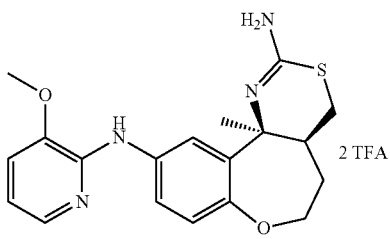 [SMILES: COc1cccnc1Nc1ccc2c(c1)[C@@]1(C)N=C(N)SC[C@H]1CCO2]

In a manner similar to that reported for example 37, the compound of preparation I was converted to the compound of example 38 in a 4% overall yield. MS (M+H)+ 371.13. 1H NMR (500 MHz, methanol-d4) δ 7.62-7.47 (m, 2H), 7.44-7.33 (m, 2H), 7.17 (d, J=8.5 Hz, 1H), 6.89 (dd, J=7.8, 5.8 Hz, 1H), 4.46-4.29 (m, 1H), 4.03 (s, 3H), 3.76 (t, J=12.5 Hz, 1H), 3.11-2.96 (m, 2H), 2.88 (dd, J=15.3, 13.4 Hz, 1H), 2.62-2.43 (m, 1H), 2.01-1.80 (m, 4H).

Example 39 rel-2-(((4aS,11bS)-2-Amino-11b-methyl-4a,5,6,11b-tetrahydro-4H-benzo[2,3]oxepino[4,5-d][1,3]thiazin-10-yl)amino)nicotinonitrile, bis(2,2,2-trifluoroacetate)

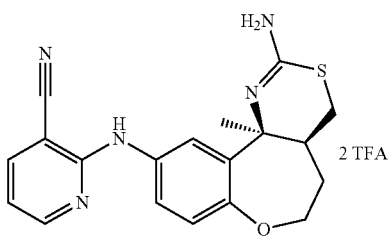 [SMILES: C[C@]12N=C(N)SC[C@H]1CCOc1ccc(Nc3ncccc3C#N)cc12]

In a manner similar to that reported for example 37, the compound of preparation I was converted to the compound of Example 39 in a 52% overall yield. MS (M+H)+ 366.1. 1H NMR (500 MHz, methanol-d4) δ 8.56 (dd, J=7.6, 1.5 Hz, 1H), 8.30-8.17 (m, 1H), 7.65-7.55 (m, 1H), 7.47-7.38 (m, 2H), 7.19-7.08 (m, 1H), 4.50-4.42 (m, 1H), 3.95-3.81 (m, 1H), 3.10-2.99 (m, 1H), 2.97-2.86 (m, 1H), 2.63-2.50 (m, 1H), 2.05-1.86 (m, 4H).

Example 40 rel-(4aS,11bS)-11b-Methyl-N10-(quinazolin-4-yl)-4a,5,6,11b-tetrahydro-4H-benzo[2,3]oxepino[4,5-d][1,3]thiazine-2,10-diamine, bis(2,2,2-trifluoroacetate)

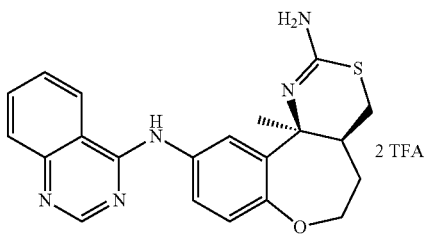 [SMILES: C[C@]12N=C(N)SC[C@H]1CCOc1ccc(Nc3ncnc4ccccc34)cc12]

In a manner similar to that reported for example 37, the compound of preparation I was converted to the compound of example 40 in a 6% overall yield. MS (M+H)+ 392.1. 1H NMR (500 MHz, methanol-d4) δ 8.78 (s, 1H), 8.63 (d, J=8.2 Hz, 1H), 8.14 (td, J=7.8, 1.2 Hz, 1H), 7.98-7.86 (m, 2H), 7.80-7.65 (m, 2H), 7.24 (d, J=8.5 Hz, 1H), 4.46-4.34 (m, 1H), 3.82 (t, J=12.5 Hz, 1H), 3.11-2.99 (m, 2H), 2.96-2.85 (m, 1H), 2.57 (dd, J=10.3, 6.0 Hz, 1H), 2.02-1.87 (m, 4H).

Example 41 rel-(4aS,11bS)—N10-(Isoquinolin-1-yl)-11b-methyl-4a,5,6,11b-tetrahydro-4H-benzo[2,3]oxepino[4,5-d][1,3]thiazine-2,10-diamine, bis(2,2,2-trifluoroacetate)

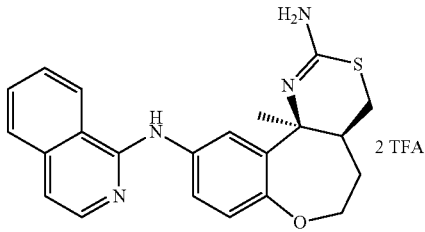 [SMILES: C[C@]12N=C(N)SC[C@H]1CCOc1ccc(Nc3nccc4ccccc34)cc12]

In a manner similar to that reported for example 37, the compound of preparation I was converted to the compound of Example 41 in a 8% overall yield. MS (M+H)+ 391.1. 1H NMR (500 MHz, methanol-d4) δ 8.58 (s, 1H), 8.09-7.96 (m, 2H), 7.92-7.81 (m, 1H), 7.65-7.48 (m, 2H), 7.35 (dd, J=12.7, 7.6 Hz, 3H), 4.48-4.36 (m, 1H), 3.85 (t, J=12.4 Hz, 1H), 3.13-3.00 (m, 2H), 2.97-2.85 (m, 1H), 2.63-2.50 (m, 1H), 2.04-1.86 (m, 4H).

Example 42 rel-(4aS,11bS)—N10-(4-Methoxypyrimidin-2-yl)-11b-methyl-4a,5,6,11b-tetrahydro-4H-benzo[2,3]oxepino[4,5-d][1,3]thiazine-2,10-diamine, bis(2,2,2-trifluoroacetate)

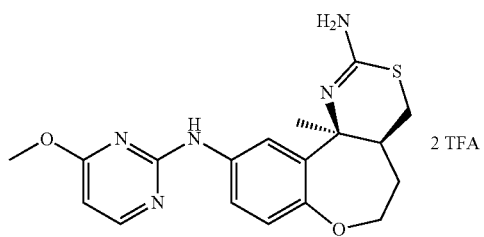 [SMILES: COc1ccnc(Nc2ccc3c(c2)[C@@]2(C)N=C(N)SC[C@H]2CCO3)n1]

In a manner similar to that reported for example 37, the compound of preparation I was converted to the compound of example 42 in a 5% overall yield. LCMS (M+H)$^+$ 372.1. $^1$H NMR (500 MHz, methanol-d$_4$) δ 8.10 (d, J=6.1 Hz, 1H), 7.65-7.49 (m, 2H), 7.10 (d, J=8.5 Hz, 1H), 6.34 (d, J=6.1 Hz, 1H), 4.39-4.28 (m, 1H), 4.00 (s, 3H), 3.73 (t, J=13.0 Hz, 1H), 3.10-2.95 (m, 2H), 2.90-2.80 (m, 1H), 2.59-2.48 (m, 1H), 1.98-1.85 (m, 4H).

Example 43 rel-N-((4aS,11bS)-2-Amino-11b-methyl-4,4a,5,6,7,11b-hexahydrobenzo[6,7]cyclohepta[1,2-d][1,3]thiazin-10-yl)-5-fluoropicolinamide, 2,2,2-trifluoroacetate

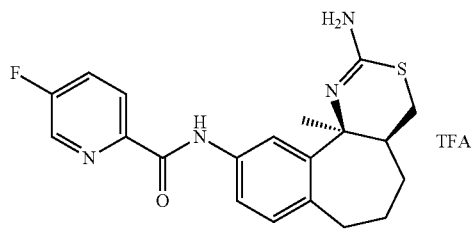 [SMILES: C[C@]12N=C(N)SC[C@H]1CCCc1ccc(NC(=O)c3ccc(F)cn3)cc12]

Step 43A. (E)-Methyl 2-(5-fluoropicolinamido)-9-methyl-6,7-dihydro-5H-benzo[7]annulene-8-carboxylate In a manner similar to the procedure of step 3A, methyl 2-amino-9-methyl-6,7-dihydro-5H-benzo[7]annulene-8-carboxylate from preparation J, step J1, was coupled with 5-fluoropicolinic acid to afford the titled compound of Step 43A. $^1$H NMR (500 HMz, chloroform-d) δ 9.82 (br. s., 1H), 8.48 (d, J=2.7 Hz, 1H), 8.36 (dd, J=8.7, 4.6 Hz, 1H), 7.73 (d, J=2.3 Hz, 1H), 7.66-7.59 (m, 2H), 7.22 (d, J=8.1 Hz, 1H), 3.83 (s, 3H), 2.57 (t, J=6.6 Hz, 2H), 2.45 (s, 3H), 2.17-2.10 (m, 4H).

Step 43B. (E)-5-Fluoro-N-(8-(hydroxymethyl)-9-methyl-6,7-dihydro-5H-benzo[7]annulen-2-yl)picolinamide In a manner similar to the procedure of step 3B, (E)-methyl 2-(5-fluoropicolinamido)-9-methyl-6,7-dihydro-5H-benzo[7]annulene-8-carboxylate from step 43A was reduced with DIBAL to afford the titled compound of Step 43B. LCMS (M+H)$^+$=327.2. $^1$H NMR (500 HMz, chloroform-d) δ 9.79 (s, 1H), 8.44 (d, J=2.7 Hz, 1H), 8.35-8.31 (m, 1H), 7.65 (d, J=2.3 Hz, 1H), 7.61-7.56 (m, 1H), 7.54 (dd, J=8.1, 2.3 Hz, 1H), 7.17 (d, J=8.1 Hz, 1H), 4.38 (s, 2H), 2.53 (t, J=7.0 Hz, 2H), 2.13 (s, 3H), 2.09 (quin, J=7.1 Hz, 2H), 2.02-1.95 (m, 3H).

Step 43C. (E)-N-(8-(Chloromethyl)-9-methyl-6,7-dihydro-5H-benzo[7]annulen-2-yl)-5-fluoropicolinamide In a manner similar to the procedure of step 3C, (E)-5-fluoro-N-(8-(hydroxymethyl)-9-methyl-6,7-dihydro-5H-benzo[7]annulen-2-yl)picolinamide from step 43B was converted into the titled compound of Step 43C. $^1$H NMR (500 HMz, chloroform-d) δ 9.79 (br. s., 1H), 8.46 (d, J=2.7 Hz, 1H), 8.35 (dd, J=8.7, 4.6 Hz, 1H), 7.70 (d, J=2.1 Hz, 1H), 7.63-7.58 (m, 1H), 7.56 (dd, J=8.1, 2.3 Hz, 1H), 7.19 (d, J=8.1 Hz, 1H), 4.36 (s, 2H), 2.57 (t, J=7.1 Hz, 2H), 2.21 (s, 3H), 2.17 (quin, J=7.1 Hz, 2H), 2.03-1.98 (m, 2H).

Step 43D. rel-N-((4aS,11bS)-2-Amino-11b-methyl-4,4a,5,6,7,11b-hexahydrobenzo[6,7]cyclohepta[1,2-d][1,3]thiazin-10-yl)-5-fluoropicolinamide, 2,2,2-trifluoroacetate In a manner similar to the procedure of step 3D, (E)-N-(8-(chloromethyl)-9-methyl-6,7-dihydro-5H-benzo[7]annulen-2-yl)-5-fluoropicolinamide from step 43C was converted into the titled compound of example 43. LCMS (M+H)$^+$=385.2. $^1$H NMR (500 HMz, methanol-d$_4$) δ 8.61 (d, J=2.9 Hz, 1H), 8.30-8.26 (m, 1H), 7.87 (d, J=2.3 Hz, 1H), 7.82 (td, J=8.5, 2.9 Hz, 1H), 7.60 (dd, J=8.2, 2.2 Hz, 1H), 7.27 (d, J=8.1 Hz, 1H), 3.19-3.10 (m, 1H), 2.96-2.82 (m, 3H), 2.56-2.42 (m, 2H), 2.10 (dd, J=14.6, 3.8 Hz, 1H), 1.90 (dd, J=13.9, 4.3 Hz, 1H), 1.86 (s, 3H), 1.59 (d, J=14.0 Hz, 1H).

Example 43a

N-((4aR,11bR)-2-Amino-11b-methyl-4,4a,5,6,7,11b-hexahydrobenzo[6,7]cyclohepta[1,2-d][1,3]thiazin-10-yl)-5-fluoropicolinamide

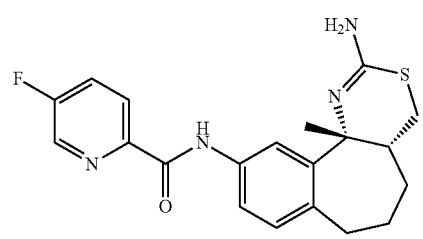 [SMILES: C[C@@]12N=C(N)SC[C@@H]1CCCc1ccc(NC(=O)c3ccc(F)cn3)cc12]

Example 43b

N-((4aS,11bS)-2-Amino-11b-methyl-4,4a,5,6,7,11b-hexahydrobenzo[6,7]cyclohepta[1,2-d][1,3]thiazin-10-yl)-5-fluoropicolinamide

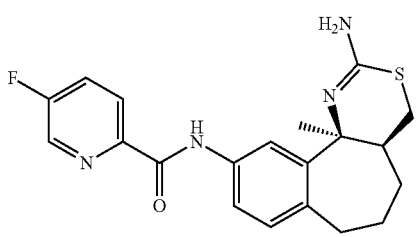 [SMILES: C[C@]12N=C(N)SC[C@H]1CCCc1ccc(NC(=O)c3ccc(F)cn3)cc12]

A sample of the compound of example 43 (racemic TFA salt) was separated by chiral HPLC under the following conditions: column=Chiralpak AD 21×250 mm 10 um, flow rate=15 mL/min, isocratic elution of 20% solvent B/80% solvent A, where solvent A=0.1% diethylamine in n-heptane and solvent B=ethanol. The compound of example 43a eluted at 19.1 min and the compound of example 43b eluted at 24.5 min. $^1$H NMR and LCMS data of the individual enantiomers 43a and 43b were identical. LCMS (M+H)$^+$=385.2. $^1$H NMR (500 HMz, chloroform-d) δ 9.77 (br. s., 1H), 8.45 (d, J=2.7 Hz, 1H), 8.33 (dd, J=8.7, 4.6 Hz, 1H), 7.91 (dd, J=8.1, 2.3 Hz, 1H), 7.61-7.56 (m, 1H), 7.34 (d, J=2.3 Hz, 1H), 7.16 (d, J=8.1 Hz, 1H), 3.17-3.08 (m, 1H), 2.86-2.78 (m, 2H), 2.57 (dd, J=11.6, 3.1 Hz, 1H), 2.48-2.39 (m, 1H), 2.16-2.09 (m, 1H), 1.96 (dd, J=14.5, 4.1 Hz, 1H), 1.73 (s, 3H), 1.63-1.53 (m, 1H)

Example 44 rel-N-((4aS,11bS)-2-amino-11b-methyl-4,4a,5,6,7,11b-hexahydrobenzo[6,7]cyclohepta[1,2-d][1,3]thiazin-10-yl)-5-cyanopicolinamide, 2,2,2-trifluoroacetate

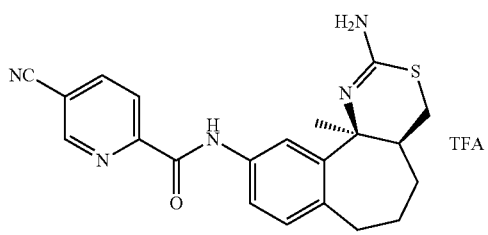 [SMILES: C[C@]12N=C(N)SC[C@H]1CCCc1ccc(NC(=O)c3ccc(C#N)cn3)cc12]

Step 44A. (E)-5-Cyano-N-(8-(hydroxymethyl)-9-methyl-6,7-dihydro-5H-benzo[7]annulen-2-yl)picolinamide In a manner similar to the procedure of step 3A, (E)-(2-amino-9-methyl-6,7-dihydro-5H-benzo[7]annulen-8-yl)methanol from preparation J was coupled with 5-cyanopicolinic acid to afford the titled compound of Step 44A. $^1$H NMR (500 HMz, chloroform-d) δ 9.84 (s, 1H), 8.90 (dd, J=2.0, 0.8 Hz, 1H), 8.45 (dd, J=8.1, 0.8 Hz, 1H), 8.21 (dd, J=8.1, 2.0 Hz, 1H), 7.68 (d, J=2.3 Hz, 1H), 7.56 (dd, J=8.1, 2.3 Hz, 1H), 7.21 (d, J=8.2 Hz, 1H), 4.41 (s, 2H), 2.56 (t, J=7.0 Hz, 2H), 2.16 (s, 3H), 2.12 (quin, J=7.1 Hz, 2H), 2.02-1.96 (m, 2H), 1.57 (br. s., 1H).

Step 44B. (E)-N-(8-(Chloromethyl)-9-methyl-6,7-dihydro-5H-benzo[7]annulen-2-yl)-5-cyanopicolinamide In a manner similar to the procedure of step 3C, (E)-5-cyano-N-(8-(hydroxymethyl)-9-methyl-6,7-dihydro-5H-benzo[7]annulen-2-yl)picolinamide from step 44A was converted into the titled compound of Step 44B. $^1$H NMR (500 HMz, chloroform-d) δ 9.85 (br. s., 1H), 8.92 (dd, J=1.9, 0.8 Hz, 1H), 8.46 (dd, J=8.2, 0.8 Hz, 1H), 8.23 (dd, J=8.1, 2.0 Hz, 1H), 7.70 (d, J=2.3 Hz, 1H), 7.58 (dd, J=8.2, 2.3 Hz, 1H), 7.22 (d, J=8.1 Hz, 1H), 4.37 (s, 2H), 2.59 (t, J=7.1 Hz, 2H), 2.22 (s, 3H), 2.21-2.14 (m, 2H), 2.04-1.99 (m, 2H)

Step 44C. rel-N-((4aS,11bS)-2-amino-11b-methyl-4,4a,5,6,7,11b-hexahydrobenzo[6,7]cyclohepta[1,2-d][1,3]thiazin-10-yl)-5-cyanopicolinamide, 2,2,2-trifluoroacetate In a manner similar to the procedure of step 3D, (E)-N-(8-(chloromethyl)-9-methyl-6,7-dihydro-5H-benzo[7]annulen-2-yl)-5-cyanopicolinamide from step 44B was converted into the titled compound of example 44. $^1$H NMR (500 HMz, methanol-d$_4$) δ 9.04 (dd, J=2.0, 0.8 Hz, 1H), 8.41 (dd, J=8.2, 2.1 Hz, 1H), 8.37-8.33 (m, 1H), 7.90 (d, J=2.1 Hz, 1H), 7.63 (dd, J=8.2, 2.2 Hz, 1H), 7.28 (d, J=8.2 Hz, 1H), 3.19-3.10 (m, 1H), 2.98-2.88 (m, 2H), 2.88-2.81 (m, 1H), 2.57-2.42 (m, 2H), 2.10 (dd, J=14.6, 3.7 Hz, 1H), 1.94-1.88 (m, 1H), 1.87 (s, 3H), 1.59 (d, J=14.0 Hz, 1H).

Example 44a

N-((4aR,11bR)-2-Amino-11b-methyl-4,4a,5,6,7,11b-hexahydrobenzo[6,7]cyclohepta[1,2-d][1,3]thiazin-10-yl)-5-cyanopicolinamide

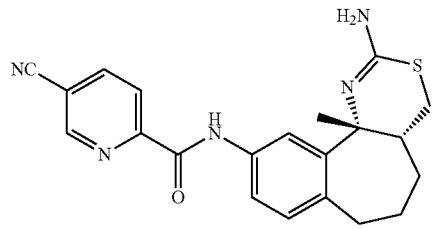 [SMILES: C[C@@]12N=C(N)SC[C@@H]1CCCc1ccc(NC(=O)c3ccc(C#N)cn3)cc12]

Example 44b

N-((4aS,11bS)-2-Amino-11b-methyl-4,4a,5,6,7,11b-hexahydrobenzo[6,7]cyclohepta[1,2-d][1,3]thiazin-10-yl)-5-cyanopicolinamide

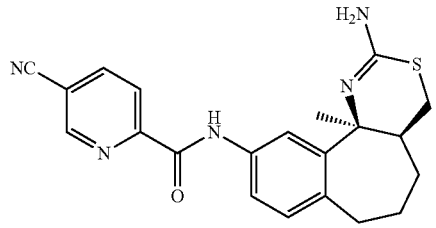 [SMILES: C[C@]12N=C(N)SC[C@H]1CCCc1ccc(NC(=O)c3ccc(C#N)cn3)cc12]

A sample of the compound of example 44 (racemic TFA salt) was separated by chiral HPLC under the following conditions: column=Chiralpak AS 21×250 mm 10 um, flow rate=15 mL/min, isocratic elution of 18% solvent B/82% solvent A, where solvent A=0.1% diethylamine in n-heptane and solvent B=ethanol. The compound of example 44a eluted at 15.9 min and the compound of example 44b eluted at 21.7 min. $^1$H NMR and LCMS data of the individual enantiomers 44a and 44b were identical. LCMS (M+H)$^+$=392.3. $^1$H NMR (500 HMz, chloroform-d) δ 9.75 (br. s., 1H), 8.76 (d, J=1.1 Hz, 1H), 8.37 (d, J=8.1 Hz, 1H), 8.16 (dd, J=8.1, 1.8 Hz, 1H), 7.81 (dd, J=8.0, 1.6 Hz, 1H), 7.39 (s, 1H), 7.10 (d, J=8.1 Hz, 1H), 4.44 (br. s., 2H), 3.13 (t, J=13.7 Hz, 1H), 2.87-2.76 (m, 2H), 2.56 (d, J=10.4 Hz, 1H), 2.49-2.39 (m, 1H), 2.11 (dd, J=12.7, 3.1 Hz, 1H), 1.95 (dd, J=14.3, 2.6 Hz, 1H), 1.88-1.80 (m, 1H), 1.74 (s, 3H), 1.56 (q, J=13.6 Hz, 1H).

Example 45 rel-N-((4aS,11bS)-2-amino-11b-methyl-4,4a,5,6,7, 11b-hexahydrobenzo[6,7]cyclohepta[1,2-d][1,3]thi- azin-10-yl)-3,5-dichloropicolinamide, 2,2,2-trifluo- roacetate

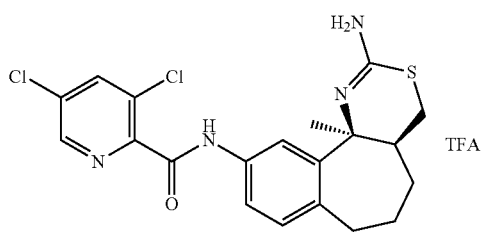 [SMILES: C[C@]12N=C(N)SC[C@H]1CCCc1ccc(NC(=O)c3ncc(Cl)cc3Cl)cc12]

TFA

Step 45A. (E)-3,5-Dichloro-N-(8-(hydroxymethyl)- 9-methyl-6,7-dihydro-5H-benzo[7]annulen-2-yl) picolinamide In a manner similar to the procedure of step 3A, (E)-(2- amino-9-methyl-6,7-dihydro-5H-benzo[7]annulen-8-yl) methanol from preparation J was coupled with 3,5-dichlo- ropicolinic acid to afford the titled compound of Step 45A. LCMS (M+H)$^+$=375.2. $^1$H NMR (500 HMz, methanol-d$_4$) δ 8.62 (d, J=2.0 Hz, 1H), 8.18 (d, J=2.1 Hz, 1H), 7.65 (d, J=2.1 Hz, 1H), 7.50 (dd, J=8.1, 2.3 Hz, 1H), 7.19 (d, J=8.2 Hz, 1H), 4.33 (s, 2H), 2.56 (t, J=7.0 Hz, 2H), 2.14 (s, 3H), 2.13-2.08 (m, 2H), 2.00-1.95 (m, 2H).

Step 45B. (E)-N-(8-(Chloromethyl)-9-methyl-6,7- dihydro-5H-benzo[7]annulen-2-yl)-3,5-dichloropi- colinamide In a manner similar to the procedure of step 3C, (E)-3,3- dichloro-N-(8-(hydroxymethyl)-9-methyl-6,7-dihydro-5H- benzo[7]annulen-2-yl)picolinamide from step 45A was con- verted into the titled compound of Step 45B. The crude material was used for the next step without purification or characterization.

Step 45C. rel-N-((4aS,11bS)-2-amino-11b-methyl-4, 4a,5,6,7,11b-hexahydrobenzo[6,7]cyclohepta[1,2-d] [1,3]thiazin-10-yl)-3,3-dichloropicolinamide, 2,2,2- trifluoroacetate In a manner similar to the procedure of step 3D, (E)-N-(8- (chloromethyl)-9-methyl-6,7-dihydro-5H-benzo[7]annulen- 2-yl)-3,3-dichloropicolinamide from step 45B was converted into the titled compound of example 45. LCMS (M+H)$^+$=435.2.

Example 45a

N-((4aS,11bS)-2-Amino-11b-methyl-4,4a,5,6,7,11b- hexahydrobenzo[6,7]cyclohepta[1,2-d][1,3]thiazin- 10-yl)-3,5-dichloropicolinamide

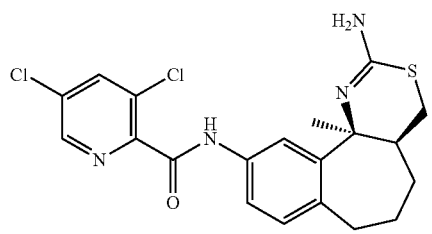 [SMILES: C[C@]12N=C(N)SC[C@H]1CCCc1ccc(NC(=O)c3ncc(Cl)cc3Cl)cc12]

Example 45b

N-((4aR,11bR)-2-Amino-11b-methyl-4,4a,5,6,7,11b- hexahydrobenzo[6,7]cyclohepta[1,2-d][1,3]thiazin- 10-yl)-3,5-dichloropicolinamide

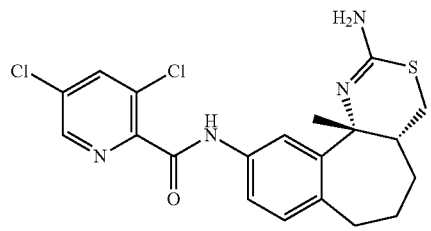 [SMILES: C[C@@]12N=C(N)SC[C@@H]1CCCc1ccc(NC(=O)c3ncc(Cl)cc3Cl)cc12]

A sample of the compound of example 45 (racemic TFA salt) was separated by chiral HPLC under the following con- ditions: column=Chiralpak AD 21×250 mm 10 um, flow rate=15 mL/min, isocratic elution of 25% solvent B/75% solvent A, where solvent A=0.1% diethylamine in n-heptane and solvent B=ethanol. The compound of example 45a eluted at 13.5 min and the compound of example 45b eluted at 18.7 min. $^1$H NMR and LCMS data of the individual enantiomers 45a and 45b were identical. LCMS (M+H)$^+$=435.05. $^1$H NMR (500 HMz, methanol-d$_4$) δ 8.59 (d, J=2.1 Hz, 1H), 8.15 (d, J=2.0 Hz, 1H), 7.71 (dd, J=8.1, 2.3 Hz, 1H), 7.44 (d, J=2.3 Hz, 1H), 7.17 (d, J=8.1 Hz, 1H), 3.16 (t, J=13.4 Hz, 1H), 2.83 (dd, J=15.0, 5.4 Hz, 1H), 2.76-2.69 (m, 1H), 2.66-2.61 (m, 1H), 2.51-2.42 (m, 1H), 2.11-2.05 (m, 1H), 1.98 (dd, J=14.5, 3.8 Hz, 1H), 1.86-1.79 (m, 1H), 1.70 (s, 3H), 1.62-1.52 (m, 1H).

Example 46 rel-N-((4aS,11bS)-2-Amino-11b-methyl-4,4a,5,6,7,11b-hexahydrobenzo[6,7]cyclohepta[1,2-d][1,3]thiazin-10-yl)-5-(difluoromethoxy)picolinamide, 2,2,2-trifluoroacetate

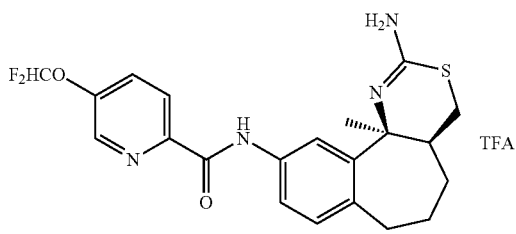 [SMILES: C[C@]12N=C(N)SC[C@H]1CCCc1ccc(NC(=O)c3ccc(OC(F)F)cn3)cc12]

Step 46A. (E)-5-(Difluoromethoxy)-N-(8-(hydroxymethyl)-9-methyl-6,7-dihydro-5H-benzo[7]annulen-2-yl)picolinamide In a manner similar to the procedure of step 3A, (E)-(2-amino-9-methyl-6,7-dihydro-5H-benzo[7]annulen-8-yl)methanol from preparation J was coupled with 5-(difluoromethoxy)picolinic acid from preparation K to afford the titled compound of step 46A. LCMS (M+H)$^+$=375.27, $^1$H NMR (500 HMz, chloroform-d) δ 9.81 (s, 1H), 8.46 (d, J=2.1 Hz, 1H), 8.32 (dd, J=8.6, 0.5 Hz, 1H), 7.68-7.64 (m, 2H), 7.55 (dd, J=8.1, 2.3 Hz, 1H), 7.18 (d, J=8.1 Hz, 1H), 6.81-6.51 (m, 1H), 4.39 (s, 2H), 2.56-2.51 (m, 2H), 2.14 (s, 3H), 2.10 (quin, J=7.1 Hz, 2H), 2.00-1.96 (m, 2H), 1.89 (br. s., 1H).

Step 46B. (E)-N-(8-(Chloromethyl)-9-methyl-6,7-dihydro-5H-benzo[7]annulen-2-yl)-5-(difluoromethoxy)picolinamide In a manner similar to the procedure of step 3C, (E)-5-(difluoromethoxy)-N-(8-(hydroxymethyl)-9-methyl-6,7-dihydro-5H-benzo[7]annulen-2-yl)picolinamide from step 46A was converted into the titled compound of Step 46B. $^1$H NMR (500 HMz, chloroform-d) δ 9.82 (s, 1H), 8.49-8.46 (m, 1H), 8.34 (dd, J=8.6, 0.5 Hz, 1H), 7.71-7.65 (m, 2H), 7.56 (dd, J=8.1, 2.3 Hz, 1H), 7.20 (d, J=8.1 Hz, 1H), 6.81-6.51 (m, 1H), 4.37 (s, 2H), 2.57 (t, J=7.1 Hz, 2H), 2.21 (s, 3H), 2.20-2.13 (m, 2H), 2.03-1.98 (m, 2H).

Step 46C. rel-N-((4aS,11bS)-2-Amino-11b-methyl-4,4a,5,6,7,11b-hexahydrobenzo[6,7]cyclohepta[1,2-d][1,3]thiazin-10-yl)-5-(difluoromethoxy)picolinamide, 2,2,2-trifluoroacetate In a manner similar to the procedure of step 3D, (E)-N-(8-(chloromethyl)-9-methyl-6,7-dihydro-5H-benzo[7]annulen-2-yl)-5-(difluoromethoxy)picolinamide from step 46B was converted into the titled compound of example 46. LCMS (M+H)$^+$=431.4.

Example 46a

N-((4aS,11bS)-2-Amino-11b-methyl-4,4a,5,6,7,11b-hexahydrobenzo[6,7]cyclohepta[1,2-d][1,3]thiazin-10-yl)-5-(difluoromethoxy)picolinamide

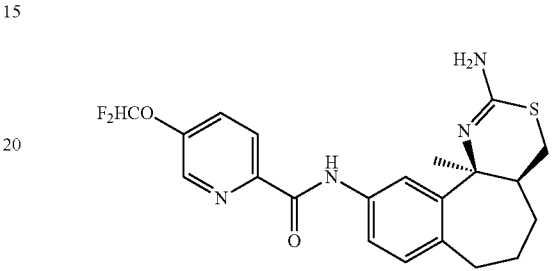

Example 46b

N-((4aR,11bR)-2-Amino-11b-methyl-4,4a,5,6,7,11b-hexahydrobenzo[6,7]cyclohepta[1,2-d][1,3]thiazin-10-yl)-5-(difluoromethoxy)picolinamide

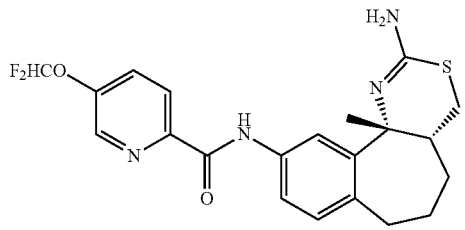 [SMILES: C[C@@]12N=C(N)SC[C@@H]1CCCc1ccc(NC(=O)c3ccc(OC(F)F)cn3)cc12]

A sample of the compound of example 46 (racemic TFA salt) was separated by chiral HPLC under the following conditions: column=Chiralpak AD 21×250 mm 10 um, flow rate=15 mL/min, isocratic elution of 25% solvent B/75% solvent A, where solvent A=0.1% diethylamine in n-heptane and solvent B=ethanol. The compound of example 46a eluted at 8.8 min and the compound of example 46b eluted at 15.8 min. $^1$H NMR and LCMS data of the individual enantiomers 46a and 46b were identical. $^1$H NMR (500 HMz, methanol-d$_4$) δ 8.55 (d, J=2.4 Hz, 1H), 8.25 (d, J=8.7 Hz, 1H), 7.80 (dd, J=8.6, 2.7 Hz, 1H), 7.72 (dd, J=8.1, 2.1 Hz, 1H), 7.51 (d, J=2.1 Hz, 1H), 7.23-6.92 (m, 2H), 3.16 (t, J=13.6 Hz, 1H), 2.84 (dd, J=15.0, 5.1 Hz, 1H), 2.77-2.70 (m, 1H), 2.67-2.61 (m, 1H), 2.52-2.43 (m, 1H), 2.13-2.06 (m, 1H), 1.99 (dd, J=14.5, 3.5 Hz, 1H), 1.87-1.80 (m, 1H), 1.72 (s, 3H), 1.57 (d, J=13.6 Hz, 1H).

Example 47 rel-(4aS,11bS)-9-fluoro-11b-methyl-10-(pyrimidin-5-yl)-4,4a,5,6,7,11b-hexahydrobenzo[6,7]cyclohepta[1,2-d][1,3]thiazin-2-amine, bis(2,2,2-trifluoroacetate)

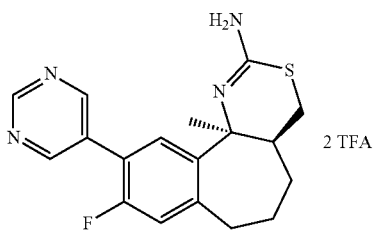 [SMILES: C[C@]12N=C(N)SC[C@H]1CCCc1cc(F)c(-c3cncnc3)cc12]

Step 47A. rel-(4aS,11bS)-9-fluoro-11b-methyl-10-(pyrimidin-5-yl)-4,4a,5,6,7,11b-hexahydrobenzo[6,7]cyclohepta[1,2-d][1,3]thiazin-2-amine, bis-N—N-(tert-butyl)carbamate In a manner similar to that reported for step 1A of example 1, the compound of preparation L was converted to the compound of step 47A. LCMS (M+H)$^+$=543.5. $^1$H NMR (500 HMz, chloroform-d) δ 9.17 (s, 1H), 9.07 (d, J=1.1 Hz, 2H), 7.85 (d, J=8.2 Hz, 1H), 7.02 (d, J=11.3 Hz, 1H), 3.19 (t, J=13.2 Hz, 1H), 2.93-2.87 (m, 1H), 2.87-2.82 (m, 1H), 2.68 (dd, J=12.1, 2.6 Hz, 1H), 2.46-2.38 (m, 1H), 2.17-2.11 (m, 1H), 2.10-2.04 (m, 1H), 1.94-1.87 (m, 1H), 1.81 (s, 3H), 1.53 (s, 18H), 1.49-1.45 (m, 1H).

Step 2B. rel-(4aS,11bS)-9-fluoro-11b-methyl-10-(pyrimidin-5-yl)-4,4a,5,6,7,11b-hexahydrobenzo[6,7]cyclohepta[1,2-d][1,3]thiazin-2-amine, bis(2,2,2-trifluoroacetate)

In a manner similar to that reported for step 1B of example 1, the compound of step 47A was converted to the compound of example 47. LCMS (M+H)$^+$=525.3. $^1$H NMR (500 MHz, chloroform-d) δ 9.17 (s, 1H), 9.10 (s, 2H), 7.96 (d, J=1.8 Hz, 1H), 7.40 (dd, J=7.8, 2.0 Hz, 1H), 7.27 (d, J=1.0 Hz, 2H), 3.21 (t, J=13.4 Hz, 1H), 2.98-2.85 (m, 2H), 2.66 (dd, J=11.9, 2.4 Hz, 1H), 2.50-2.38 (m, J=13.9, 13.9 Hz, 1H), 2.21-2.12 (m, 1H), 2.11-2.03 (m, J=3.7 Hz, 1H), 1.97-1.86 (m, 1H), 1.84 (s, 3H), 1.64-1.58 (m, J=13.7 Hz, 1H), 1.55 (s, 18H).

BIOLOGICAL METHODS

Cellular Assays for Inhibition of Aβ1-40 and Aβ1-42 Production

H4 cells stably transfected with APP751 containing the Swedish mutation (H4 APP751 SWE clone 8.20, developed at BMS) were maintained in log phase through twice weekly passage at a 1:20 split. For IC$_{50}$ determinations, 30 μl cells (1.5×10$^4$ cells/well) in DMEM media containing 0.0125% BSA (Sigma A8412) were plated directly into 384-well compound plates (Costar 3709) containing 0.1 μl serially diluted compound in DMSO. Following incubation for 19 h in 5% CO$_2$ at 37° C., plates were briefly centrifuged (1000 rpm, 5 min). A 10 μl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to APC (Perkin Elmer)) were mixed and 20 μl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 μl of the mixture was added to the 10 μl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and IC$_{50}$ values determined using curve fitting in CurveMaster (Excel Fit based).

The activity of representative compounds of the present invention, based on Aβ42 cellular IC$_{50}$ values in H4 APP751 SWE clone 8.20, are illustrated below in Table 1.

TABLE 1

Cellular activity of examples

| Example# | IC$_{50}$ (nM) |
|---|---|
| 1 | 5200 |
| 1a | 1900 |
| 1b | 28000 |
| 2 | 3400 |
| 3 | 34 |
| 3a | 8.8 |
| 3b | 6700 |
| 4 | >30000 |
| 5 | 4600 |
| 6 | 2600 |
| 7 | 1100 |
| 7a | 3500 |
| 7b | 1200 |
| 8 | 3100 |
| 9 | 2100 |
| 10 | 13000 |
| 11 | 3400 |
| 12 | 3400 |
| 13 | 3100 |
| 14 | 2100 |
| 15 | 3600 |
| 16 | 2500 |
| 17 | 3200 |
| 18 | 6100 |
| 19 | 8000 |
| 20 | >30000 |
| 21 | 1800 |
| 22 | 960 |
| 22a | 8200 |
| 22b | 1400 |
| 23 | 5100 |
| 24 | 8100 |
| 25 | 18000 |
| 26 | 8500 |
| 26a | 4500 |
| 26b | 3200 |
| 27 | 2900 |
| 28 | 9700 |
| 29 | 4600 |
| 30 | 16000 |
| 31 | 9400 |
| 32 | 11000 |
| 33 | 34 |
| 33a | 35 |
| 33b | 7800 |
| 34 | 26 |
| 34a | 6.9 |

TABLE 1-continued

Cellular activity of examples

| Example# | IC$_{50}$ (nM) |
|---|---|
| 34b | 790 |
| 35 | 28 |
| 35a | 5100 |
| 35b | 6.2 |
| 36 | 85 |
| 36a | 17 |
| 36b | 10000 |
| 37 | 1400 |
| 38 | 1300 |
| 39 | >30000 |
| 40 | 15000 |
| 41 | 16000 |
| 42 | 1500 |
| 43a | 2500 |
| 43b | 120 |
| 44a | 6800 |
| 44b | 21 |
| 45a | 7.2 |
| 45b | 920 |
| 46a | 27 |
| 46b | 3500 |
| 47 | 2700 |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of formula (I), including pharmaceutically acceptable salts thereof:

wherein X is selected from the group of $CH_2$, O, and $NR^2$;
m=0 or 1;
n=0 to 3;
$R^1$ at each instance is selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, and $C_2$-$C_4$ alkynyl;
L is a bond, —NHCO—, —NH—, or L and Z together can be absent;
Z is a $C_6$-$C_{10}$-aryl group or a 5-10 membered heterocyclic group which can be further substituted with from 0-3 substituents selected from the group of halogen, halo$C_{1-4}$ alkoxy, 4-methoxyphenyl, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, and $C_2$-$C_4$ alkynyl;
$R^2$ is selected from the group of hydrogen, benzyl, $C_1$-$C_6$ alkyl or cycloalkyl, $C_1$-$C_6$ alkoxy, acetyl, and methanesulfonyl;
and $R^3$, $R^4$ and $R^5$ are independently selected from hydrogen or $C_{1-4}$alkyl.

2. The compound of claim 1, wherein:
X is selected from $CH_2$ and O;
m=0 or 1;
n=0 to 3;
$R^1$ at each instance is selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl;
L is either a bond or is —NHCO—;
Z is a phenyl, pyridyl, pyrimidinyl, or pyrazinyl group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, and $C_2$-$C_4$ alkynyl;
and $R^3$, $R^4$ and $R^5$ are independently selected from hydrogen or $C_{1-4}$alkyl.

3. The compound of claim 2, wherein:
X is selected from $CH_2$ and O;
m=0 or 1;
n=0 to 3;
$R^1$ at each instance is selected from halogen,
L is either a bond or is —NHCO—;
Z is a phenyl, pyridyl, pyrimidinyl, or pyrazinyl group which can be further substituted with from 0-3 substituents selected from halogen, CN, or $C_2$-$C_4$ alkynyl;
$R^3$ is selected from hydrogen or $C_{1-4}$alkyl;
and $R^4$ and $R^5$ are hydrogen.

4. A compound of any claims of 1 to 3 wherein the configuration of the chiral center adjacent to the nitrogen of the aminothiazine is (S) or a pharmaceutically acceptable salt thereof.

5. The compound of claim 4, which is 5-Chloro-pyridine-2-carboxylic acid ((4aS,11bS)-2-amino-11b-methyl-4,4a,5,6,7,11b-hexahydro-3-thia-1-aza-dibenzo[a,c]cyclohepten-10-yl)-amide.

6. A pharmaceutical composition which comprises one or more of the compounds as claimed in claim 1, together with one or more pharmaceutically acceptable carriers, excipients or diluents.

7. A pharmaceutical composition which comprises one or more of the compounds as claimed in claim 4, together with one or more pharmaceutically acceptable carriers, excipients or diluents.

8. A pharmaceutical composition which comprises the compound as claimed in claim 5, together with one or more pharmaceutically acceptable carriers, excipients or diluents.

* * * * *